US008753897B2

(12) United States Patent
Ferrari et al.

(10) Patent No.: US 8,753,897 B2
(45) Date of Patent: Jun. 17, 2014

(54) NANOPOROUS SUBSTRATES FOR THE ANALYTICAL METHODS

(75) Inventors: Mauro Ferrari, Houston, TX (US); Mark Ming-Cheng Cheng, Pearland, TX (US); Giovanni Cuda, Cantazaro (IT); Marco Gaspari, Cosenza (IT); David Geho, Bluebell, PA (US); Lance Liotta, Bethesda, MD (US); Emmanuel Petricoin, Gainesville, VA (US); Fredika Robertson, Houston, TX (US); Rosa Terracciano, Soverato (IT)

(73) Assignees: The Board of Regents of The University of Texas System, Austin, TX (US); The Ohio State Research Foundation, Columbus, OH (US)

( * ) Notice: Subject to any disclaimer, the term of this patent is extended or adjusted under 35 U.S.C. 154(b) by 767 days.

(21) Appl. No.: 11/641,970

(22) Filed: Dec. 20, 2006
(Under 37 CFR 1.47)

(65) Prior Publication Data
US 2008/0277578 A1    Nov. 13, 2008

Related U.S. Application Data

(60) Provisional application No. 60/751,924, filed on Dec. 20, 2005, provisional application No. 60/874,959, filed on Dec. 15, 2006.

(51) Int. Cl.
*G01N 1/18*     (2006.01)
(52) U.S. Cl.
USPC ............................. 436/178; 250/288; 530/417

(58) Field of Classification Search
None
See application file for complete search history.

(56) References Cited

U.S. PATENT DOCUMENTS

| 5,693,785 | A | * | 12/1997 | Woodard et al. ............. 536/25.4 |
| 6,838,005 | B2 | | 1/2005 | Tepper | |
| 2003/0232340 | A1 | | 12/2003 | Anderson | |
| 2005/0227239 | A1 | | 10/2005 | Joyce | |
| 2006/0159916 | A1 | * | 7/2006 | Dubrow et al. ............... 428/357 |
| 2010/0240543 | A1 | | 9/2010 | Liotta et al. | |

FOREIGN PATENT DOCUMENTS

| WO | WO 2005/045932 | 5/2005 |
| WO | WO 2007/038523 | 4/2007 |

OTHER PUBLICATIONS

Geho et al., Bioconjugate Chemistry, vol. 17, No. 3, pp. 654-661 (May 2006).
Ferrari et al., Nature Reviews, vol. 5, pp. 161-171 (Mar. 2005).
Terracciano et al., Proteomics, vol. 6, No. 11, pp. 3243-3325 (Jan. 2006).
Jungbauer et al., Biotechnology and Bioengineering, vol. 87, No. 3, pp. 364-375 (Aug. 2004).

* cited by examiner

*Primary Examiner* — Dirk Bass
(74) *Attorney, Agent, or Firm* — Parker Highlander, PLLC

(57) ABSTRACT

Nanoporous materials can be used to enrich samples for subsequent analysis of substances contained in the sample. The method is shown to enrich the yield of species in the low molecular weight proteome, allowing detection of small peptides in the low nanomolar range.

31 Claims, 46 Drawing Sheets

Silica A

Silica B

Fig. 1
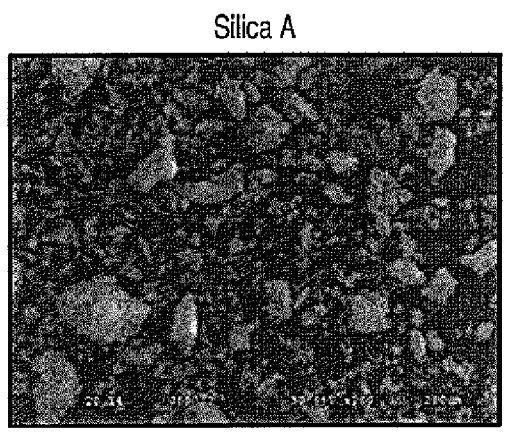
Silica A
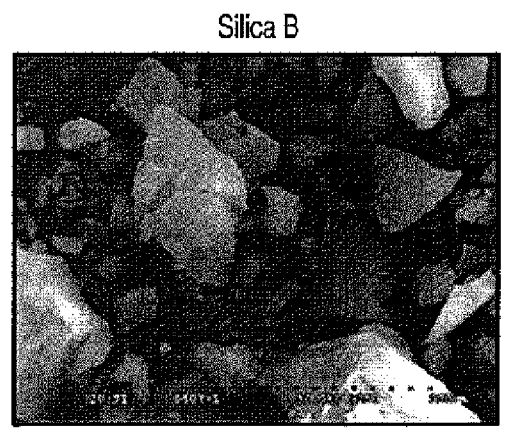
Silica B

| Peptides eluted from 70 nm-pore beads | |
|---|---|
| Protein Name | kDa Range |
| ● Complement C4 precursor | 0-10 |
| ● Apolipoprotein A-II precursor | 0-10 |
| ○ Ig gamma-1 chain C region | 0-10, 10-25 |
| ● Antithrombin-III precursor | <14 |
| ● Apolipoprotein C-I precursor | <14 |
| ● Apolipoprotein C-II precursor | <14 |
| ○ Platelet basic protein precursor | <14 |
| ● Serum amyloid A-4 protein precursor | <14 |
| ● C4b-binding protein alpha chain precursor | <14 |
| ● Gelsolin precursor, plasma | 10-25 |
| ● Lysozyme C precursor | 10-25 |
| ○ Mediator of RNA polymerase II transcription subunit 8 homolog | 10-25, 25-50 |
| ● Ig kappa chain C region | 25-50 |
| ● Apolipoprotein D precursor | 50-100 |
| ● Selenoprotein P precursor | 50-100 |
| ○ Serum albumin precursor | 50-100 |
| ○ Beta-2-glycoprotein I precursor | 50-100, 100+ |
| ○ Compliment factor H precursor | 50-100, 100+ |
| ● Apolipoprotein A-I precursor | 100+ |
| ● Histidine-rich glycoprotein precursor | ISD |
| ● Apolipoprotein A-I precursor | ISD |
| ● Apolipoprotein C-I precursor | ISD |
| ● Aldose reductase | ISD |
| ● Complement C3 precursor | ISD |
| ● Apolipoprotein A-II precursor | ISD |
| ● Apolipoprotein A-IV precursor | ISD |
| ● Complement factor B precursor | ISD |
| ● Ig gamma-3 chain C region | ISD |

| Peptides eluted from 17 nm-pore beads | |
|---|---|
| Protein Name | kDa Range |
| ● Histine H4 | 0-10 |
| ● Tetranectin precursor | <14 |
| ● Vitamin D - binding protein precursor | <14 |
| ● Transthyretin precursor | <14 |
| ○ Platelet basic protein precursor | <14 |
| ○ Ig gamma-1 chain C region | 10-25 |
| ○ Ig kappa chain C region | 25-50 |
| ○ Serum albumin precursor | 50-100 |
| ● Golgi autoantigen golgi subfamily A member 4 | 50-100 |
| ○ Beta-2 glycoprotein I precursor | 50-100 |
| ○ Complement factor H precursor | 100+ |
| ● Kinesin-like protein 2 | ISD |
| ● Serotransferrin precursor | ISD |

Fig. 12

Gel 1, Small Pore Silica Bead Eluate Samples

Gel 2, Large Pore Silica Bead Eluate Samples

Gel 3, Small Pore APTES Modified Bead Eluate Samples

Gel 4, Large Pore APTES Modified Bead Eluate Samples

Gel 5, Small Pore MPTMS Modified Bead Eluate Samples

Gel 4, Large Pore MPTMS Modified Bead Eluate Samples

NANOPOROUS SUBSTRATES FOR THE ANALYTICAL METHODS

PRIORITY CLAIM

The present application claims priority to U.S. provisional patent application No. 60/751,924, filed Dec. 20, 2005, which is incorporated herein by reference in its entirety. The present application also claims priority to U.S. provisional patent application No. 60/874,959, "Nanoporous Substrates for the Analysis of Biological Fluids", to Mauro Ferrari et. al. filed Dec. 15, 2006, which is incorporated herein by reference in its entirety.

STATEMENT FOR FEDERALLY FUNDED RESEARCH

This invention was made with government support under CO012400 and CA122864 awarded by the National Institutes of Health. The government has certain rights in the invention.

FIELD

The present application relates generally to analytical devices and systems and methods of making and using thereof and, more particularly, to analytical devices and systems utilizing nanoporous materials and methods of making and using thereof.

BACKGROUND

Various techniques for analyzing substances in a clinical sample are available, but the most common techniques require expensive solutions to resolve interference from highly abundant substances in the samples, such as albumin in the case of blood serum. One solution to this problem involves the use of antibodies to capture the highly abundant material and reduce its presence in the sample so it does not interfere with analysis of other substances of interest. There exists a need for better methods and systems to analyze substances in a sample.

SUMMARY

In one embodiment, the invention provides a method of fractionating or separating comprising (a) providing a sample comprising a first component and a second component; (b) providing a substrate comprising a nanoporous material; and (c) exposing the nanoporous material to the sample, wherein upon the exposing the nanoporous material retains the first component and does not retain the second component.

In another embodiment, the invention provides a method of analyzing a sample, comprising (a) providing the sample; (b) providing a substrate comprising a nanoporous material; and (c) exposing the nanoporous material to the sample; and analyzing a fraction of the sample retained by the nanoporous material.

In yet another embodiment, the invention provides a method of detecting a marker of a physiological condition comprising (a) providing a sample affected by the physiological condition; (b) providing a substrate comprising a nanoporous material; (c) exposing the nanoporous material to the sample; (d) analyzing a fraction of the sample retained by the nanoporous material; and (e) comparing a result of the analyzing with a result of analyzing a control sample to detect the marker of the physiological condition.

In yet another embodiment, the invention provides a kit comprising means for collecting a sample comprising one or more components; and a substrate comprising a nanoporous material configured to retain the one or more components.

In yet another embodiment, the invention provides an analytical system comprising an analytical instrument and a substrate comprising a nanoporous material, wherein the substrate is configured to enhance a sensitivity of the analytical instrument to one or more analytes.

And in yet another embodiment, the invention provides a probe comprising a substrate that comprises a nanoporous material and is configured to be inserted into a mass spectrometer.

DRAWINGS

FIG. 1 presents Scanning Electron Microscopy (SEM) images of silica A and B.

FIGS. 2 (A)-(C) present Matrix Assisted Laser Desorption Ionization—Time Of Flight (MALDI-TOF) mass spectra of Human Plasma diluted sample (FIG. 2A); Human Plasma proteins retained after exposure on nanoporous silica particles type A (FIG. 2B); and Human Plasma proteins retained after exposure on nanoporous silica particles type B (FIG. 2C).

FIGS. 3 (A)-(C) present MALDI-TOF mass spectra of Human Plasma proteins retained after exposure to nanoporous silica particles type A. A, B, C represent a set of three independent experiments.

FIGS. 4 (A)-(C) present MALDI-TOF mass spectra of Human Plasma proteins retained after exposure on nanoporous silica particles type B. A, B, C represent a set of three independent experiments.

FIGS. 5 (a)-(d) present mass spectra of spiking experiments with insulin at four different concentrations: a) 500 ng/mL; b) 200 ng/mL; c) 30 ng/mL; and 4) 15 ng/mL.

FIG. 6 schematically illustrates a strategy for partial depletion of serum using nanoporous silicon wafers. Nanoporous silicon wafers are generated and incubated with serum. After the incubation period, the wafers are removed and the remaining serum sample is spotted on a weak cation exchange chip for Surface Enhanced Laser Desorption Ionization (SELDI) mass spectrometry (MS) analysis and compared to MS spectra from control serum not exposed to the nanoporous wafer.

FIG. 7 presents results of MS analysis of serum partially depleted using a nanoporous silicon wafer. As described in FIG. 6, serum is incubated with a nanoporous silicon wafer coated with aminopropyl groups. Following incubation, the serum is bound to a weak cation exchange chip and then undergoes MS analysis. MS fingerprints are obtained. Native serum (serum not exposed to the nanoporous wafer) is compared with serum after wafer depletion. A dominant peak is present in the native serum (red/right arrow) that overshadows a smaller peak within a similar m/z range (blue/left arrow). In the serum partially depleted of its proteomic content by incubation with the nanoporous wafer, a peak designated by the blue/left arrow becomes dominant compared to the peak marked with the red/right arrow. When a ratio of relative peak intensity is compared between the blue/left and red/right peaks, a marked shift is demonstrated between the native serum and the serum after depletion using the nanoporous silicon wafer.

FIG. 8 schematically illustrates a strategy for harvesting molecules from serum using nanoporous glass beads. Glass beads coated with aminopropyl groups are incubated with serum. After the incubation period, the beads are removed, washed, and bound molecules are eluted and spotted on a weak cation exchange chip for SELDI analysis and compared to MS spectra from control serum not exposed to the nanoporous beads.

FIG. 9 presents results of MS analysis of molecules harvested by nanoporous glass beads. As described in FIG. 8, serum is incubated with glass beads coated with aminopropyl groups. Following the incubation, the serum is first bound to a weak cation exchange chip and then undergoes MS analysis. Native serum (not exposed to the nanoporous beads) is compared with molecules harvested using 17 nm beads. In the native serum, a dominant peak (red/right arrow) overshadows a smaller peak (blue/left arrow) within a similar m/z range. In the eluted sample, i.e. the sample exposed to the nanoporous glass beads, the peak designated by the blue/left arrow becomes dominant compared to the peak marked with the red/right arrow. A ratio of relative peak intensities between the blue/left and red/right peaks demonstrates a marked shift between the native serum and the molecules harvested and subsequently eluted from the nanoporous beads.

FIG. 10 presents results of MS analysis for molecules harvested by 70 nm porous beads. As described in FIG. 8, serum is incubated with glass beads having 70 nm pores and coated with aminopropyl groups. Following the incubation, serum is bound to a weak cation exchange chip and then undergoes MS analysis. Native serum (not exposed to the nanoporous beads) is compared with molecules harvested using 70 nm beads. A dominant peak (red/right arrow) overshadows in serum a smaller peak (blue/left arrow) within a similar m/z range. In the eluted sample, the peak designated by the blue arrow assumes a dominant profile when compared to the peak marked with the red arrow. A relative peak intensity ratio between the blue/left and red/right peaks demonstrates a marked shift between the native serum and the molecules harvested and subsequently eluted from the beads.

FIG. 11 demonstrates results of Sodium Dodecyl Sulfate-PolyacrylAmide Gel Electrophoresis (SDS-PAGE) analysis for native serum not exposed to a nanoporous material and molecules eluted from 17 nm pore size glass beads and 70 nm pore size glass beads.

FIG. 12 presents peptide sequencing results showing protein sequences obtained from eluents from 17 nm pore size glass beads and 70-nm pore size glass beads.

FIGS. 13 (A)-(C) compare serologic fractionation and purification enhancement using nanoporous materials (A) with classical histochemical techniques (B,C) to reveal pathologic discriminators. FIG. 13(A) demonstrates that serum exposure to nanoporous surface augments detection of certain protein peaks. FIG. 13(B): Masson's trichrome stain (right panel) demonstrates collagen deposition, necessary information for staging the patient's hepatic fibrosis related to chronic hepatitis C infection (left panel, routine H&E staining). FIG. 13 (C): Bielchowsky silver impregnation reveals neuritic plaques in Alzheimer disease brain neocortex tissue (right panel), a cardinal pathologic sign that defies detection by H&E staining (left panel).

FIG. 14 shows a morphology of the silicon oxide nanoporous film using Transmission Electron Microscopy (TEM), see details in Example 3 below.

FIGS. 15 (i)-(ii) show MALDI-TOF profiles of human plasma after incubation on specific surfaces. (i) plasma incubated with nanoporous silicon oxide chip; (ii) plasma incubated with solid silicon oxide chip. The sample analyzed was a 5 microliter aliquot of human plasma spiked with calcitonin at a concentration of 1 microgram/mL. The calcitonin peak is marked with a star(*).

FIG. 16 shows repeatability of MALDI-TOF peptide profiles obtained by using nanoporous silicon oxide chip harvesting.

FIGS. 17 (i)-(iv) show low molecular weight (LMW) harvesting of plasma spiked with human calcitonin. Four experiments on plasma spiked with decreasing calcitonin concentration are shown (zoom on the m/z window around the calcitonin peak): (i) 1000 ng/mL, (ii) 200 ng/mL, (iii) 50 ng/mL, (iv) 20 ng/mL. Incubation and MS conditions are as described in the experimental section of Example 3 below.

FIG. 18 schematically illustrates a strategy for designing a ship for enhancing a sensitivity of low molecular weight proteome (LMWP) discussed in detail in Example 4 below.

Figure 21:
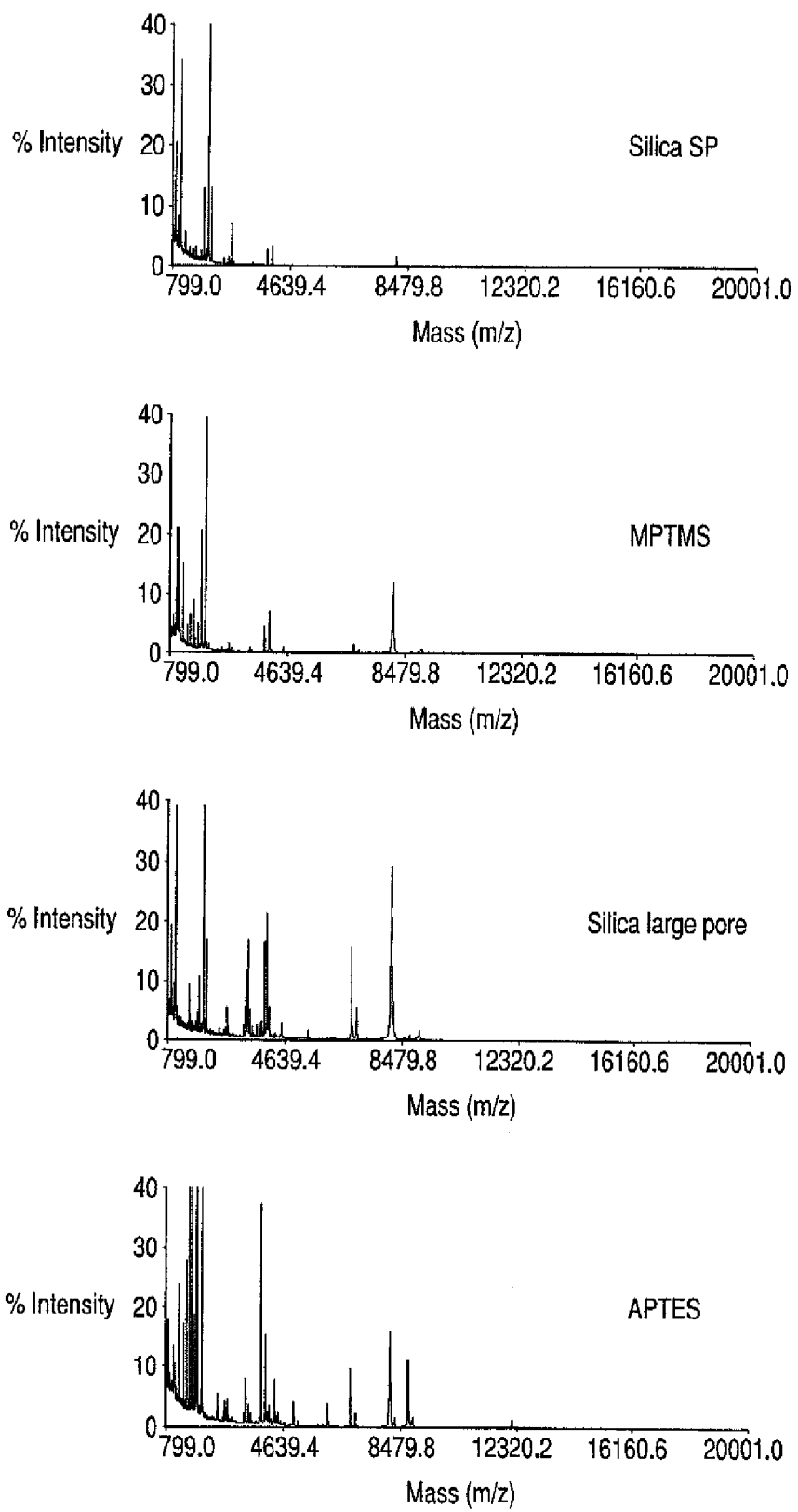

FIG. 21 shows MALDI-TOF mass spectra of mouse control serum for four different nanoporous beads. Upper left panel: silica nanoporous beads with a small pore size; upper right panel: silica nanoporous beads with a large pore size; lower left panel: small pore size silica nanoporous beads modified with 3-mercaptopropyltrimethoxysilane (MPTMS); lower right panel small pore size silica nanoporous beads modified with 3-aminopropyltriethoxysilane (APTES).

Figure 22:
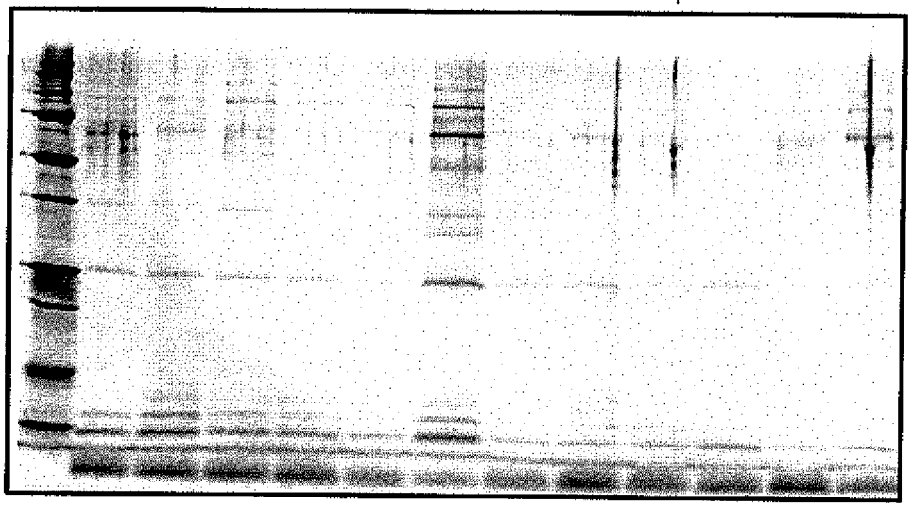

FIG. 22 presents results of 1D gel electrophoresis for small pore silica bead eluate samples. Tris-glycine gradient gel (8-16% acrylamide) of bead eluates obtained from pooled serum incubation with the small pore silica beads. The far left hand lane corresponds to the molecular weight standards, and the remaining lanes from left to right sequentially correspond to bead eluate samples 1, 7, 13, 19, 25, 31, 37, 43, 49, 55, 61, and 67 (see Table 4 in Example 5 below for a key to sample identification).

Figure 23:
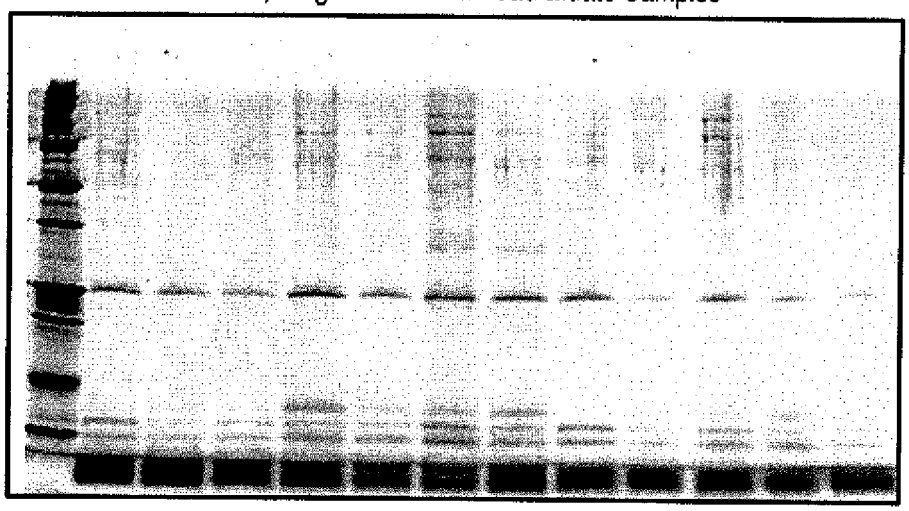

FIG. 23 presents results of 1D gel electrophoresis for large pore silica bead eluate samples. Tris-glycine gradient gel (8-16% acrylamide) of bead eluates obtained from pooled serum incubation with the large pore silica beads. The far left hand lane corresponds to the molecular weight standards, and the remaining lanes from left to right sequentially correspond to bead eluate samples 4, 10, 16, 22, 28, 34, 40, 46, 52, 58, 64, and 70 (see Table 4 in Example 5 below for a key to sample identification).

Figure 24:
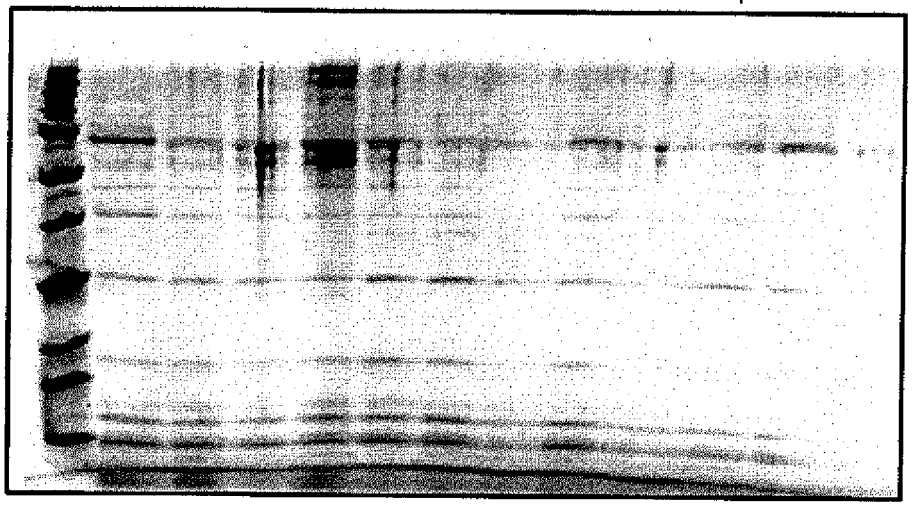

FIG. 24 presents results of 1D gel electrophoresis for small pore APTES modifies silica bead eluate samples. Tris-glycine gradient gel (8-16% acrylamide) of bead eluates obtained from pooled serum incubation with the small pore APTES modified beads. The far left hand lane corresponds to the molecular weight standards, and the remaining lanes from left to right sequentially correspond to bead eluate samples 2, 8, 14, 20, 26, 32, 38, 44, 50, 56, 62, and 68 (see Table 4 in Example 5 for a key to sample identification).

Figure 25:
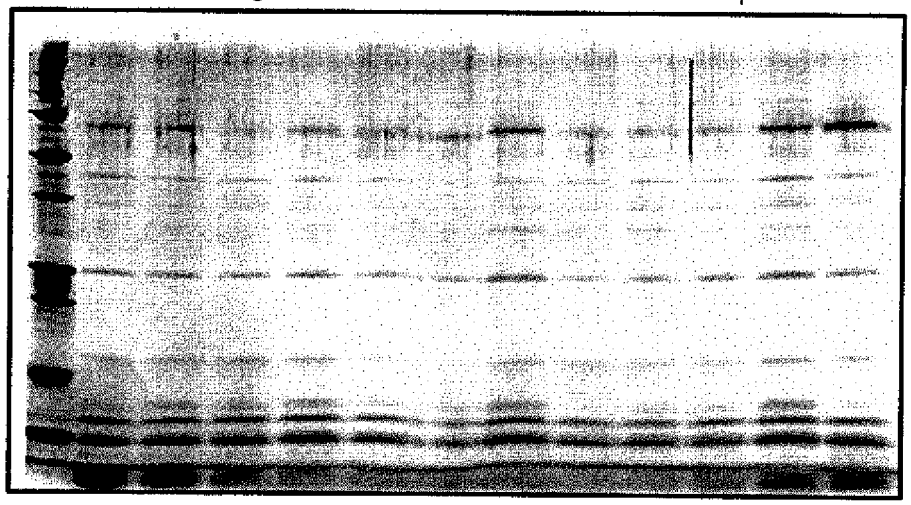

FIG. 25 presents results of 1D gel electrophoresis for large pore APTES modifies silica bead eluate samples. Tris-glycine gradient gel (8-16% acrylamide) of bead eluates obtained from pooled serum incubation with the large pore APTES modified beads. The far left hand lane corresponds to the molecular weight standards, and the remaining lanes from left to right sequentially correspond to bead eluate samples 5, 11, 17, 23, 29, 35, 41, 47, 53, 59, 65, and 71 (see Table 4 in Example 5 for a key to sample identification).

Figure 26:
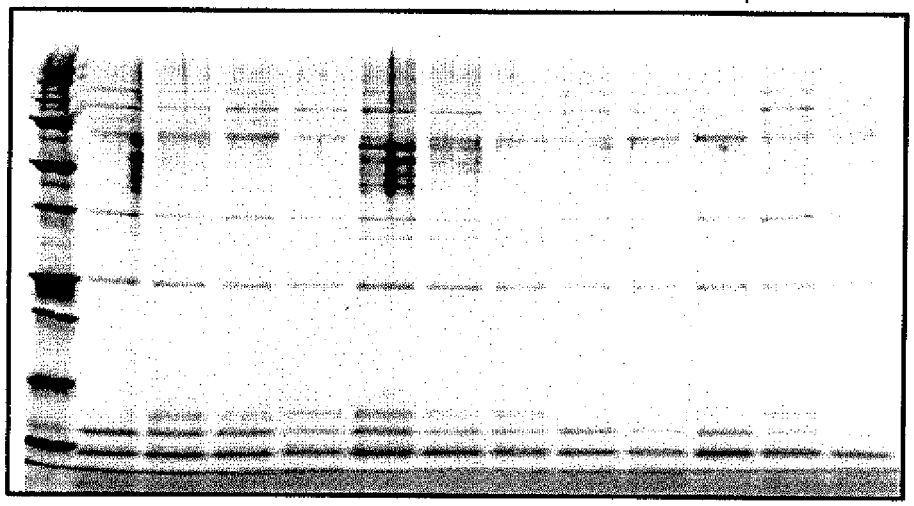

FIG. 26 presents results of 1D gel electrophoresis for small pore MPTMS modifies silica bead eluate samples. Tris-glycine gradient gel (8-16% acrylamide) of bead eluates obtained from pooled serum incubation with the small pore MPTMS modified beads. The far left hand lane corresponds to the molecular weight standards, and the remaining lanes from left to right sequentially correspond to bead eluate samples 3, 9, 15, 21, 27, 33, 39, 45, 51, 57, 63, and 69 (see Table 4 in Example 5 for a key to sample identification).

Figure 27:
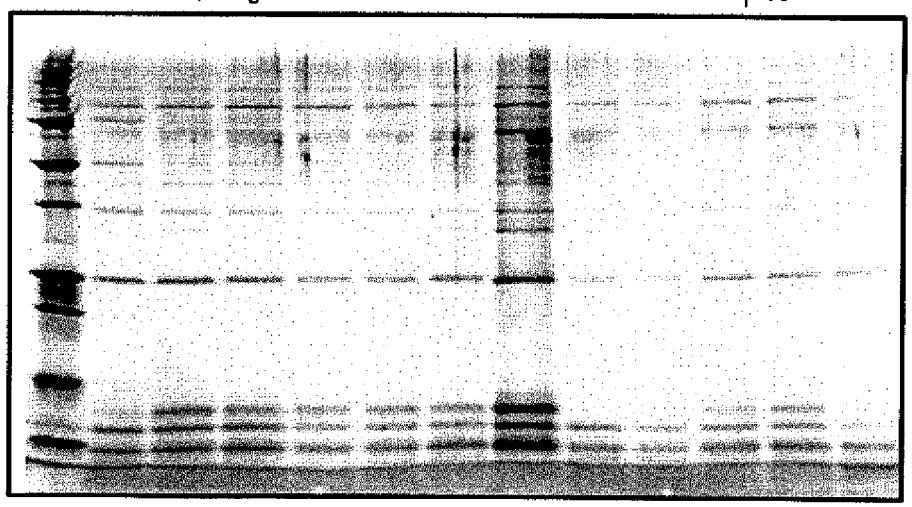

FIG. 27 presents results of 1D gel electrophoresis for large pore MPTMS modifies silica bead eluate samples. Tris-glycine gradient gel (8-16% acrylamide) of bead eluates obtained from pooled serum incubation with the large pore MPTMS modified beads. The far left hand lane corresponds to the molecular weight standards, and the remaining lanes from left to right sequentially correspond to bead eluate samples 6, 12, 18, 24, 30, 36, 42, 48, 54, 60, 66, and 72 (see Table 4 in Example 5 for key to sample identification).

Figure 28:
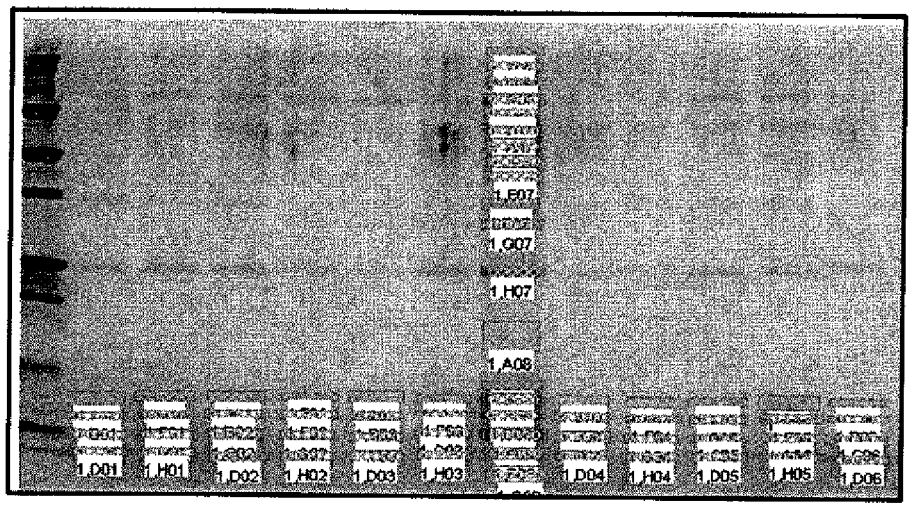

FIG. 28 presents protein band excision profile of gel in FIG. 27. Gel image is a copy of gel in FIG. 27 with an overlay of the band excision pattern used to obtain samples for tandem mass spectroscopy. Low molecular weight bands were excised from each lane, and all protein bands were excised from lane 8. Sample numbering and identification key is as follows. Bands were cut top to bottom in each lane starting from the left (lane 1 corresponds to the molecular weight markers) at lane 2, and proceeding to lane 7. Lane 8 was skipped, and band cutting continued with lane 9 through lane 13. Four bands were excised from each of these lanes. Starting with lane 2, the top band corresponds to well A1, through the bottom band, which corresponds to well D1. Bands were then cut from lane 8, starting with the top band, well E6, through the bottom band G8. Lane 2, sample wells A1-D1; lane 3, sample wells E1-H1; lane 4, sample wells A2-D2; lane 5, sample wells E2-H2; lane 6, sample wells A3-D3; lane 7, sample wells E3-H3, lane 9, sample wells A4-D4; lane 10, sample wells E4-H4; lane 11, sample wells A5-D5; lane 12, sample wells E5-H5; lane 13, sample wells A6-D6; lane 7, sample wells E6-G8.

Figure 29:
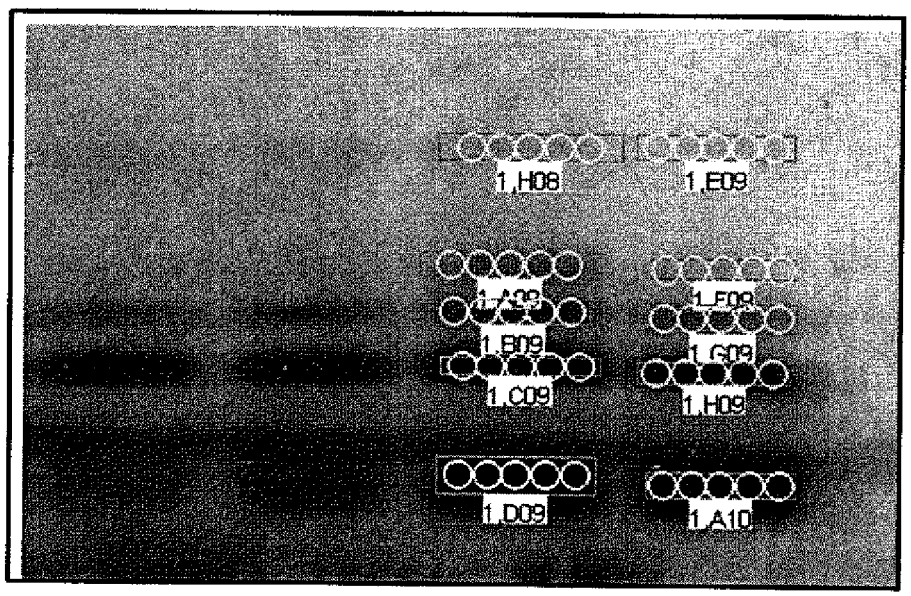

FIG. 29 presents protein band excision profile in FIG. 25. Gel image is a copy of the low molecular weight region of gel in FIG. 25, lanes 10 through 13 with an overlay of the band excision pattern used to obtain samples for tandem mass spectroscopy from lanes 12 and 13. Low molecular weight bands were excised from lane 12 and 13. Sample numbering and identification key is as follows. Bands were cut top to bottom in each lane starting from the left at lane 12, and proceeding to lane 13. Five bands were excised from each of these lanes. Starting with lane 12, the top band corresponds to sample well H8, through the bottom band, which corresponds to well D9. Bands were then cut from lane 13, starting with the top band, well E9, through the bottom band A10.

Figure 30:
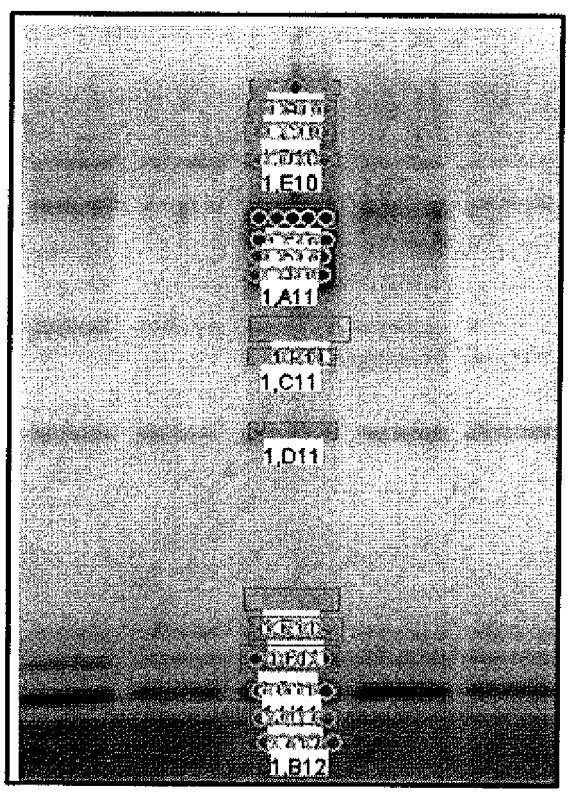

FIG. 30 presents protein band excision profile of gel in FIG. 26. Gel image is a copy of gel in FIG. 26 with an overlay of the band excision pattern used to obtain samples for tandem mass spectroscopy. All protein bands were excised from lane 6 only. Sample numbering and identification key is as follows. Bands were cut top to bottom from lane 6. A total of seventeen bands were excised from this lane. Starting at the top band, the sample corresponds to well B10, through the bottom band, which corresponds to well B12. Bands from the top of the gel correspond to sample wells B10, C10, D10, E10, F10, G10, H10, A11, B11, C11, D11, E11, F11, G11, H11, A12, and finally B12.

Figure 31:
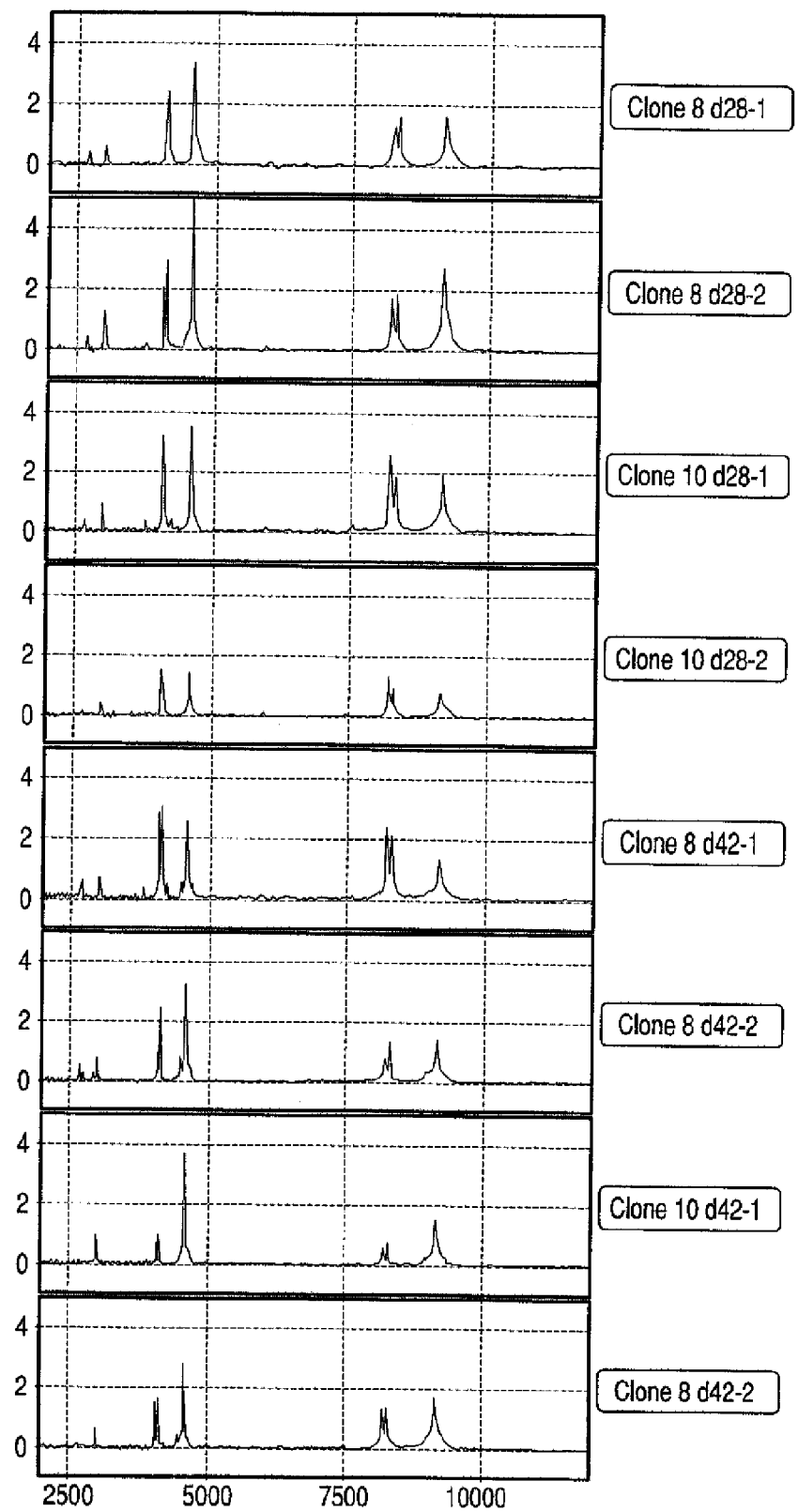

FIG. 31 presents SELDI mass spectra of pooled sera. SELDI spectra obtained from WCX2 chips of the pooled and diluted raw sera are presented. Each sample is represented in duplicate spectra. From the top: spectra 1 and 2, day 28-clone 8 sera; spectra 3 and 4, day 28-clone 10; spectra 5 and 6, day 42-clone 8; and spectra 7 and 8, day 42-clone 10.

Figure 32:
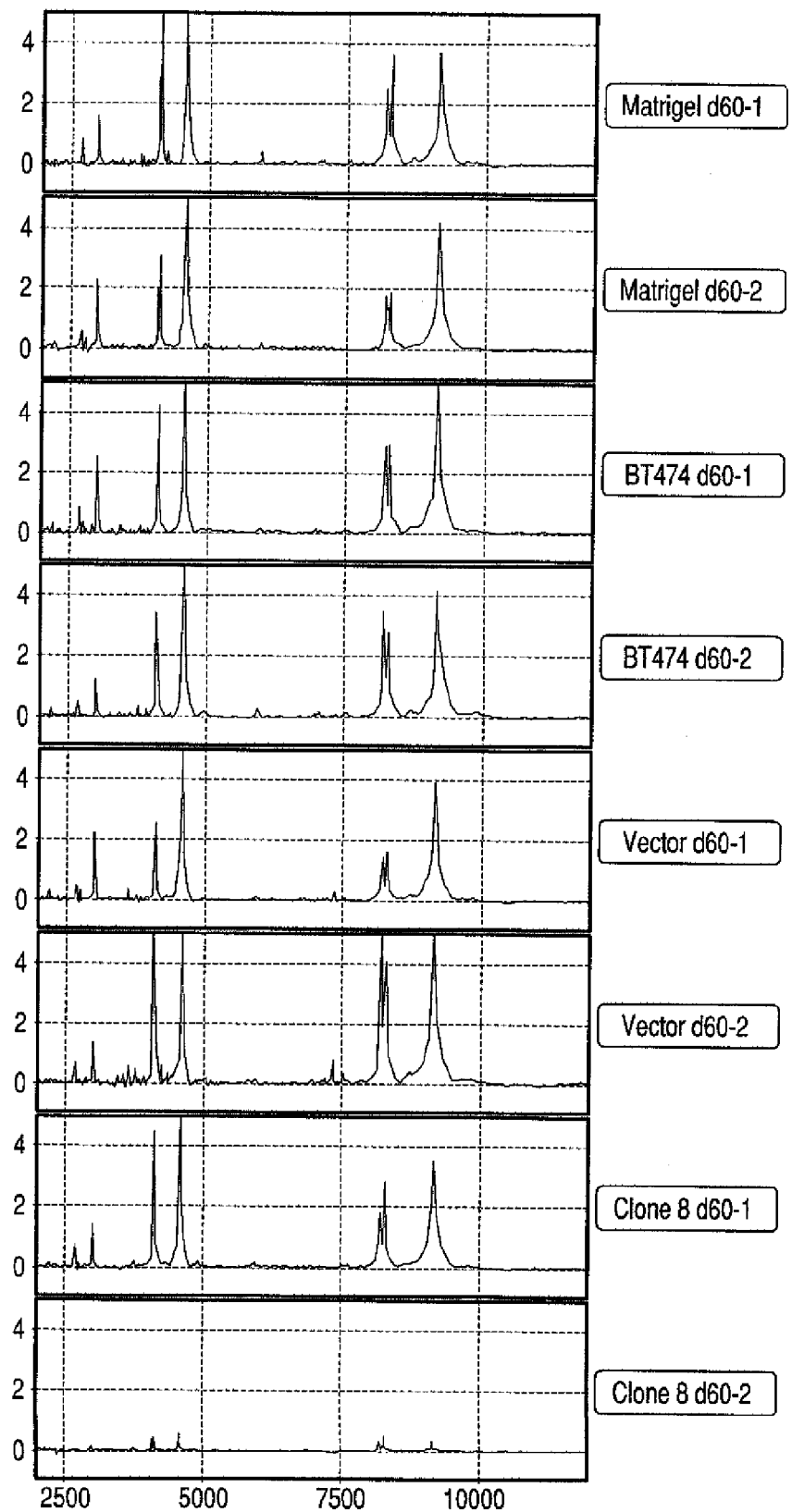

FIG. 32 presents SELDI mass spectra of pooled sera. SELDI spectra obtained from WCX2 chips of the pooled and diluted raw sera are presented. Each sample is represented in duplicate spectra. From the top: spectra 1 and 2, day 60-matrigel control sera; spectra 3 and 4, day 60-BT474 control; spectra 5 and 6, day 60-MCF7 control cell line; and spectra 7 and 8, day 60-clone 8.

Figure 33:
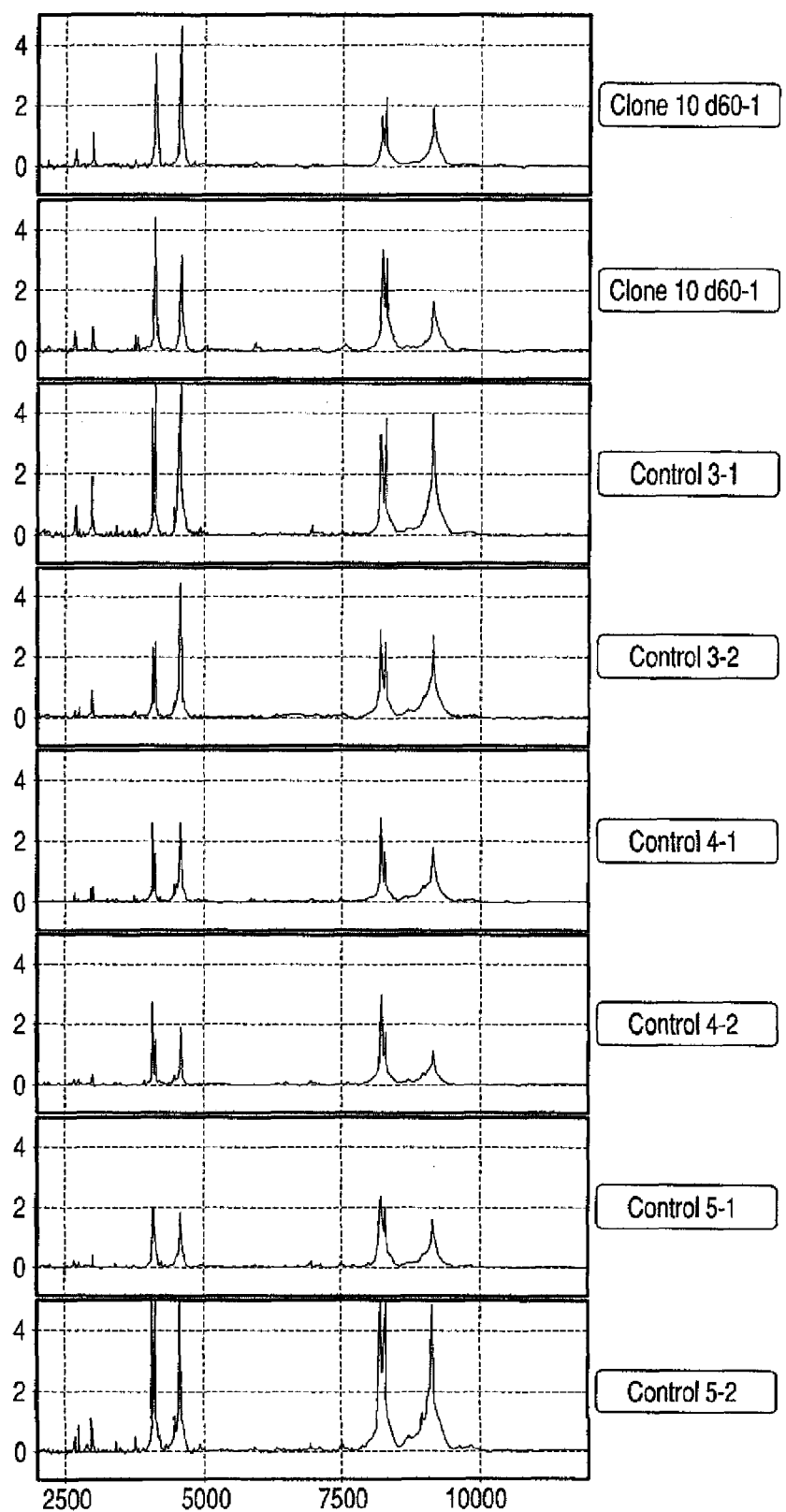

FIG. 33 presents SELDI mass spectra of pooled sera. SELDI spectra obtained from WCX2 chips of the pooled and diluted raw sera are presented. Each sample is represented in duplicate spectra. From the top: spectra 1 and 2, day 60-clone 10 sera; spectra 3 and 4, control pool A; spectra 5 and 6, control pool B; and spectra 7 and 8, control pool C.

FIGS. 34 (A)-(C) present SELDI spectra of bead eluates.
FIGS. 35 (A)-(C) present SELDI spectra of bead eluates.
FIG. 36 (A)-(C) present SELDI spectra of bead eluates.
FIG. 37 (A)-(C) present SELDI spectra of bead eluates.
FIG. 38 (A)-(C) present SELDI spectra of bead eluates.
FIG. 39 (A)-(C) present SELDI spectra of bead eluates.

DETAILED DESCRIPTION

Unless otherwise specified, the words "a" or "an" as used herein mean "one or more".

In one embodiment, the invention provides a method that involves providing a sample comprising a first component and a second component, providing a substrate comprising a nanoporous material and exposing the nanoporous material to the sample. Upon the exposure the nanoporous material retains the first component and does not retain the second component.

Preferably, the sample is a biological sample, i.e. a sample that contains biomolecules, such as proteins, peptides, antigens, antibodies, protein fragments, RNA or DNA. The biological sample can be a sample from a plant, an animal, including a mammal, preferably a human, or a cell culture. The biological sample can be a sample of a biological fluid such as blood, blood serum, blood plasma, urine, seminal fluid, seminal plasma, pleural fluid, ascites, nipple aspirate, feces or saliva.

The nanoporous material can be any material that has a pore size distribution centered at less 1000 nm, preferably less than 100 nm. In some embodiments, the nanoporous material can be a nanoporous silicon. Yet in some embodiments, the nanoporous material can be a nanoporous oxide material such as a nanoporous silica or a nanoporous alumina.

The nanoporous material can separated the first and the second component by molecular weight, i.e. the first component retained by the nanoporous material can have an average molecular weight lower than the second component.

The component retained by the nanoporous material can be adsorbed to a nanoporous material, i.e. it is a component that can be washed away by mild washing such as washing with dionized water.

The first component retained by the nanoporous material can a low molecular weight component, i.e. a component, in which all of substantially all molecules have a molecular weight no higher than 20 kDa, or no higher than 15 kDa, or no higher than 10 kDa, or no higher than 5 kDa or no higher than 4 kDa.

The nanoporous material can act a molecular cut off, i.e. the nanoporous material can retain all or substantially all the molecules having a molecular weight equal or below a molecular cut off weight and do not retain all or substantially all the molecules having a molecular weight above the molecular cut off weight. The molecular cut off weight of the nanoporous material can be varied by adjusting a pore size of the nanoporous material.

A surface of the nanoporous material can be modified, for example, with electrical charge or functional groups deposited on the surface. Such a modification can be used for retaining particular components of the sample. For example, a positive charge can be provided by modifying the surface with amino-containing molecules such as aminosilanes. A negative chare can be provided by modifying the surface with mercapto group containing molecules such as mercaptosilanes. The surface can also be modified with hydrophobic groups by depositing a long chain alkyl (longer than $C_{10}$) containing molecules, such as alkyl silanes.

The surface of the nanoporous material can be also modified with metals, such as copper or iron, which can, for example, increase an affinity of the nanoporous material to a particular component of the sample, such as phosphorylated proteins. To modify a surface of a nanoporous oxide, such as a nanoporous silica, a salt of the metal can be added during synthesis of the nanoporous oxide. For example, for nanoporous silica, different amount of $Cu(MeCO_2)2H_2O$ can be added in CTAB (cetyltrimethylammonium bromide) and TEOS (tetraethylorthosilicate) and $Na_2O$ and $H_2O$. After that, a thigh temperature treatment can be performed at around 200 degrees C. and at around 540 degree C. A surface of nanoporous silicon can be modified with a metal by using electroless plating.

The substrate comprising the nanoporous material can be provided in a variety of forms, which include, but not limited to, a film, a wafer, a particle or a microchip.

In some embodiments, the substrate can be fabricated using a top-down technique such as photolithography, electron beam lithography, X-ray lithography, deep UV lithography and nanoimprint lithography.

In some embodiment, the component of the sample retained by the nanoporous material can be extracted from the sample, for example, for further analysis or visualization.

Yet in some embodiments, further analysis or visualization can be performed on the component of the sample retained by the nanoporous material without extracting the first component.

Further analysis of the first component can be performed for example by gel electrophoresis such as SDS-PADE, by chromatography, by bioassaying technique or by mass spectrometry such as MALDI-TOF mass spectrometry, LC/MS mass spectrometry, electro spray ionization mass spectrometry, tandem mass spectrometry or SELDI mass spectrometry.

Exposing the sample to the nanoporous material prior to analysis can enhance a level of detection of the analysis. For example, upon exposure the sample to the nanoporous material, mass spectrometry can detect low molecular weight molecules present at concentration of no higher than 1000 ng/ml, or no higher than 200 ng/ml, no higher than 100 ng/ml, or no higher than 20 ng/ml, or no higher than 10 ng/ml, or nor higher than 5 ng/ml or no higher than 1 ng/ml.

Substrates comprising the nanoporous material can be also used for detecting and/or identifying a biomarker of a physiological condition, such as a disease or a stage of disease. A disease can be for example cancer, such as breast cancer.

For detecting and/or identifying a biomarker of a physiological, one can expose a sample affected by the physiological condition to a substrate comprising a nanoporous material, analyze a fraction of the sample retained by the nanoporous material and compare a result of the analysis, such as mass spectra, with a result of a similar analysis of a control sample, i.e. a sample not affected by the physiological condition.

Substrate comprising the nanoporous material can be also used for collection and/or storage of biological sample. For example, in some embodiment, a substrate comprising a nanoporous material can be a part of a kit that also includes any applicable tool for collecting a biological sample. The collected sample can be exposed to the nanoporous material and then stored for subsequent analysis or visualization.

In one embodiment, a substrate comprising the nanoporous material can be a part of an analytical system based on a specific analytical instrument. In such a case, the substrate can be specifically configured to enhance a sensitivity of the analytical instruments to one or more analytes, such as low molecular weight biomolecules.

For such an application, the substrate can have one or more areas comprising the nanoporous material. Each of such areas is surrounded by a region that is resistant to adsorbing the analytes of interest. The surrounding region is preferably a non-nanoporous region, i.e. it does not comprise a nanoporous material. The surrounding region can be pacified with functional groups resistant to adsorbing the analytes of interest. In case of peptides and proteins, the surrounding area can be modified with hydrophilic functional groups, such as PEG containing polymers.

In some embodiments, the substrate can focus or concentrate a sample to be analyzed to the one or more areas comprising the nanoporous material. Such focusing or concentration can reduce an amount of sample exposed to the analysis, which in turn can enhance a sensitivity to the analytes of interest.

In some embodiments, a size of the area comprising the nanoporous material can be made such that it matches a size of an active area of an ionization source of the analytical instrument. For example, when the analytical instrument analyses a laser for ionization, the size of the area comprising the nanoporous material can match a size (a diameter) of a beam of the laser. Such a substrate can be particularly useful for mass spectrometric analytical instruments using lasers for ionization, such as MALDI mass spectrometer or SELDI mass spectrometer.

In some embodiments, a substrate comprising a nanoporous material can be configured as a probe to be inserted in a mass spectrometer such as MALDI mass spectrometer or SELDI mass spectrometer.

The invention is further illustrated by, though in no way limited to, the following examples.

Example 1

The citations in the brackets in this example refer to the List of References at the end of Example 1.

1. Introduction

Proteomic analysis of human plasma/serum for the early detection of cancer as well as other diseases, is an increasing area of interest for many research groups [1, 2 and references therein]. Even more attention is particularly focused on the carrier protein-bound low molecular weight molecules reputed to generate and constitute the majority of the ions that comprise distinctive MS profiles used for biomarkers discovery [3-5]. The design and the development of particles engineered to mimic carrier protein (e.g. albumin) binding and perform low molecular weight proteome (LMWP) harvesting, can therefore be of high impact in biomarker discovery [6-8]. ProteinChip Array System from Ciphergen, based on SELDI-TOF mass spectrometry, can be the most extensively used platform for the discovery of "molecular signatures" [9, 10]. Among recent technologic advances in this field, promising emerging approaches include: a new peptidomics platform that couples magnetics-based, automated solid-phase extraction of small peptides with MALDI-TOF mass spectrometric readout [11, 12], Desorption/Ionization on Silicon (DIOS) modified surfaces [1,3] and Desorption/Ionization on Silicon Nanowires (SiNWs) [1,4]. For proteomic-based biomarkers discovery, nanotechnology can offer opportunities and challenges [1,5]. To translate a potential of nanotechnology to proteomics, an application of nanoporous silica to sieve plasma proteins with the goal to more effectively and efficiently harvest plasma LMWP has been studied.

A matrix assisted laser desorption ionization-time of flight (MALDI-TOF) mass spectrometry analysis of plasma proteins extracted from two different nanoporous silica surfaces has been performed. Obtained mass spectra demonstrate the ability of nano-sized silica particles to retain hundreds of peptides and low molecular weight proteins.

2. Materials and Methods

2.1 Materials and Instruments

Reagents for gel synthesis included sodium silicate solution (Sigma, St. Louis, Mo., USA), fumed silica (Sigma-Aldrich, St. Louis, Mo., USA), polyoxyethylene(10) isononylphenylether (Nonfix10, Condea, Houston, Tex., USA), and cetyltrimethylammonium bromide (CTABr, Aldrich, St. Louis, Mo., USA). MALDI matrix α-cyano-4-hydroxycinnamic acid (CHCA) was obtained from Sigma (St. Louis, Mo., USA). Protease inhibitor cocktail (PIC: lithium heparin, EDTA, AEBSF, bestatin, E-64, leupeptin and aprotinin) was purchased from Sigma (St. Louis, Mo., USA). Insulin from Bovine Pancreas was obtained from Sigma (St. Louis, Mo., USA).

All samples were analyzed with an Applied Biosystems Voyager-DE™ STR mass spectrometer (Framingham, Mass., USA) using 337-nm light from a nitrogen laser. Analyses were performed in linear mode.

2.2 Synthesis Procedure

Silica samples A and B were obtained according to two distinct synthesis procedures described, for example, in [16, 17]. Briefly, silica samples A and B were obtained starting from gels with the following molar compositions: Silica A $SiO_2$: 0.064Nonfix10: 0.6NaOH: 0.8HCl: $58H_2O$; Silica B: $SiO_2$: 0.2CTABr: 0.2NaOH: $0.04Al(OH)_3$: $40H_2O$.

For silica A, 14.6 g of sodium silicate was added after complete dissolution of surfactant solution (2.9 g Nonfix 10 and 4.05 g NaOH in 57.4 g $H_2O$). Finally, 5.33 g of 37 wt % HCl was added, and the gel was aged for 24 h at room temperature, and then heated in oven for 24 h at 100° C.

Silica B was obtained by adding 10 g of fumed silica to a solution consisting of 0.52 g of $Al(OH)_3$ and 1.35 g of NaOH in 130 g of $H_2O$. The gel was aged for 2 h at room temperature and then heated in oven for 24 h at 140° C. The synthesis gel was filtered, washed with deionized water and dried at 80° C. for 12 h.

The nitrogen adsorption desorption volumetric isothems at 77 K were measured on a Micrometritics Asap 2010 apparatus. Samples were baked at 300□ in vacuum overnight, and benziylated samples were treated at 230° C. to the same residual pressure. Surface area of the samples was obtained by Brunauer-Emmet and Teller (BET) linearization in the pressure range 0.005 to $0.2p/P_0$ [16].

2.3 Plasma Collection

Human plasma was obtained according to the guidelines suggested in [18]. Briefly, blood was collected in 8.0 mL lithium heparin plasma separating tubes (PST Vacutainer® 367965, Becton Dickinson, Franklin Lakes, N.J., USA) preloaded with 300 μL of PIC and centrifuged at 2500 g for 15 min at 4° C. within 15 min of the draw. Aliquotes of the plasma layer were made within 30 min of centrifugation in 1.0 mL volumes and immediately frozen using a dry ice/alcohol bath.

2.4 Experimental Procedure

Aliquots (5 mg) of silica particles were mixed with 500 μL of a human plasma diluted sample (1:5) and shaken at room temperature for one hour. The suspension was centrifuged at 2000×g, for two minutes, then the silica particles were separated from the supernatant and washed with deionized water (4×100 μL). Plasma proteins retained on silica surface were extracted as follow: silica particles were suspended in 100 μL of a solution (4.95:4.95:0.1 water/methanol/0.1% TFA) and immediately centrifuged at 2000×g, for five minutes. The supernatant solution with extracted proteins was analysed by MALDI-TOF-MS. 1 μL of supernatant was combined with 4 μL of CHCA matrix, then 1 μL of the obtained solution was spotted on MALDI plate and air-dried.

2.5 Spiking Experiments

Plasma samples were spiked with insulin at four different concentration: 500 ng/mL, 200 ng/mL, 30 ng/mL and 15 ng/mL. The samples were after exposed to silica A as described in section 2.3. Finally 5 μL of plasma extracted proteins were eluted in 3 μL of CHCA matrix, then 1 μL of the obtained solution was spotted on MALDI plate and air-dried.

3-4 Results and Discussion

In this study, an ability of novel nanoporous silica particles to capture and enrich low molecular weight peptides and proteins from human plasma was studied. This archive is now postulated to contain an untapped reservoir for potential disease-specific biomarkers [3-5]. An efficient way of rapidly sequestering and enriching for this information archive can have a dramatic impact on biomarker discovery.

FIG. 1 shows a morphology of silica A and B. A nitrogen adsorption-desorption isotherm suggests that the surface area of silica A is 406 $m^2$/g and pore volume is 0.3 $cm^3$/g. The Barret-Joyner-Halenda (BJH) model applied to the desorption branch of the isotherms demonstrates a bimodality of the porous system indicating a pore size distribution centered at 26.8 and 38 Å. For silica B, the surface area is 848 $m^2$/g and pore volume is 1.21 $cm^3$/g. The BJH pore size distribution is centered at 25 and 390 Å.

Exploratory experiments were designed in order to evaluate capturing ability of nanoporous silica towards plasma proteins and particularly towards low molecular weight proteome proteins. A rapid and easy procedure for sample preconcentration prior to MS based analysis was developed, which allowed minimizing potential degradation of the biological sample. Compared to an untreated sample, mass spectra of human plasma samples treated with silica particles, display a clearly visible enrichment in the LMWP, which depends on particular nanoporous silica substrate used, see FIG. 2.

Figure 3:
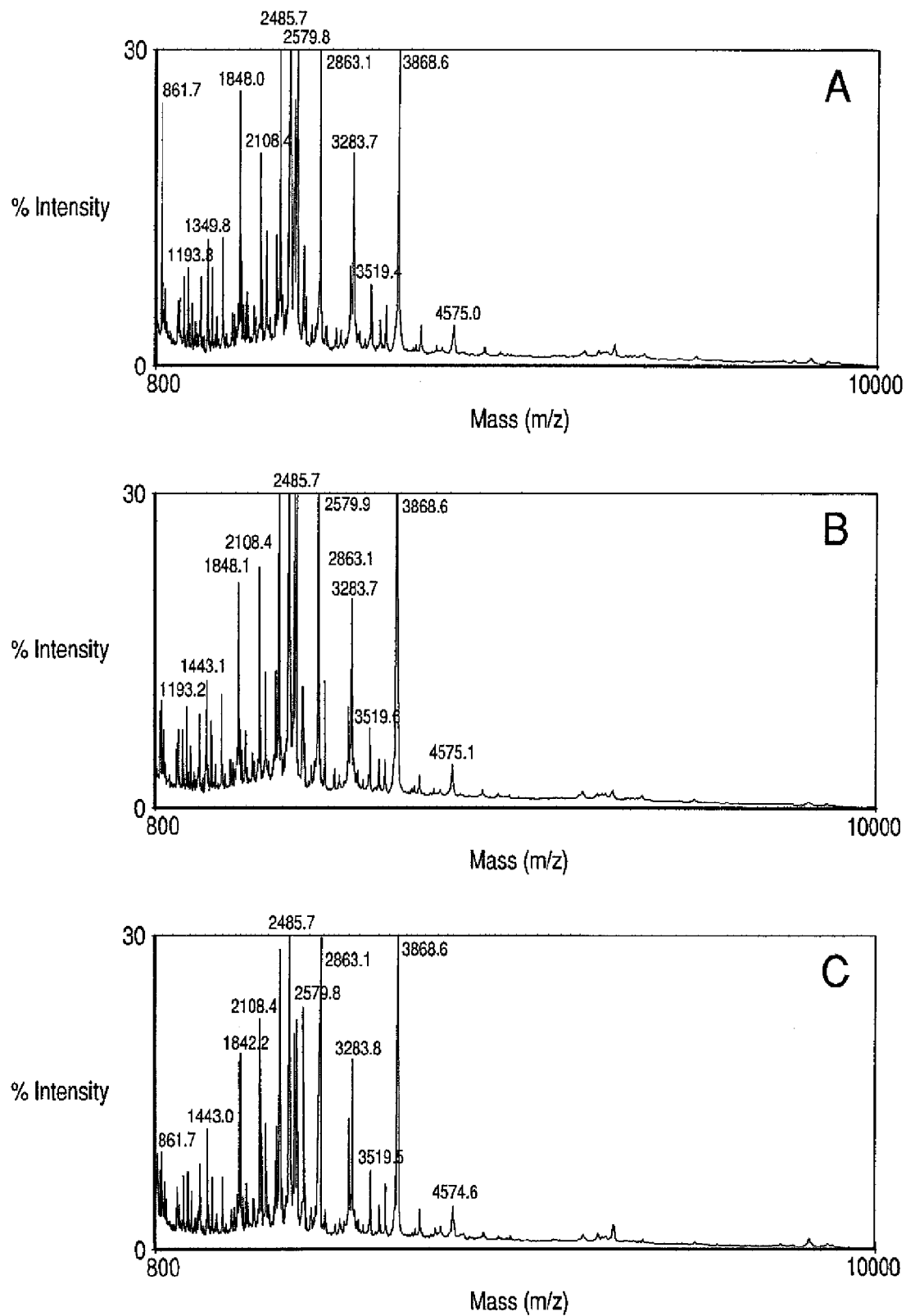
Figure 4:
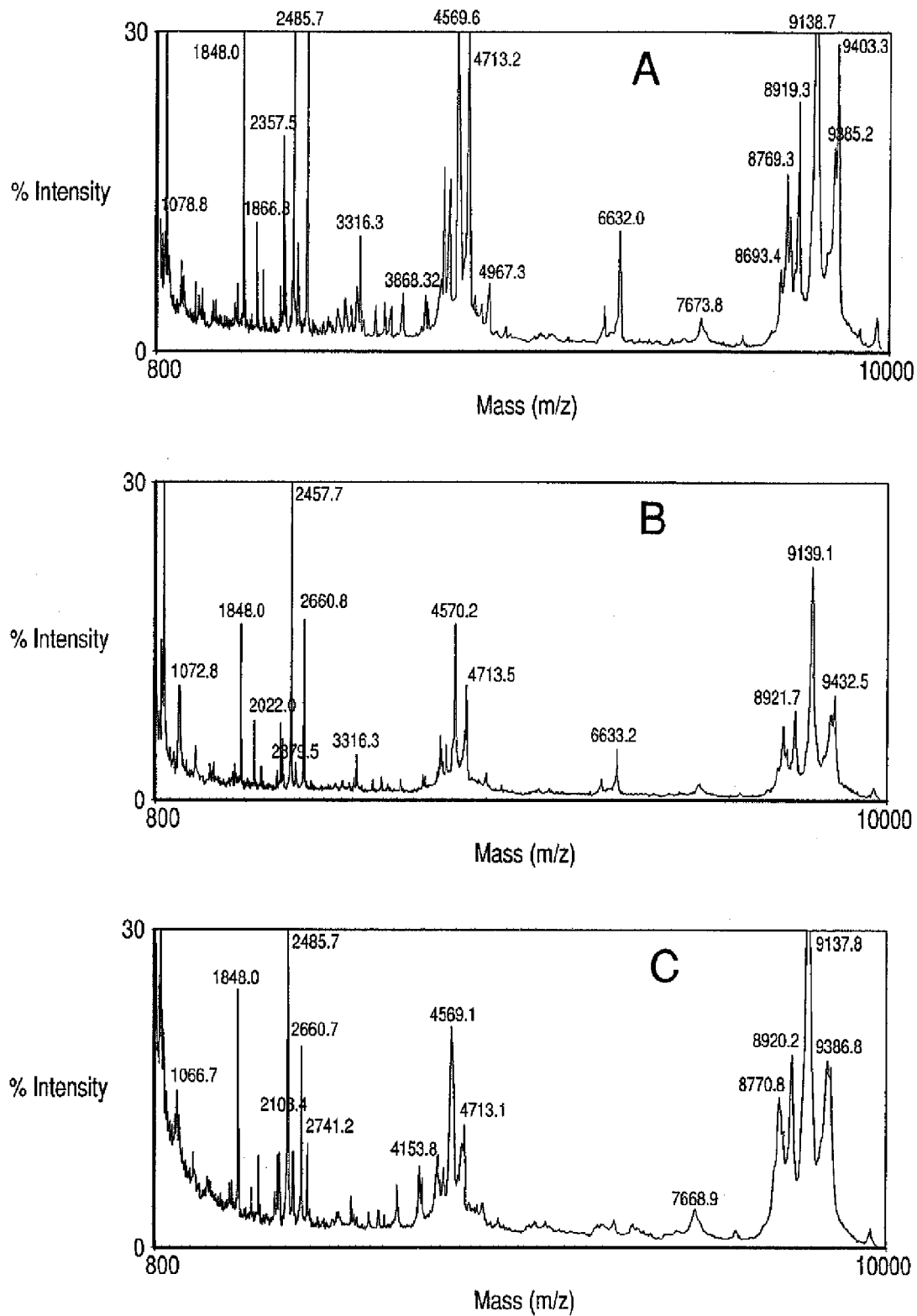

MALDI-TOF spectra of both samples treated with nanoporous silica reveal hundreds of peaks, especially in the LMW range between 800 and 5000 Daltons. For each batch of silica, the experiments were performed in triplicate to assess reproducibility of the assay. The data indicate that the method generates reproducible overall spectral portraits of high intensity signals (see FIGS. 3 A-B-C and FIGS. 4 A-B-C). A high quality of the spectra may be a product of the cleanup procedure. Washing silica substrate (before extraction of captured proteins) can remove salts, nonvolatile and hydrophilic contaminants that can potentially cause severe signal suppression. An ability to effectively generate a reproducible profile of the molecules retained by the silica particles (FIGS. 3 and 4), may also arise from an inherent chemical stability of silica substrates [16,17].

Figure 5:
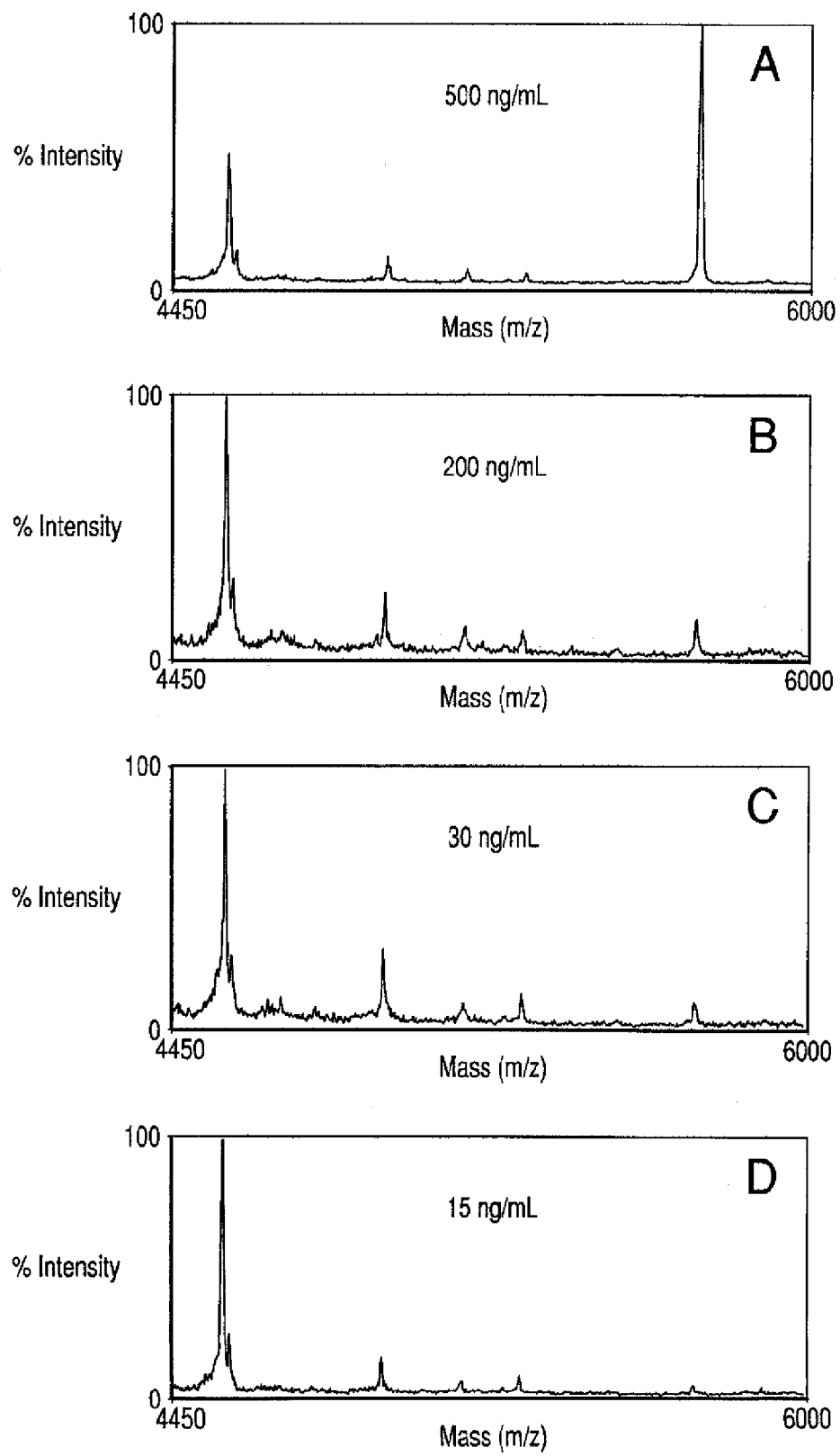

Spiking of plasma samples with insulin (molecular mass 5733.5 Da) at different concentration was performed to establish a limit of detection (LOD) of the method described here. A MALDI-TOF signal of insulin in human plasma with concentrations as low as 15 ng/mL was detected (FIG. 5).

The present approach coupled with MALDI-TOF technology is sensitive enough to detect plasma peptides in the low-nanogram per milliliter range. Considering that to date the lowest concentration for a biomarker, such as Haptoglobin-$\alpha$ subunit, identified by MS is 1000 nmol/L [22, 23], the present LMWP plasma enriching approach lowered the LOD of roughly 400-fold.

Figure 2:
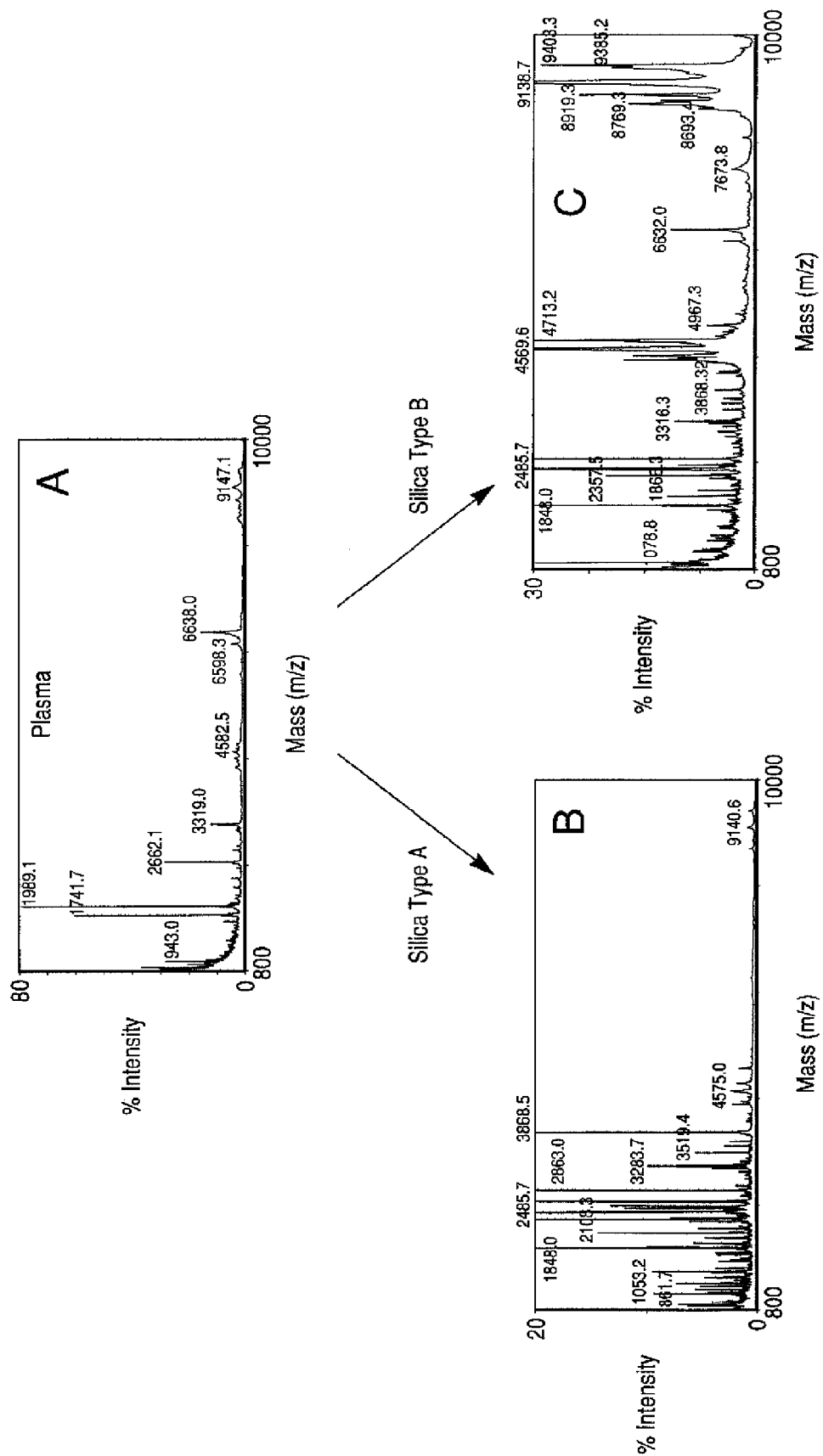

Based on the MS profiles, each of the two silica substrates with different pore size retains a different repertoire of peptide/proteins upon incubation with the same sample of plasma (see FIG. 2). Although the present invention is not limited by its theory of operation, it can be hypothesized that the differences observed are underpinned by substratum surface property and the propensity for adsorption of the proteins onto the hydrophilic surface through electrostatic interactions. LMWP binding can be improved by tailoring surface properties of silica substrate through additional chemical and structural modifications.

5. Concluding Remarks

It was demonstrated that nanoporous silica particles can be successfully employed to act as a carrier protein-like entity and enrich for low molecular weight molecules within plasma/serum or other biological fluids. The results demonstrate potential selectivity of the molecules and the molecular discriminatory properties of nanoporous silica particles that selectively bind LMWP. Therefore, these novel substrates coupled with mass spectrometry surface can provide both a means of rapidly sequencing the biomarker component itself as well as a potential platform for LMWP-based predictive medicine.

6. List of References

[1] Anderson, N. L., Mol. Cell. Proteomics 2005, October 2005; 4: 1441-1444.
[2] Xiao, Z., Prieto D., Conrads, T. P., Veenstra, T. D., Issaq, H. J., Mol. Cell. Endocrinol. 2005, 230, 95-106.
[3] Liotta, L. A., Ferrari, M., Petricoin, E., Nature 2003, 425, 905.
[4] Mehta, A. I., Ross, S., Lowenthal, M., Fusaro et al., Dis. Markers 2003, 19, 1.
[5] Tirumalai, R. S., Chan, K. C., Prieto, D. A., Issaq, H. J. et al., Mol. Cell. Proteomics 2003, 2, 1096-1103.
[6] Geho, D. H., Lahar, N., Ferrari, M., Petricoin, E. F., Liotta, L. A., Biomed. Microdevices 2004, 6, 231-239.
[7] Desai, T., Hansford, D., Kulinsky, L., Nashat, A. H. et al., Biomed. Microdevices 1999, 2, 11-40.
[8] Desai, T., Hansford, D., Leoni, L., Essenpreis, M., Ferrari, M., Biosensors and Bioelectronics 2000, 15, 453-462.
[9] Hutchens, T. W., Yip, T. T., Rapid Commun. Mass. Spectrom. 1993, 7, 576-580.
[10] Reddy G., Dalmasso, E. A., J. Biomed. Biotechnol. 2003, 4, 237-241.
[11] Villanueva, J., Philip, J., Entenberg, D., Chaparro, C. A. et al., Anal. Chem. 2004, 76, 1560-1570.
[12] Villanueva, J., Philip, J., Chaparro, C. A., Li, Y. et al., J. Proteome Res. 2005, 4(4); 1060-1072.
[13] Trauger, S. A., Go, E. P., Shen, Z., Apon, J. V. et al., Anal. Chem. 2004, 76, 4484-4489.
[14] Go, E. P., Apon, J. V., Luo, G., Saghatelian, A. et al., Anal. Chem., 2005, 77, 1641-1646.
[15] Ferrari, M., Nat. Rew. Cancer 2005, 5, 161-171.
[16] Pasqua, L., Testa, F., Aiello, R., Nagy, J. B., Madeo, G., Phys. Chem. Chem. Phys 2003, 5, 640-645.
[17] Pasqua, L., Testa, F., Aiello, R., Stud. Surf. Sci. Catal. 2003, 146, 497.
[18] Hulmes, J. D., Bethea, D., Ho, K., Huang, S. P. et al, Clinical Proteomics Journal, 2004, 1, 17-31.
[19] Diamandis E. P., J. Natl. Cancer Inst. 2004; 96:353-6.
[20] Diamandis, E. P., Mol. Cell. Proteomics 2004, 3, 367-78.
[21] Diamandis, E. P., Clin. Cancer Res. 2005, 11, 963-965.
[22] Koomen, J. M., Shih, L. N., Coombes, K. R., Li, D. et al., Clin Cancer Res. 2005, 11, 1110-1118.
[23] Ye, B., Cramer, D. W., Skates, S. J., Gygi S. P. et al, Clin. Cancer Res. 2003, 9, 2904-2911.

Example 2

Fractionation of Serum Components Using Nanoporous Substrates

Numerous previously uncharacterized molecules residing within a low molecular weight circulatory proteome may provide an ongoing picture of the ongoing pathophysiology of an organism. Recently, proteomic signatures comprising low molecular weight molecules have been identified using mass spectrometry combined with bioinformatics algorithms. These demonstrations have pointed to an existence of an information archive that may contain a rich source of diagnostic information. Attempts to sequence and identify the molecules that underpin the fingerprints are currently underway. A finding that many of such low molecular weight molecules may exist bound to circulating carrier proteins may afford a new opportunity for fractionation and separation techniques prior to mass spectrometry based analysis. Nanoporous substrates represent a new approach for the facile and reproducible fractionation and selective binding of the low molecular weight biomarker material. Aminopropyl-coated nanoporous silicon, when exposed to serum, can deplete serum of proteins and yield a serum with a distinct, altered MS profile. Additionally, aminopropyl-coated nanoporous glass beads with controlled pore size are able to bind a subset of serum proteins and release them with stringent elution. The eluted proteins have distinct MS profiles, gel electrophoresis profiles, and differential peptide sequence identities, which vary based on a size of nanopores. Two potential biomarkers for ovarian cancer, transthyretin and apolipoprotein A-1, were differentially sequestered based on pore size of the beads. Systematic use of this novel serum fractionation strategy, when coupled with bioinformatic analysis, can increase access to a diagnostic information, analogous to a pathologist's use of myriad histochemical stains during evaluation of diseased tissues. The nanoporous material surfaces can be employed in a harvesting and preservation of labile and carrier-protein bound molecules in the blood. Moreover, knowledge gained from such studies with nanoporous substrates can contribute to using infusible nano-harvesting agents that could monitor a circulation for early-stage disease-related signatures.

Introduction

At its core, pathology is a medical specialty built upon careful systematic observation of disease signs, discovered through meticulous comparisons of normal and diseased tissue variants. The ancestral state of the art of pathologic diagnosis, known to every medical student, was a recognition upon physical examination of the four cardinal signs of underlying tissue pathology: tumor, dolor, calor, and rubor. Likewise, initial examination of tissues may begin with visual and tactile observation. However, this is just a start of a modern assessment of tissues for full pathologic evaluation. Since an introduction of a microscope and laboratory methods birthed modern medical pathology practice, technologic advancement has unveiled increasingly sensitive and insightful views of disease processes. Through modern clinical laboratory tests and tissue processing, a vast array of tests provide a contemporary pathologist with tools to provide meaningful diagnoses for physicians who have consulted them. With all such tests, an ability to appreciate and interpret signs and patterns of signs is at the center of a pathologist's craft. A correlation of certain histological patterns, such as a given tissue's differential uptake of hematoxylin and eosin (H&E), with a particular disease states and prognostic outcomes is a continually evolving process that underlies a pathologic consultation. Tissue histochemical methods can be considered as tissue fractionation methods for different dyes, antibodies, probes, etc. However, the tissue histochemical methods only reveal selective tissue subcomponents, allowing other subcomponents to escape detection.

Following a rich tradition of pathology's constant integration of new technologies into its practice, modern pathology is evaluating an applicability of novel testing platforms into patient-based diagnostics. For one, new, more sensitive mass spectrometry instruments are used to mine patient body fluid and tissue samples for potential diagnostic signatures (Rosenblatt et al., 2004, see reference list at the end of Example 2). Such efforts are part of a new discipline, namely tissue proteomics, wherein measurements of a multiplexed combination of molecules within the patient tissues are generated and correlated with disease states and outcomes. Because of a potential increase in both specificity and sensitivity using a combination marker approach, it may be possible to detect and catch a lethal disease early, before it manifests itself as a tumor, dolor, calor, or rubor.

Proteomic fingerprinting methods utilizing mass spectrometry coupled to bioinformatics analysis, has yielded clues about an existence of potential diagnostic information content within the low molecular weight range of blood and tissue proteome (Chaurand and Caprioli, 2002; Hingorani et al., 2003; Paweletz et al., 2000; Petricoin et al., 2002a; Petricoin et al., 2002b; Schwartz et al., 2004; Stoeckli et al., 2001; Yanagisawa et al., 2003). Now that such an information archive has been implicated by these studies, efforts are underway to sequence and characterize underlying components of disease-related fingerprints.

Molecules that coalesce to form a diagnostic portrait can be diverse small proteins, and protein fragments, shed by numerous tissues into an interstitial fluid with an equilibrium established with an intravascular compartment. A constant synthesis and degradation of proteins by cells within a body may reflect an overall state of health. The expressed proteome within a host may represent a complex interplay between all cells (normal and diseased cells) and thus body fluids, such as serum, may be a rich source of information for a discovery of biomarkers of disease and a development of diagnostic tests. Recent work indicates that low molecular molecules carrying disease fingerprints are bound to larger carrier molecules (Mehta et al., 2003). Thus, an isolation of such low molecular weight molecules as well as of the resident carrier proteins that harbor them and protect them from a renal clearance is an object in MS-based tissue proteomics for discovery and sequencing of new biomarkers.

A more comprehensive and expansive analysis of the low molecular weight proteome bound to carrier proteins may require a development of novel fractionation methods, which can reveal potentially useful diagnostic information not available using current modalities. Fabrication of nanoporous material surfaces may be one strategy for methodically parsing the various subsets of proteins and protein fragments present within the circulation. The nanoporous materials have an ability to be modified and functionally manipulated through a specific chemical derivitization such that selective and custom binding and fractionation can ensue. Moreover, nanoporosity dramatically increases a surface area such that a selective fractionation and binding can occur with potentially higher efficiency and speed. Selective fractionation methods and materials can contribute to a field of tissue proteomics in a manner akin to innovations made by clinical chemists in creating arsenals of tissue fixatives and histochemical reagents used daily by pathology laboratories around the world.

In this Example, the use of nanoporous material surfaces as a fractionation tool for serum based analysis and biomarker discovery is demonstrated. In one experiment, a nanoporous silicon wafer is used to selectively deplete serum of high abundance proteins. Another method uses nanoporous controlled-pore glass beads to harvest distinct proteomic profiles from serum for subsequent elution and evaluation.

Material and Methods.

Serum Samples.

The serum sample is a single pool from normal donors that was stored at −80 degrees C.

Chemicals.

Chemicals: acetonitrile (ACN) (HPLC grade), ammonium bicarbonate ($NH_4HCO_3$), iodoacetamide (97%), methanol (99+%) and dithiothreitol (DTT) were purchased from Sigma-Aldrich Co. (St. Louis, Mo.). Formic acid (88%), acetic acid (glacial) purchased from Mallinckrodt Baker (Phillipsburg, N.J.). $H_2O$ was doubly distilled in house with Kontes High Purity Water System. Porcine sequencing grade modified trypsin was purchased from Promega (Madison, Wis.).

Other materials: Bovine serum albumin purchased from Sigma-Aldrich Co, St. Louis, Mo. SYPRO® Ruby protein gel stain purchased from Molecular Probes, Eugene, Oreg. Precast 4-12% Bis-tris 1D gels, LDS sample and running buffers, antioxidant, and prestained Benchmark protein ladder were purchased from Invitrogen Co. Fused silica is from Polymicro Technologies Phoenix, Ariz.

Nanoporous Silicon Wafer Fabrication.

Boron-doped, (100) oriented silicon wafers from Silicon Quest, Inc. with resistivity <0.005 ohm-cm were used as substrates. Wafers were cleaned in a piranha solution ($H_2SO_4$: $H_2O$=1:1) at 120° for 30 minutes, followed by oxide removal in HF: $H_2O$=1:10 and rinsing in deionized water. Porous silicon surfaces were prepared by electrochemical etching in a homemade Teflon cell. The wafers sit on the Teflon cell's base with aluminum foil (0.1 mm thick) underneath to provide an electrical contact. A platinum mesh was positioned in the cell's cavity as a counter electrode. An electrolyte was a 1:1 mixture by volume of 49% HF and ethanol. A constant current density 72 mA/cm$^2$ was applied for 65 sec. Immediately after porous silicon formation, the sample was rinsed in deionized water and place under vacuum to remove the moisture. The porous silicon was silanised in 10% APTES (aminopropyltriethoxy silane) in toluene. To remove air bubbles from the nanopores, the porous silicon was placed under vacuum for 3 minutes. The reaction solution was refluxed for 3 hours at a room temperature in a sealed dish. The porous silicon was rinsed several times with toluene, acetone, and dried in $N_2$ flow. The Barret-Joyner-Halenda (BJH) model applied to the nitrogen desorption branch of the isotherms indicated a pore size distribution centered at 2-20 nm.

Partial Depletion of Serum Using a Nanoporous Silicon Wafer.

Aminopropyl-coated nanoporous silicon wafers were placed in 1.5 ml tubes and washed 4 times in deionized water. 500 µl of pooled serum samples, diluted 1:5 in deionized water, were then applied to the wafers and the mixtures incubated at a room temperature for 1.5 hr. Following the incubation, the diluted serum supernatants were removed and stored for later MS analysis at −80 degrees C. For controls, diluted serum samples were frozen as well. As a further control, the wafers were also incubated with deionized water in place of diluted serum.

Proteomic Harvesting Using Nanoporous Controlled-Pore Glass Beads.

Aminopropyl-coated controlled pore glass beads, with pore sizes of 70 nm or 17 nm, were purchased from Sigma, St. Louis, Mo. Nitrogen adsorption-desorption isotherm data indicate that a surface area for 17 nm beads is 30.8 m$^2$/g and a pore volume is 0.032 cm$^3$/g. For 70 nm beads, a surface area is 130.5 m$^2$/g and a pore volume is 0.93 cm$^3$/g.

For each experiment, 10 mg of beads were measured into 1.5 ml tubes. The beads were washed 4 times in a deionized water. Pooled serum, diluted 1:5 in a deionized water, was then applied to the bead samples and the mixtures incubated at a room temperature for 1.5 hr. Following the incubation, the diluted serum supernatants were removed and saved. The beads were then washed two times using 1 ml of deionized water. Following the wash, 500 µl of elution buffer (5 ml of acetonitrile, 5 ml water, 10 µl of trifluoracetic acid) was applied to the samples, which were then rotated for ½ hr at a room temperature. The eluant was then collected and stored for later MS analysis at −80 degrees C.

Mass Spectrometry.

Low resolution mass spectrometry generated spectral profiles were used as a generalized unbiased readout to assess fractionation performance. Weak cation exchange Surface Enhanced Laser Desorption Ionization (SELDI) chips were processed using a Biomek 2000 bioprocesser (WCX2 ProteinChip®, Ciphergen Biosystems, Inc.). 100 µl of 10 mM HCl was applied to the chip followed by a 5-minute incubation. The HCl was then removed via aspiration and was followed by a 1-minute incubation with 100 µl of water. The water was aspirated and fresh water applied for an additional minute. This was followed by an addition of 100 µl of 10 mM ammonium acetate with 0.1% Triton X, applied to the chip for a 5 minute incubation. The ammonium acetate mixture was then aspirated and discarded followed by another application of the ammonium acetate mixture for an additional 5-minute incubation. After these preparative steps, the chips were dried using vacuum. 5 µl of a sample, such as serum, were then applied to the chip spots and incubated for 55 minutes. The chips were washed 3 times with 150 µl of phosphate buffered saline followed by 150 µl of water. The chips were then vacuum dried and 1.0 µl of a 30% solution of cinnaminic acid in 50% (v/v) acetonitrile, 0.5% trifluoroacetic acid was applied to each protein spot, twice with drying between applications. The chips were then assayed using a PBS-II mass spectrometer (Ciphergen Biosystems, Inc.). A spectrum for each spot was collected using the following settings: detector voltage was 1,800 V; focus mass was 6,000 Da; the hi mass limit was 20,000 Da; the sensitivity gain was set to 5; the laser intensity was 145; 15 laser shots were taken per position; the number of positions ranged from 20 to 80 incrementing every 5 positions. A protocol was created to process all of the samples identically.

Protein Sequencing Studies.

Protein Assay Bead fractionated samples from 17 nm and 70 nm-pore beads were assayed by a traditional Bradford assay using bovine serum albumin (BSA) standard ranging from 200 µg/mL to 1 mg/mL monitored at 595 nm on a UV-VIS spectrophotometer (Spectramax® Plus 384, Molecular Devices).

1D gel separation and digestion: 15 g of each bead fractionated sample and 3 µL of raw serum were diluted in 30 µL of LDS sample buffer and boiled for 5 minutes at 95° C. The fractions were run on a 1D pre-cast gel (4-12% Bis-tris) to isolate desired molecular weight regions of the complex protein mixture. The gel was washed thoroughly with dd$H_2O$, fixed in a 50% methanol/10% acetic acid solution for 30 minutes, stained with Sypro® ruby stain overnight, and destained in dd$H_2O$ for 3 hours prior to UV excitation and visualization. The gel was sliced into 1 mm$^2$ gel regions and the gel bands were destained in 50% methanol. Gel bands were reduced and alkylated with 10 mM dithiothreitol (DTT) and 55 mM iodoacetamide, incubated at 4° C. for 1 hour in trypsin (20 ng/µL) and allowed to digest overnight (16 hours) at 37° C. in 25 mM $NH_4HCO_3$. The following morning, proteins were extracted from the gel with repeated incubations of 70% ACN/5% formic acid solution.

µLC/MS/MS analysis: The samples were lyophilized to near dryness and reconstituted in 6.5 µL of HPLC buffer A (95% $H_2O$, 5% ACN, 0.1% FA) for mass spec analysis. Microcapillary reverse phase LC/MS/MS analysis was performed with Dionex's LC Packings liquid chromatography system coupled online to a ThermoFinnigan LCQ Classic ion trap mass spectrometer (San Jose, Calif.) with a modified nanospray source. Reverse phase separations were performed with an in-house, slurry packed capillary column. The $C_{18}$ silica-bonded column is 75 µm i.d., 360 µm o.d., 10 cm long fused silica packed with 5 µm beads with 300 Angstrom pores (Vydac, Hesperia, Calif.). A µ-precolumn PepMap, 5 mm, $C_{18}$ cartridge (Dionex) acts as a desalting column. Sample is injected in µL pick-up mode and washed with Buffer A for five minutes prior to a linear gradient elution with Buffer B (95% ACN/5% $H_2O$/0.1% formic acid) up to 85% over 95 minutes at a flow rate of 200 mL/minute. Full MS scans are followed by four MS/MS scans of the most abundant peptide ions (in a data dependant mode) and collision induced dissociation (CID) is performed at a collision energy of 38% with the ion spray voltage set to 2.00 kV, capillary voltage and temperature to 22.80 V and 180° C., respectively.

Data analysis: Data analysis was performed by searching MS/MS spectra against the European Bioinformatics Institute of the non-redundant proteome set of Swiss-Prot, TrEMBL and Ensembl entries through the Sequest Bioworks Browser (ThermoFinnigan). Peptides were considered legitimate hits after filtering the correlation scores (Table 1) and manual inspection of the MS/MS data. Criteria used to filter data are at least as stringent as most literature citations.

TABLE 1

| Charge | $X_{corr}$ | DeltaCN | Ions | Rsp |
|---|---|---|---|---|
| +1 | >1.9 | >0.1 | >50% | =1 |
| +2 | >2.5 | >0.1 | >50% | =1 |
| +3 | >3.5 | >0.1 | >50% | =1 |

Accepted peptide hits are required to have an $X_{corr}$ ranking = 1 relative to all other peptides in the database.

Results.

Serum Depletion Using Nanoporous Silicon.

Figure 6:
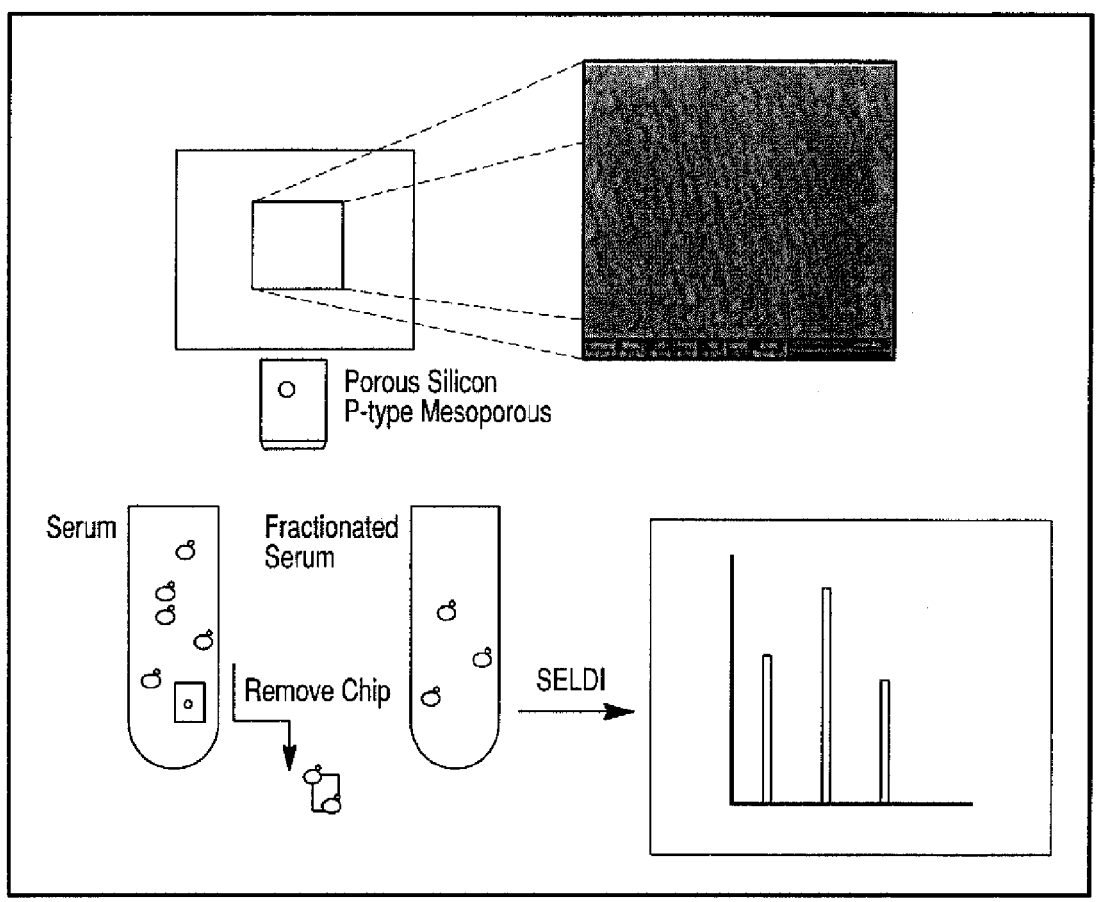
Figure 7:
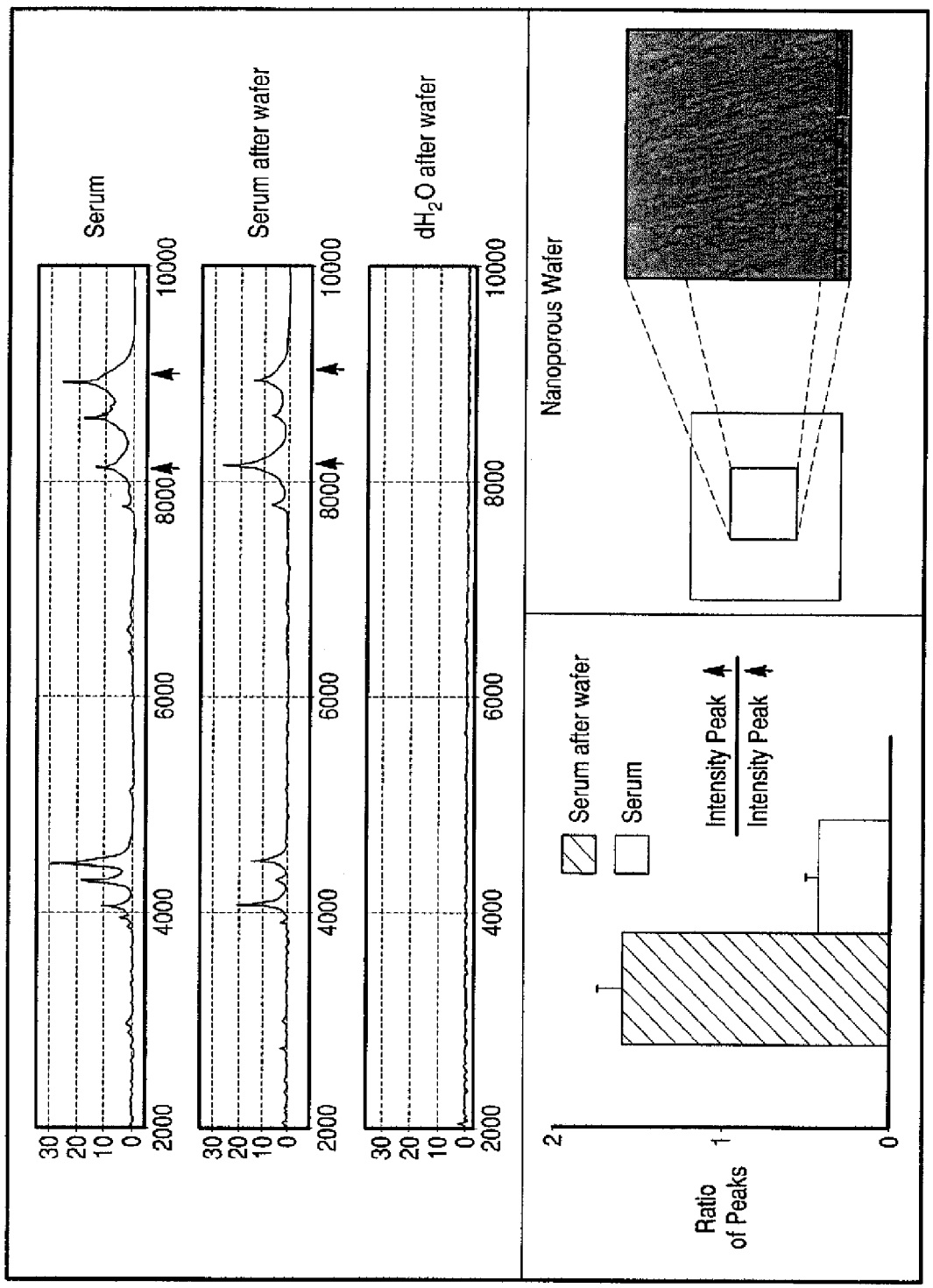

One strategy for fractionating serum is to deplete the serum of a portion of its protein content, followed by analysis of the remaining protein species, see FIG. 6. In order to try this approach, a nanoporous substrate was produced out of silicon. Nanoporous silicon wafers possessing an asymmetric surface were incubated with pooled serum samples. After an 1.5 hr incubation, the wafers were removed and the remaining proteins within the serum were subjected to MS evaluation, see FIG. 7. An emergence of a new ion peak pattern from surface enhanced laser desorption ionization (SELDI) mass spectrometry resulted from the fractionation technique. The entire spectra appeared dramatically different compared to unfractionated serum alone. In the case of the depletion experiment, two peaks within the MS spectra were markedly changed. A peak at 8122 m/z was significantly enhanced in the depleted sample, when compared with the native serum sample, i.e. unfractioned serum sample. On the other hand, the 8927 m/z peak was markedly diminished within the depleted sample, when compared with its dominance in native serum. Thus, the incubation followed by the removal of the nanoporous particles altered the spectral qualities of the serum, enhancing the profile of a previously minor peak into the dominating area of intensity.

Molecular Harvesting Using Nanoporous Controlled-Pore Glass.

Figure 8:
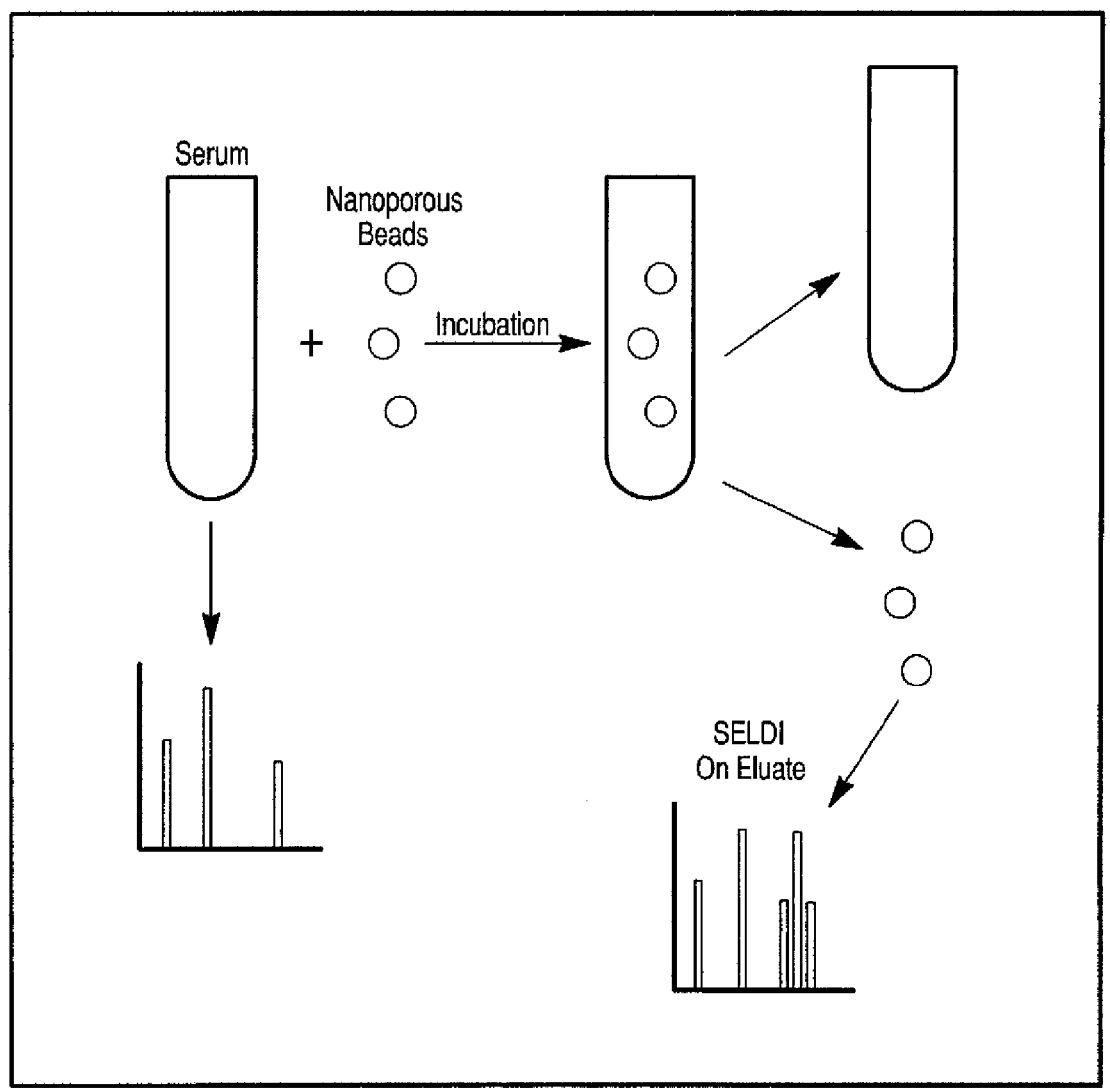
Figure 9:
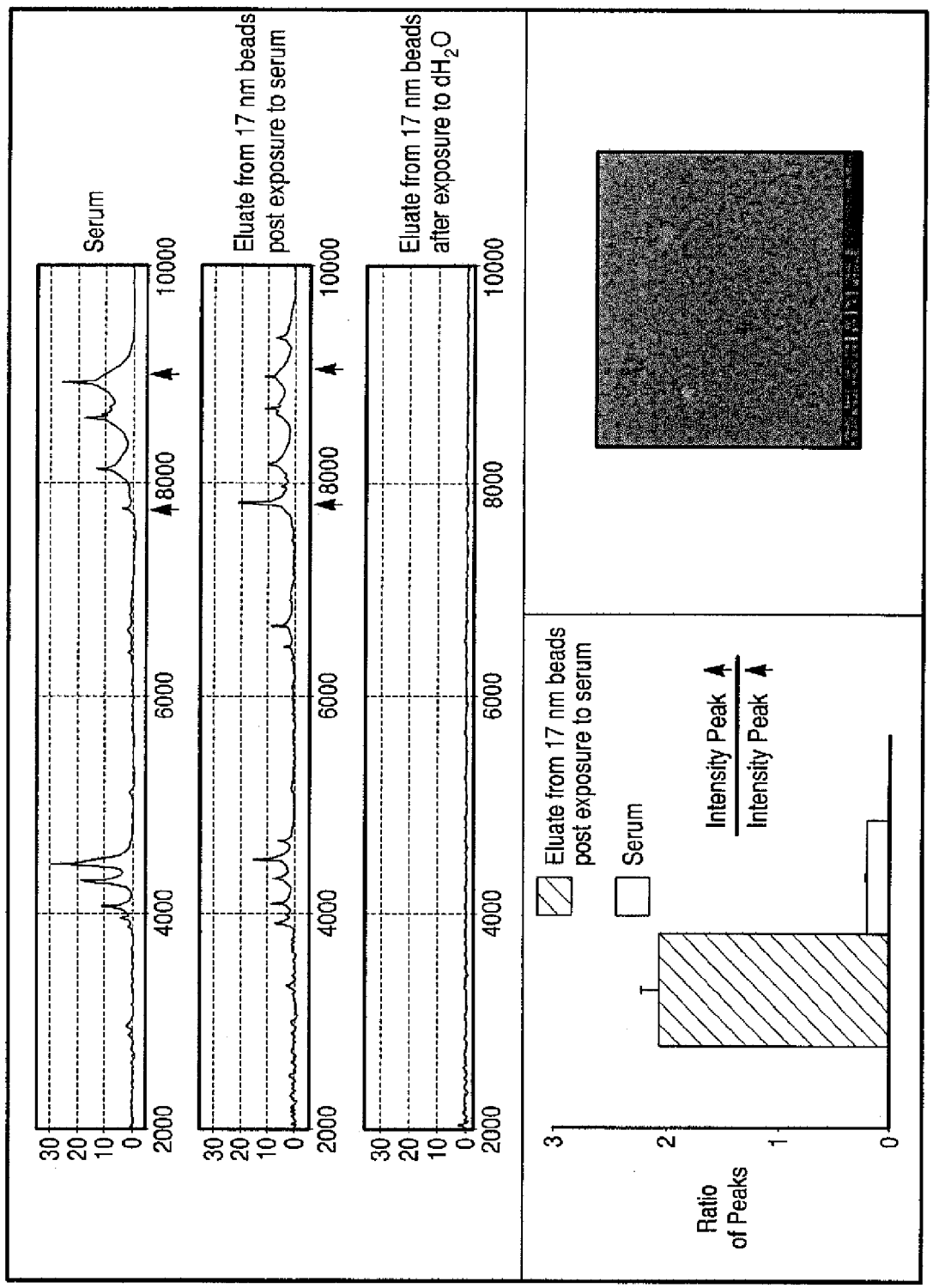

As an alternative to measuring depleted serum for proteomic signatures, a bead harvesting strategy was developed for isolating molecular species for subsequent elution and profiling, see FIG. 8. Aminopropyl-coated glass beads with distinct pore sizes (17 nm versus 70 nm) were incubated with serum for selective molecular isolation and release. Following the incubation with serum, the beads were gently washed with water and then the bound molecules were eluted using a harsh solution. The eluted species were then analyzed via SELDI MS and compared with spectra of unfractionated serum, see FIG. 9. Visual inspection of the 17 nm bead eluate revealed a unique MS spectral portrait when compared with unprocessed serum. Again, visual inspection was sufficient to detect a marked difference at the m/z of 7762 when comparing the harvested sample and the native (unprocessed) serum. While the 8927 m/z peak dominates the spectral landscape in normal serum, it is the 7762 m/z peak that assumes the dominant role in the harvested subset.

Figure 10:
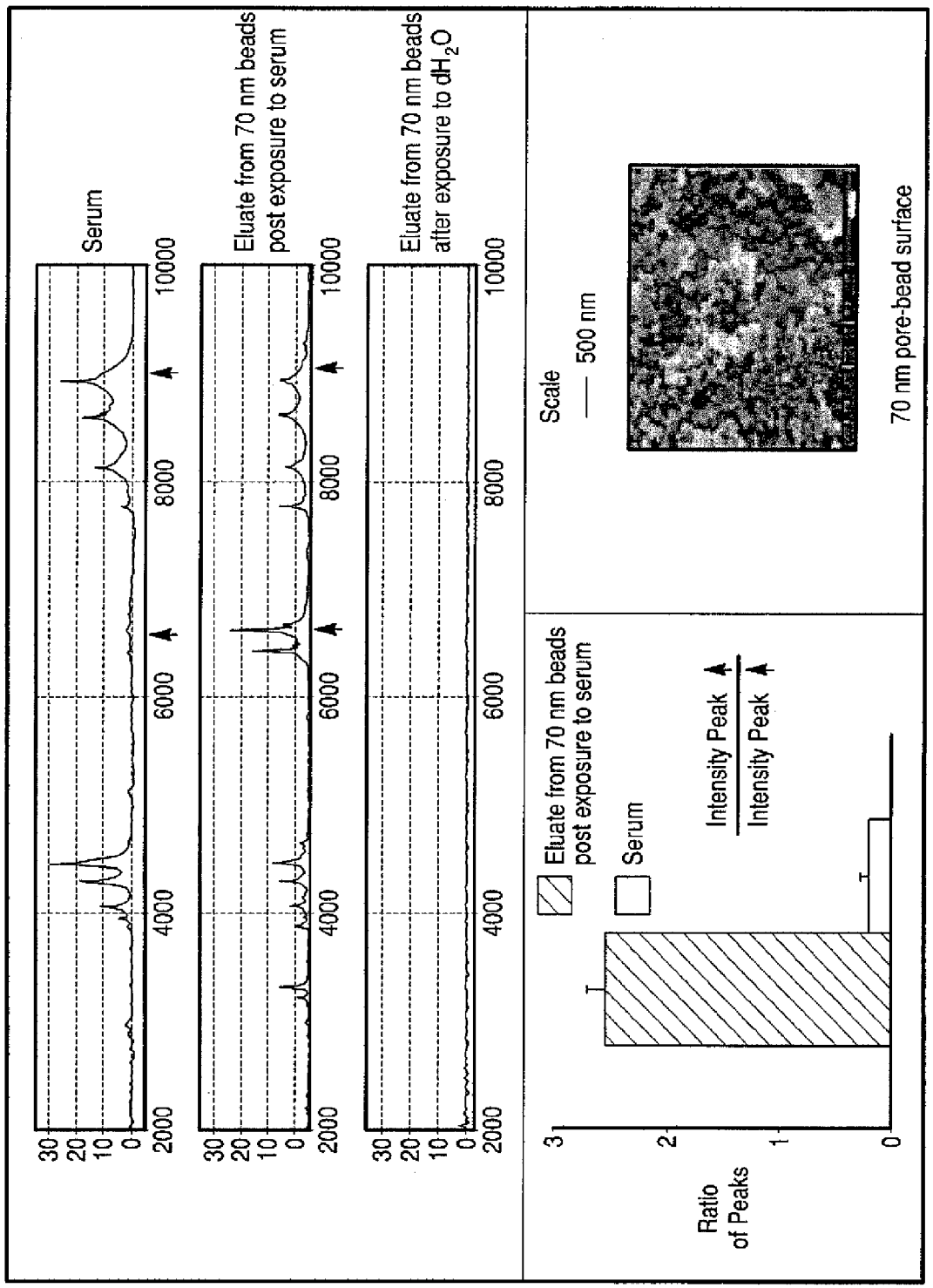

In order to assess an effect that the nanopore size played in the generation of unique spectral signatures, a 70 nm pore-sized controlled pore glass bead was used in an identical experiment. Strikingly, a markedly different SELDI MS spectra resulted using a larger pore controlled pore glass beads, see FIG. 10. At 6629 m/z, a new major peak dominated the spectral pattern eluted from the beads. The normal serum peak at the same m/z was barely discernible. In contrast, the 8927 peak in normal serum assumed a minor status within the set of proteins eluted from the larger pore beads.

Figure 11:
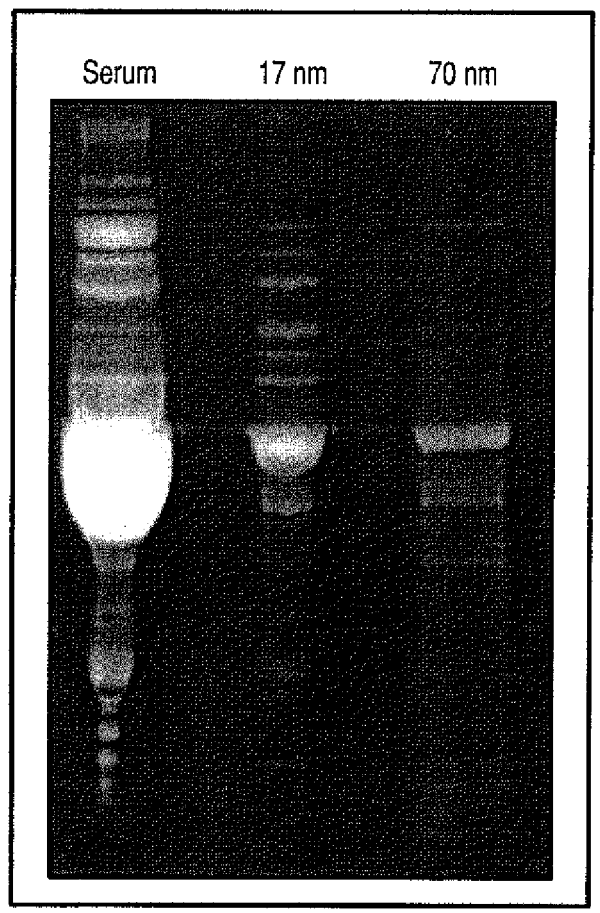

To further characterize molecular components eluted from either the 17 nm pore sized beads or 70 nm pored-sized beads, 15 µg of protein from each sample was run on a 4-12% Bis-Tris SDS-PAGE gel followed by staining with Sypro® Ruby Red, see FIG. 11. Throughout the molecular weight spectrum, distinct differences were noted between the eluates from the two types of beads. This finding was consistent with the marked differences noted in the SELDI-based analysis. Analysis of the molecular content of the eluants via one dimensional electrophoresis provided additional confirmation that the beads were differentially fractionating the molecular content of serum.

In order to further characterize differences between the eluants from the 17 nm-pore sized beads and the 70 nm pore sized beads, bands from a SDS-PAGE gel were excised and the protein content of the gel slices were digested using trypsin. The resulting peptide fragments were analyzed using electrospray ionization mass spectrometry. Following interrogation of the spectral data, peptide identities were assigned to the proteomic content of the gel, see FIG. 12. Twenty-five peptide species were identified within the eluant from the 70 nm-pore sized beads while thirteen peptide species were identified within the eluant of the 17 nm-pore sized beads. While there was some overlap of the peptide species identified (six peptides shared), differences were observed, indicating that significant fractionation had occurred. Thus, three distinct analyses indicate that the glass beads with different pore sizes offer a means of fractionating serum components.

Discussion.

Proteomic profiling using mass spectrometry coupled with bioinformatics data mining approaches has revealed a complex and exciting information archive, contained within the low molecular weight range of the circulatory proteome, which may contain important diagnostic information. Nanoporous material surfaces, such as a silicon wafer and a controlled pore glass beads, provide a strategic and new means to fractionate and manipulate the low molecular weight biologic information contained within body fluids such as serum. A systematic evaluation of nanoporous material surfaces combining MS analysis with bioinformatic interrogation may reveal certain fractionation schemes with enhanced disease detection properties, identify an expanded set of molecules for work-up and provide a more facile and robust means for purification, fractionation and peptide/protein sequencing of the molecules themselves.

To that end, in this study fractionation of serum using material surfaces with nanopores can result in significantly altered spectral profiles, altered 1-D electrophoretic profiles, and differential sequence identities. Each of these parameters suggests a significant, unique fractionation had occurred using either the 17 nm pore sized beads or the 70 nm pore sized beads. While six of the peptide species identified by ESI MS were harvested using either of the bead types, there were distinct peptides that were only isolated using only one type of the beads. The sequenced peptides included highly abundant plasma proteins as well as lower abundance species. For example, in the 70 nm pore-sized beads, the protein named mediator of RNA polymerase II transcription subunit 8 homolog was isolated. In the 17 nm pore-sized bead fraction, histone 4 and golgi autoantigen were harvested. The presence of these molecular species not traditionally thought of as serum proteins, may support a hypothesis that fragments of organismal proteins make their way into the serum and provide a potential portrait of the overall state of the organism. One protein isolated using the 70 nm pore-sized beads, apolipoprotein A-1, has been recently reported as a potential marker for ovarian cancer (Zhang et al., 2004). In addition, transthyretin, also reported as a potential ovarian cancer marker in the study just mentioned, was harvested using the 17 nm pore-sized beads.

Figure 13:
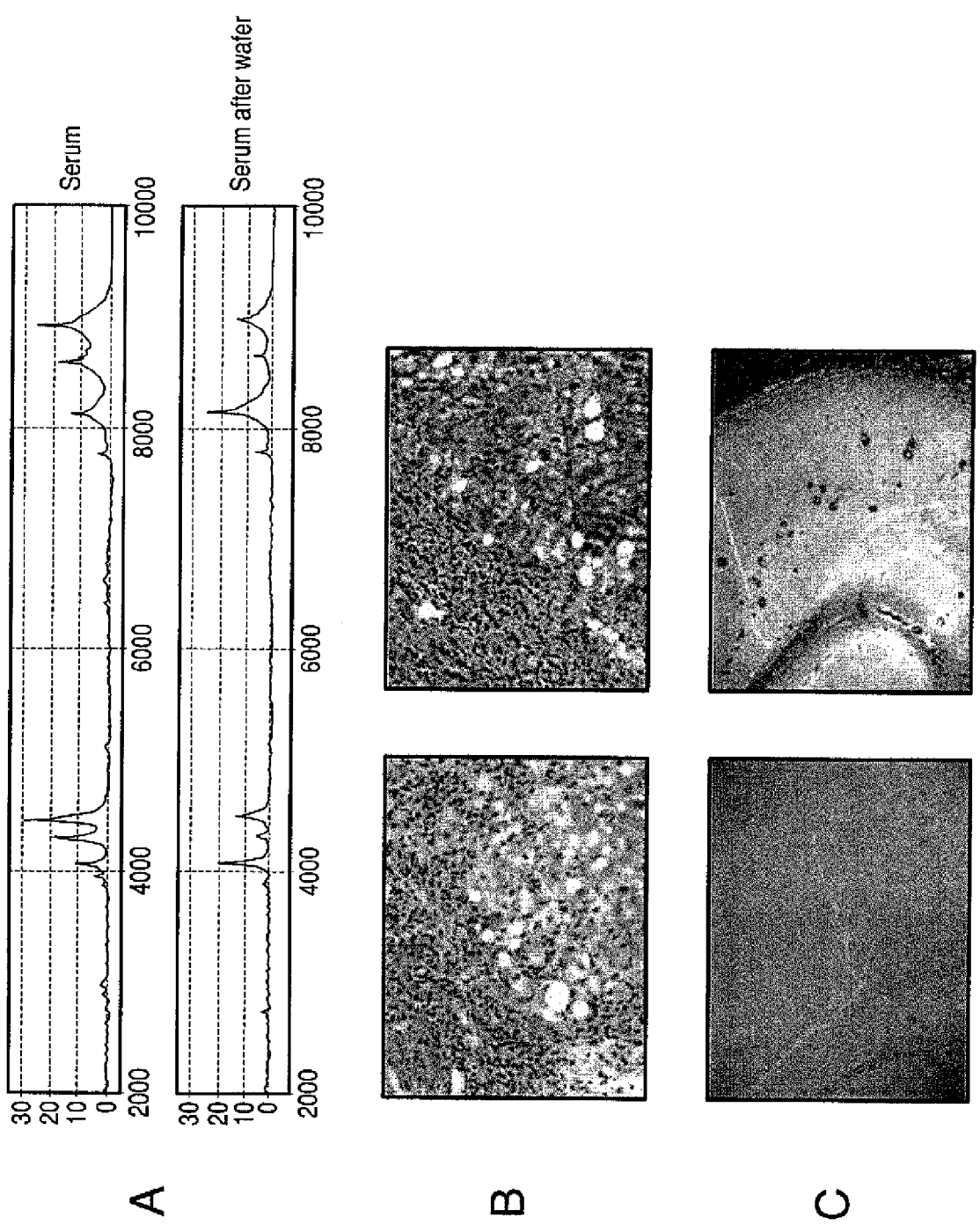

The use of special techniques to enhance biomarker information recovery from blood may be similar to the use of special histochemical studies in anatomic pathology diagnosis. Anatomic pathology is a semiology, whose discriminators are generated by difference analysis between diseased and normal tissue specimens. The indicators of disease are discovered following laborious visual comparisons of routinely stained tissue sections, and following application of novel histochemical techniques. The latter approach to investigative pathology/tissue information mining has occasionally been so fruitful as to prompt the recursive reclassification of many diseases and conditions; accordingly, the diagnosis of many pathologic conditions has come to rely upon information essentially revealed following histochemical special studies, see FIG. 13. While specialized tissue analysis beyond routine studies, such as an H&E slide, does not increase the information content of the tissue, it may significantly increase the recoverable information, leading to novel refinements in disease classification and prognostication as well as providing additional clues to disease origins and basic biology.

The serum and circulatory proteome can be a mixture of high and low abundance molecules, with most biomarkers that carry important diagnostic information may be residing in the lower abundance region of the concentration range. A challenge for clinical proteomics is to develop tools to rapidly identify these low abundance molecules in complex biological samples. One approach is to develop flow through surfaces or depletion architectures for rapid, robust and facile fractionation and selective purification. Nanoporous materials are amenable to physicomodification whereby distinct pore sizes and charge characteristics can be added to the pore surface. These discriminatory properties can allow fine-tuning of the fractionation of proteins within the serum. Additionally, affinity proteins can be added to the material surface in order to further refine the fractionation properties of the substrate.

The above experiments indicate that fractionation of serum using material surfaces with nanopores can result in significantly altered spectral profiles, which indicates an effect of the fractionation methodology. One use for the nanoporous materials can be a collection device for serum samples. As labile molecules in the serum increasingly become interesting as biomarkers, standardized collection procedures can be initiated. Nanoporous substrates may offer one means of sequestering labile small molecules in a format readily adaptable to serum collection procedures. In this type of application, the specialized nanoporous substrate may become akin to specialized tissue fixatives, which are chosen in select cases to preserve specific tissue properties for subsequent analysis and/or visualization.

Because silicon can be fashioned into micron-sized particles, nanoporous substrates can be developed in a size range of blood cells. Such particles can be designed with a range of pore sizes and other physicochemical properties for fractionation of abundant serum proteins and the low molecular weight cargo they carry. As an added feature, the micron-sized particles can be coded with a discriminating tag, such as a metallic tags or quantum dots. Such a strategy can allow blood to be harvested and the particles isolated from the blood cells through a sorting or enrichment process, similar to a process described in Bruchez et al., 1998; Han et al., 2001; Nicewarner-Pena et al., 2001.

The present study demonstrates a feasibility of nanoporous based separation and fractionation of low molecular weight molecules as a means to selectively fractionate, purify and analyze the circulatory proteome.

REFERENCES

Bruchez, M., Jr., Moronne, M., Gin, P., Weiss, S., and Alivisatos, A. P. (1998). Semiconductor nanocrystals as fluorescent biological labels. Science 281, 2013-2016.

Chaurand, P., and Caprioli, R. M. (2002). Direct profiling and imaging of peptides and proteins from mammalian cells and tissue sections by mass spectrometry. Electrophoresis 23, 3125-3135.

Geho, D. H., Lahar, N., Ferrari, M., Petricoin, E. F., and Liotta, L. A. (2004). Opportunities for nanotechnology-based innovation in tissue proteomics. Biomed Microdevices 6, 231-239.

Han, M., Gao, X., Su, J., and Nie, S. (2001). Quantum-dot-tagged microbeads for multiplexed optical coding of biomolecules. Nature Biotechnology 19, 631-635.

Hingorani, S. R., Petricoin, E. F., Maitra, A., Rajapakse, V., King, C., Jacobetz, M. A., Ross, S., Conrads, T. P., Veenstra, T. D., Hitt, B. A., et al. (2003). Preinvasive and invasive ductal pancreatic cancer and its early detection in the mouse. Cancer Cell 4, 437-450.

Howorka, S., Cheley, S., and Bayley, H. (2001). Sequence-specific detection of individual DNA strands using engineered nanopores. Nat Biotechnol 19, 636-639.

Liotta, L. A., Ferrari, M., and Petricoin, E. (2003). Clinical proteomics: written in blood. Nature 425, 905.

Mehta, A. I., Ross, S., Lowenthal, M., Fusaro, V. A., Fishman, D. A., Petricoin, E., and Liotta, L. (2003). Biomarker amplification by serum carrier protein binding. Disease Markers 19, 1-10.

Meller, A., Nivon, L., Brandin, E., Golovchenko, J., and Branton, D. (2000). Rapid nanopore discrimination between single polynucleotide molecules. Proc Natl Acad Sci USA 97, 1079-1084.

Nicewarner-Pena, S. R., Freeman, R. G., Reiss, B. D., He, L., Pena, D. J., Walton, I. D., Cromer, R., Keating, C. D., and Natan, M. J. (2001). Submicrometer metallic barcodes. Science 294, 137-141.

Paweletz, C. P., Gillespie, J. W., Ornstein, D. K., and al., e. (2000). Rapid protein display profiling of cancer progression directly from human tissue using a protein biochip. Drug Develop Res 49, 34-42.

Petricoin, E. F., 3rd, Ornstein, D. K., Paweletz, C. P., Ardekani, A., Hackett, P. S., Hitt, B. A., Velassco, A., Trucco, C., Wiegand, L., Wood, K., et al. (2002a). Serum proteomic patterns for detection of prostate cancer. J Natl Cancer Inst 94, 1576-1578.

Petricoin, E. F., Ardekani, A. M., Hitt, B. A., Levine, P. J., Fusaro, V. A., Steinberg, S. M., Mills, G. B., Simone, C., Fishman, D. A., Kohn, E. C., and Liotta, L. A. (2002b). Use of proteomic patterns in serum to identify ovarian cancer. Lancet 359, 572-577.

Rosenblatt, K. P., Bryant-Greenwood, P., Killian, J. K., Mehta, A., Geho, D., Espina, V., Petricoin, E. F., 3rd, and Liotta, L. A. (2004). Serum proteomics in cancer diagnosis and management. Annu Rev Med 55, 97-112.

Schwartz, S. A., Weil, R. J., Johnson, M. D., Toms, S. A., and Caprioli, R. M. (2004). Protein profiling in brain tumors using mass spectrometry: feasibility of a new technique for the analysis of protein expression. Clin Cancer Res 10, 981-987.

Stoeckli, M., Chaurand, P., Hallahan, D. E., and Caprioli, R. M. (2001). Imaging mass spectrometry: a new technology for the analysis of protein expression in mammalian tissues. Nat Med 7, 493-496.

Wang, H., and Branton, D. (2001). Nanopores with a spark for single-molecule detection. Nat Biotechnol 19, 622-623.

Yanagisawa, K., Shyr, Y., Xu, B. J., Massion, P. P., Larsen, P. H., White, B. C., Roberts, J. R., Edgerton, M., Gonzalez, A., Nadaf, S., et al. (2003). Proteomic patterns of tumour subsets in non-small-cell lung cancer. Lancet 362, 433-439.

Zhang, Z., Bast, R. C., Jr., Yu, Y., Li, J., Sokoll, L. J., Rai, A. J., Rosenzweig, J. M., Cameron, B., Wang, Y. Y., Meng, X. Y., et al. (2004). Three biomarkers identified from serum proteomic analysis for the detection of early stage ovarian cancer. Cancer Res 64, 5882-5890.

Example 3

The superscript citations in this example refer to the List of References at the end of Example 3.

SUMMARY

The low-molecular weight region of the serum/plasma proteome (LMWP) is gaining interest as a potential source of diagnostic markers for diseases[1-3]. Serum LMW protein profiling[4] by mass spectrometry (MS) has generally relied on surface-enhanced laser desorption/ionization time-of-flight (SELDI-TOF)[5], which involves MS profiling of analytes previously adsorbed on specific chip surfaces[6-9]. The interference of high-molecular weight, abundant proteins present in biofluids, though, may limit sensitivity and might influence reproducibility of the analysis[10]. Improving selectivity of MS-based profiling by using devices allowing specific entrapment of LMW polypeptides prior to MS analysis can minimise such an interference. In this report, nanoporous surfaces were used to selectively capture LMW peptides (<15,000 Da) from human plasma. Mass spectrometry (MS) analysis of harvested peptides was performed using matrix-assisted laser desorption/ionization time-of-flight (MALDI-TOF) as a means of detecting and assessing the bound molecules. Due to the enhanced selectivity of the analysis, a detection of small (<4,000 Da) peptides in human plasma at ng/mL concentration levels was achieved.

Results and Discussion

Figure 14:
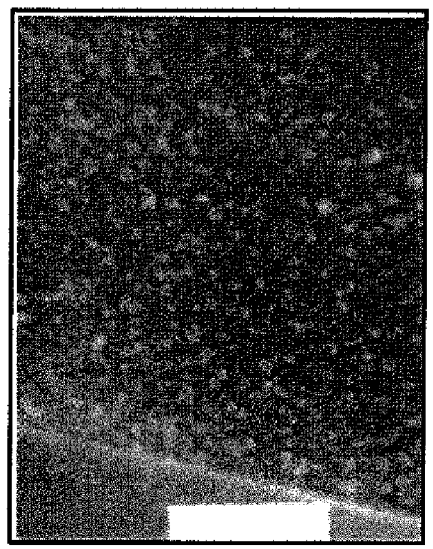

The aim of this work was to develop an approach for isolating LMW peptides contained in body fluids based on a size-exclusion principle. To achieve this goal, nanoporous surfaces having the right porosity were used to operate a molecular cut-off. A device was fabricated by coating silicon chips with a 500 nm thick nanoporous film of silicon oxide. Using Lorentz-Lorenz model, a refractive index was measured to determine a porosity of the film by ellipsometry. An estimated porosity was 57%. Brunauer-Emmett-Teller (BET) surface area of the film determined using nitrogen adsorption-adsorption isotherms measurements was 670 $m^2/g$. An average pore size was around 7 nm. FIG. 14 shows a morphology of the silicon oxide nanoporous film using Transmission Electron Microscopy (TEM).

Figure 15:
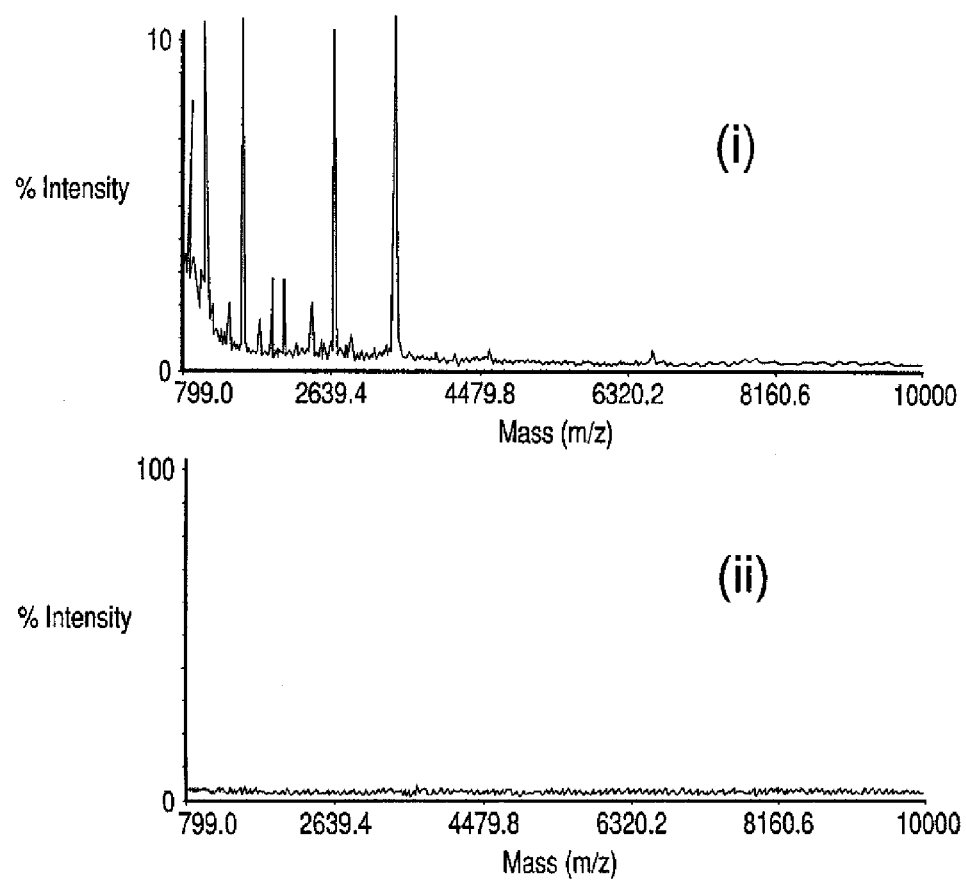

The fabricated chips were used for harvesting LMW peptides from human plasma. After wetting the nanoporous surface with sequential washes of isopropanol and deionised water, a drop (5 μL) of human plasma was applied directly onto the chip surface and subsequently incubated for capturing of peptide/protein species. Following a series of sequential washings of deionised water, bound species were released from the surface by the addition of an acidic MALDI matrix solution (α-cyano-4-hydroxycinnamic acid, CHCA) containing a high percentage of organic solvent (50% v/v). A 1 μL aliquot of the extraction solution was deposited on a MALDI plate and used for MS analysis. In FIG. 15, a comparison between MALDI-TOF spectra obtained using a nanoporous silica surface and a control surface of solid non-nanoporous silica is made. In the former, about 70 low Mw peptides are detected, including human calcitonin, which had been spiked in the incubated plasma at a concentration of 1 μg/mL. In contrast, no peptides were detected in a MS spectrum obtained from the analysis of the control surface. A complementary MALDI-TOF analysis was also performed on the same nanoporous sample using sinapinic acid, a matrix more specific for large proteins. In this case, although the extract traces of albumin and a few other abundant plasma proteins, which would otherwise dominate the MALDI-TOF spectrum, were detected, almost all MS signal was concentrated in a region below 15,000 m/z. Thus, 15 kDa can be an approximate cut-off mass value achieved by the actual experimental conditions and nanoporosity of the surface employed.

Although the present invention is not limited by a theory, isolation and detection of LMW peptides from plasma as displayed in FIG. 15 is probably due to a specific nanometer-sized porosity of the chip surface. Only analytes small enough to easily penetrate the pores can be quantitatively adsorbed onto the chip surface. Thus, this approach can be selectively employed for LMW enrichment and analysis.

Analyte adsorption on the chip surface has to be strong enough to resist extensive washes of the chip after capture during the incubation step. In this particular case, ionic interactions of the LMW analytes with the silanol groups present on the silica nanoporous layer may account for analyte binding.

Figure 16:
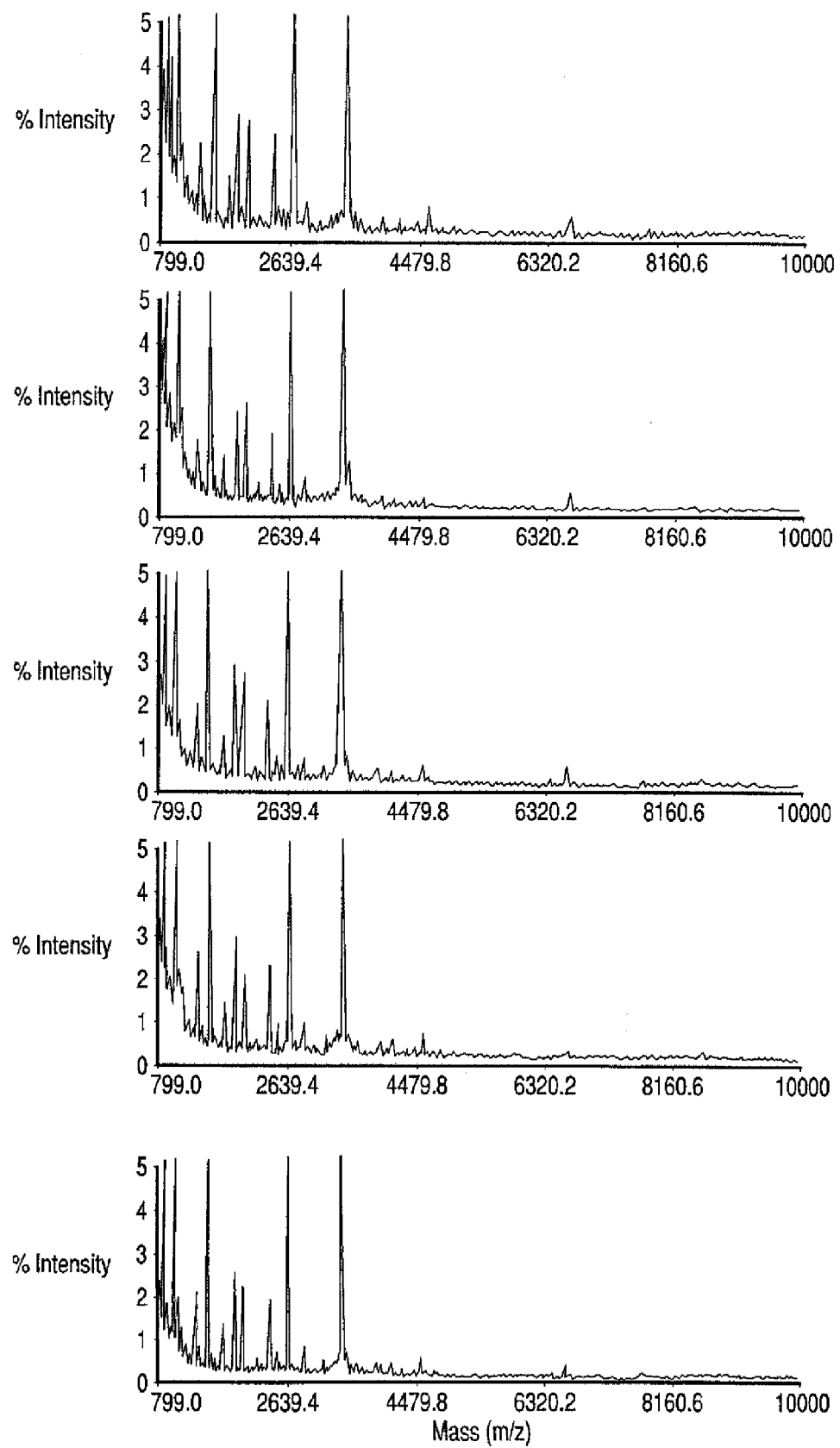

To assess repeatability of the profile generated, five replicate analyses were performed on the same plasma sample. The MALDI-TOF spectra obtained are reported in FIG. 16, where the repeatability of the LMW profile can be appreciated.

Figure 17:
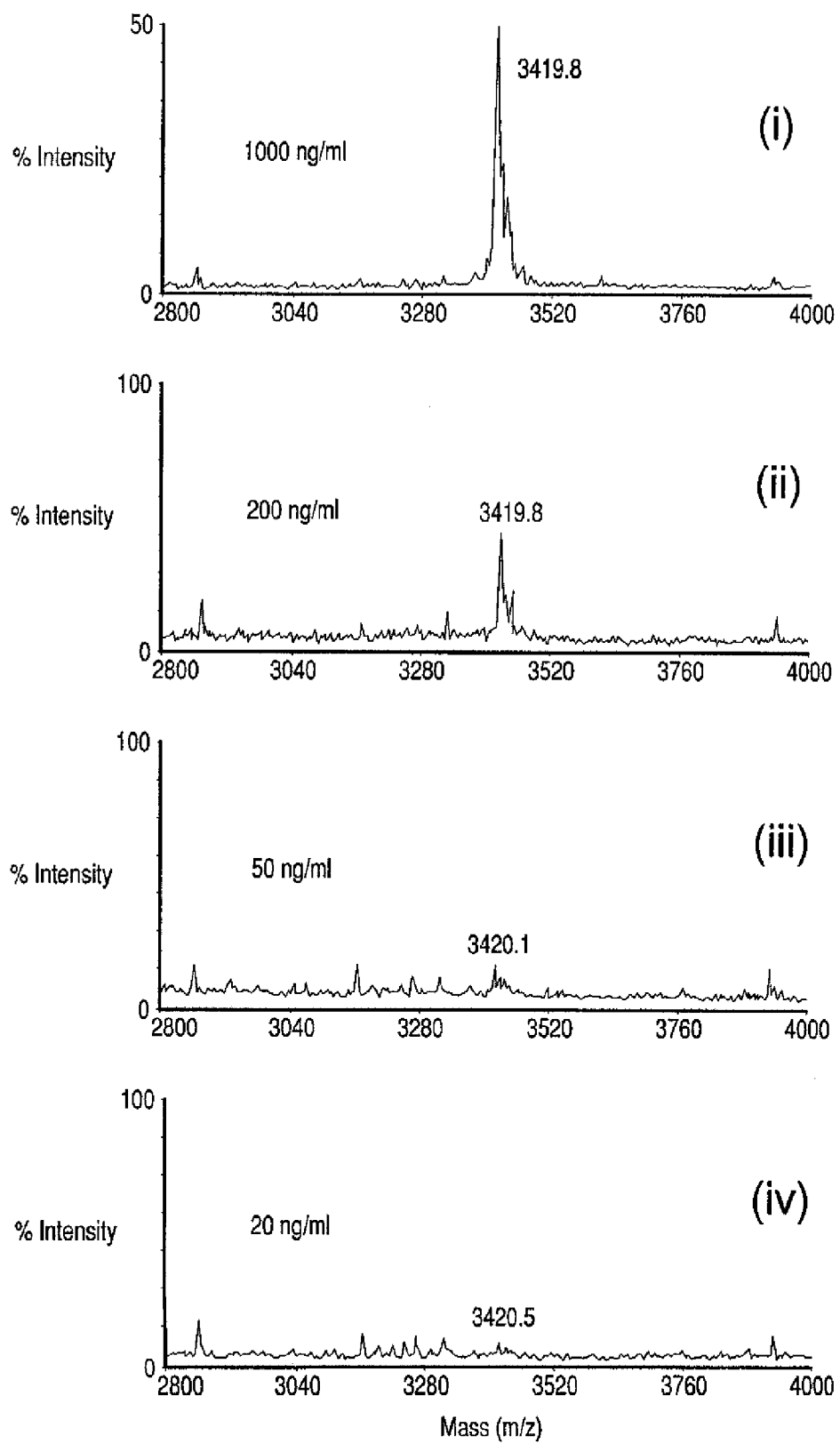
Figure 18:
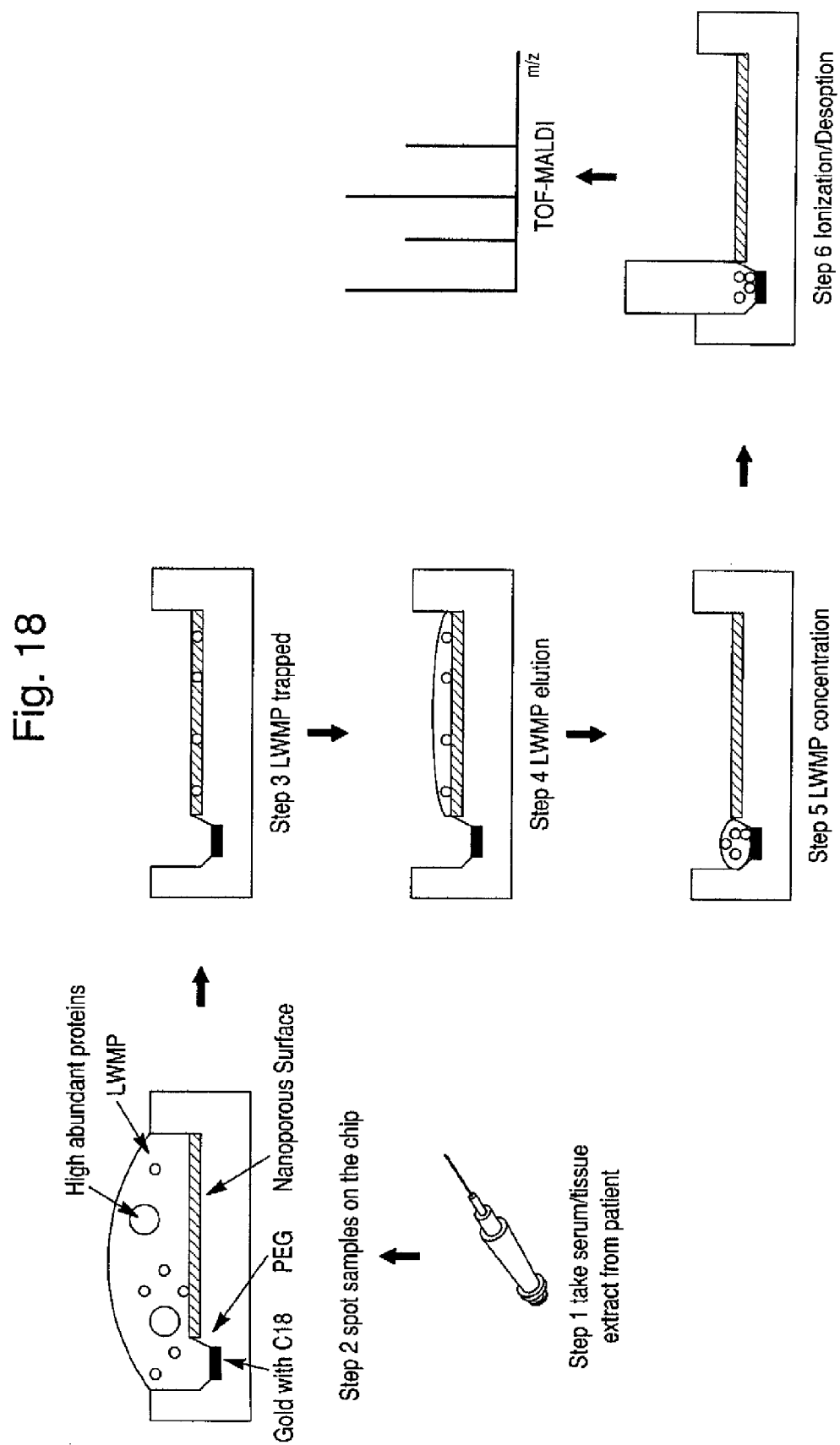

A detection limit (DL) of the method can be estimated by adding a commercially available peptide, calcitonin, to human plasma at different concentrations. Human calcitonin, was spiked into plasma before analysis to mimic conditions in vivo. The analysis was performed by incubating the spiked plasma on the nanoporous silica surface followed by subsequent MALDI-TOF profiling. FIG. 17 displays the intensity of the peak corresponding to the calcitonin protonated molecule (theoretical m/z=3421.0) at four different concentration levels, down to 20 ng/mL. This concentration DL represents a dramatic improvement with respect to recent data reported in the literature[11] using similar approaches.

A drop of the spiked plasma having the lowest calcitonin concentration, 20 ng/mL, contained an absolute amount of 100 pg calcitonin (5 μL applied to the nanoporous surface). Considering that ⅓ of the extraction solution was deposited on the MALDI plate for analysis, a maximum of 33 pg calcitonin was available for MALDI-TOF detection. Such an amount corresponds to the actual DL for calcitonin analysed by MALDI-TOF in standard conditions (standard peptide solution mixed with CHCA matrix, 1 μL deposited on MALDI target for analysis). This indicates that a significant portion of the spiked calcitonin was efficiently harvested from plasma by the nanoporous surface even at the lowest concentration analysed, and made available for MS detection after LMW peptide extraction.

Silicon-based nanoporous surfaces were also able to create such a molecular cut-off. Nanoporous silicon was fabricated by electrochemical etching, creating a mesoscopic topography (nanosized pores film, similar to nanoporous silica, covering microsized caves of silicon). The nanoporous silicon has been used as a harvesting agent in the protocol described above instead of silica coated chip. A sequestration of two low-MW standard peptides in presence of a strong excess of the large protein albumin was observed by mass spectrometry.

Methods

Nanoporous Surface Fabrication

The nanoporous film of oxide was prepared as followed. 8.71 g of surfactants $EO_{106}PO_{70}EO_{106}$ (Pluronic F127, BASF) was added in 23 g of Ethanol. A mixture of 10 g of tetraethylorthosilicate (TEOS, Aldrich), 0.1006 g of hydrochloride (20%), 10 g of Ethanol and 10.629 g of water was then added under vigorous stirring 8. After aged for 3-6 h at room temperature, a precursor solution was spin-coated onto the silicon wafer at 1900 rpm for 30 s. After spin-coating, the film was baked at 100° C. for 12 h, followed by 400° C. for 2 h in a furnace.

Sample Preparation

The chip surface was wetted using isopropanol. After a water wash, 5 μL of human plasma (collected according to published guidelines[19]) from healthy volunteers under consent and Institutional Review Board monitoring for human subjects protection were applied to the chip surface and allowed to incubate for 30 minutes at room temperature in 100% humidity. The sample was removed using a pipettor. The surface was then washed by 5 sequential 5 μL aliquots of water, allowing the droplet to rest on the surface for 1 minute each time. After the last wash, 3 μL of a MALDI matrix solution consisting of 3 mg/mL α-cyano-4-hydroxycinnamic acid (CHCA, Sigma) in a 1:1 mixture of acetonitrile and 0.1% trifluoroacetic acid (TFA) (v/v) was used to extract analytes bound to the chip surface. 1 μL of the extract was deposited on a MALDI sample plate and allowed to dry before mass spectrometric analysis.

Mass Spectrometry

MALDI-TOF was performed on a Voyager-DE™ STR MALDI-TOF (Applied Biosystems) mass spectrometer equipped with a nitrogen laser emitting at 337 nm. Spectra were acquired in a linear positive mode using a delayed extraction time of 700 nanoseconds and an accelerating voltage of 20 kV. 500-600 laser shots were typically averaged to produce the final sample spectrum.

REFERENCES

1. Liotta, L. A., Ferrari, M., Petricoin, E. Written in blood. Nature 425, 905 (2003).
2. Villanueva, J., Tempst, P. OvaCheck: let's not dismiss the concept. Nature 430, 611 (2004).
3. Villanueva, J. et al. Corretting common errors in identifying cancer-specific serum peptide signatures. J. Proteome Res. 4, 1060-1062 (2005).
4. Petricoin, E. F. et al. Use of proteomic patterns in serum to identify ovarian cancer. Lancet 359, 572-577 (2002).
5. Issaq, H. J., Conrads, T. P., Prieto, D. A., Tirumalai, R., Veenstra, T. D. SELDI-TOF MS for diagnostic proteomics. Anal. Chem. 75, 148A-155A (2003).
6. Ebert, M. P., et al. Identification of gastric cancer patients by serum protein profiling. J. Proteome Res. 3, 1261-1266 (2004).
7. Zhang, Z. et al. Three biomarkers identified from serum proteomic analysis for the detection of early stage ovarian cancer. Cancer Res. 64, 5882-5890 (2004).
8. Chen, Y. D., Zheng, S., Yu, J. K., Hu, X. Artificial neural networks analysis of surface-enhanced laser desorption/ionization mass spectra of serum protein pattern distinguishes colorectal cancer from healthy population. Clin. Cancer Res. 10, 8380-8385 (2004).
9. Carrette, O. et al. A panel of cerebrospinal fluid potential biomarkers for the diagnosis of Alzheimer's disease. Proteomics 3, 1486-1494 (2003).
10. Diamandis, E. P. Mass spectrometry as a diagnostic and a cancer biomarker discovery tool: opportunities and potential limitations. Mol. Cell. Proteomics 3, 367-378 (2004).
11. Diamandis, E. P., van der Merwe, D. E. Plasma protein profiling by mass spectrometry for cancer diagnosis: opportunities and limitations. Clin Cancer Res. 11, 963-965 (2005).
12. Geho, D. H., Lahar, N., Ferrari, M., Petricoin, E. F., Liotta, L. A. Opportunities for nanotechnology-based innovation in tissue proteomics. Biomed. Microdevices 6, 231-239 (2004).
13. Trauger, S. A. et al. High sensitivity and analyte capture with desorption/ionization mass spectrometry on silylated porous silicon. Anal. Chem. 76, 4484-4489 (2004).
14. Go, E. P. et al. Desorption/ionization on silicon nanowires. Anal. Chem. 77, 1641-1646 (2005).
15. Mehta, A. I. et al. Biomarker amplification by serum carrier protein binding. Dis. Markers 19, 1-10 (2003-2004).
16. Liotta, L. A. et al. Importance of communication between producers and consumers of publicly available experimental data. J. Natl. Cancer Inst. 97, 310-314 (2005).
17. Lowenthal, M. S., et al., Clin. Chem. October 2005; 51: 1933-1945.
18. Cohen, M. H., Melink, K., Boiarski A. A., Ferrari M., Martin, F. J. Microfabrication of silicon-based nanoporous particulates for medical applications. Biomed. Microdevices 5, 253-259 (2003).
19. Hulmes, J. D., et al. An Investigation of Plasma Collection, Stabilization, and Storage Procedures for Proteomic Analysis of Clinical Samples. Clin. Proteomics 1, 17-32 (2004).

Example 4

Proteomic Nanochips for Harvesting and Targeting Angiogenic Proteins

The citations in the parentheses in this example refer to the List of References at the end of Example 4.

Mass spectrometry (MS) is a powerful technology for the qualitative and quantitative characterization of peptides with molecular weights of less than 20 kDa. In terms of sensitivity, laser desorption MS was recently demonstrated to be capable of detecting peptides within the low attamole level of sensitivity (7). Thus, in principle, MS allows analytical access to peptides present in solution at levels of pg/mL using just a few microliters of available sample. Detecting peptide species at such low levels in human serum and tissue represents an extremely powerful tool for biomarker discovery. Nevertheless, such level of sensitivity has not yet been achieved by routine MS analysis of human serum or tissues. This is mainly due to a limited dynamic range of MS analysis, which, in the best case, is capable of detection of peptide analytes in the presence of a maximum of 10,000 fold excess of interfering species such as other proteins/peptides. The interference of high molecular weight carrier proteins, present at mg/mL levels, allows for the detection of peptides present at concentrations of a maximum of 3-4 orders of magnitude lower, i.e. within the low μg/mL range.

Recent attention has focused on the low-molecular weight proteome (LMWP) within human serum as a potential source of diagnostic markers (3, 8-11). The use of MS for analysis of LMWP that are present in serum and tissues at very low levels implies that extensive sample fractionation may be necessary to enhance our ability to detect this important source of information. One method, by which the complexity of the peptides being analyzed may be reduced, is an isolation of a fraction of the whole proteome having specific physico-chemical characteristics, e.g. fractionation of peptides based on size.

Nanoporous silica/silicon-based surfaces with specific pore sizes and porosity allow adsorption of low molecular weight peptides in serum samples. Use of such surfaces with defined characteristics generates a molecular cut-off or sieve. A few microliters of serum can thus be directly applied onto a nanoporous surface for harvesting of LMWP. After washing the nanoporous surface, the bound analytes can then be collected and profiled by matrix-assisted laser desorption ionization time-of-flight MS (MALDI-TOF MS). The improvement in sensitivity of detection of proteins of specific sizes using a nanoporous surface provided by this approach allows exploration of LMWP present at ng/mL concentrations in serum and tissues.

In addition to developing nanoporous particles as a means to enhance sensitivity of capture and identification of peptides present in serum and tumor tissue, this example focuses on a development and refinement of an integrated silica/silicon chip to improve sensitivity. The surface of the chip is constructed with several patterned "active" nanoporous spots, which are distributed over an inert, non-porous, non-adsorbant chip surface. Modification of the surface properties of the silica/silicon chip can allow LMW peptides contained in a 5-10 μL sample of serum or tissue extract that are deposited onto the chip to be adsorbed, concentrated, and confined in the "spot" region. Extraction of the bound analytes in a minimal volume (100-200 mL) prior to MS analysis can enhance sensitivity. Furthermore, direct MS ionization from the chip with the nanoporous spot surface would avoid further sample dilution. By combining an on-chip up-concentration approach with direct "spot" ionization, the improvement in sensitivity can surpass the pg/mL range of analysis limits that currently exist.

In standard conditions (e.g. 1 μL of sample/matrix solution applied to the target), only a tiny fraction of the generated crystals are actually bombarded by the laser and used for acquiring MS data (typically 0.1-1%). Sensitivity improvement can be achieved for an on-surface pre-concentration of peptide analytes of interest by adjusting the surface properties of the chip. Silicon chip surfaces can be constructed in order to present several patterned "active" nanoporous spots and a non-porous, inert (thus not-adsorbing) chip surface for laser ionization. Such an approach can allow LMW peptides contained in a 5-10 uL of serum sample deposited onto the chip to be adsorbed and concentrated in a confined region (i.e. the nanoporous "spot"), provided that the initial sample drop is centered onto a single nanoporous "spot" surrounded by the inert surface. Extraction of the bound analytes in a minimal volume (100-200 mL) before MS analysis can also be beneficial for enhancing sensitivity of analyte detection. Furthermore, direct MS ionization from the nanoporous spot surface can avoid further sample processing/dilutions with matrix. The diameter of the nanoporous spot can be limited by either i) a minimal volume that can be handled by a micropipettor, in case the bound peptides are extracted from the nanoporous surface and deposited onto the MALDI sample stage; ii) a diameter of the laser spot, in case direct ionization from the chip was attempted. In the first option, nanoporous spots in the range 0.5-1 mm diameter can be tested, which can require extraction solution volumes in the hundreds of nanoliter range. In the second case, spot diameters down to 0.1-0.2 mm can be tested. Combining on-chip up-concentration and direct "spot" ionization can provide orders-of-magnitude improvements in sensitivity of analyte detection with respect to analysis of LMWP in serum or tissue samples, and can push the limits of MS analysis of such analytes below the ng/mL range.

Experimental Methods.
Fabrication of Nanoporous Surface:

The nanoporous film of oxide was prepared as follows. 8.71 g of surfactants $EO_{106}PO_{70}EOL_{106}$ (Pluronic® F127) was added in 23 g of ethanol. A mixture of 10 g of tetraethylorthosilicate (TEOS), 0.1006 g of hydrochloride (20%), 10 g of ethanol and 10.629 g of water was then added under vigorous stirring. After being aged for 3-6 h at room temperature, the precursor solution was spin-coated onto a silicon wafer at 1900 rpm for 30 s. After spin-coating, the film was backed at 100° C. for 12 h, followed by 400° C. for 2 h in a furnace. The thickness of the film is approximately 500 nm. A porosity was estimated to be 57% and the average pore size was 7 nm. Brunauer-Emmett-Teller (BET) surface area was estimated to be 670 $m^2/g$ using nitrogen adsorption-adsorption isotherms measurements.

Fabrication of Proteomic Chips:

The process for silicon chip fabrication may include 4 photolithography steps and 1 surface treatment using soft contact. After standard cleaning steps, the laser spotting area was patterned and etched using Reactive Ion Etching (RIE, Lam $Cl_2$: He=180:400 sccm 100 W 300 mT). A thin Titanium/Gold layer of 10 nm/50 nm was deposited using e-beam evaporator (Denton Vacuum, current 100 mA, deposition rate 0.1 nm/min), and patterned by lift-off of the photoresist. The nanoporous surface was spin-coated using the protocol described in previous section and annealed at 400° C. The nanoporous surface was defined by lithography, and etched using buffer oxide etchant. The well of the chip for samples spotting was fabricated using thick negative, photosensitive resist SU-8 (from MicroChem Inc). After exposure, baking, post exposure baking, and developing using the protocol suggested by the manufacturer, 25 μm SU-8 microstructures was formed. The oxygen plasma (MicroRIE 100 W, $O_2$ 100 sscm) was used to clean prior to the treatment of polyethylene glycol (PEG). PEG was used to reduce a protein adsorption on a non-porous silicon surface in a pre-concentration step. The wafer was dipped in 1% PEG (Mw 1000Da, in toluene) with additives of Triethylamine and silicon tetrachloride to form a covalent bond on silica surface. Poly(dimethylsiloxane) (PDMS, Dow Corning) was cast as an elastometric stamp against a master that had a pattern relief. The stamp was dipped in a solution of an 5% chloro(dimethyl)octadecylsilane in toluene, dried and brought into contact with the substrate. Heated 50° C. overnight, and removed the stamp. The linear octadecyl hydrocarbon chains (C18) offer excellent binding capabilities for the laser spotting area.

Surface Modification:

The chip may be composed of separate wells, each having two distinct areas with a specific surface composition. The surface was hydroxylated in oxygen plasma ($O_2$ 100 sccm, 50 W). Positive charge, amine groups were introduced on the surface by silanization with 0.5% v/v 3-aminopropyltriethoxysilane (APTES) in isopropanol (IPA) for 30 min at room temperature. Negative charge, thiol groups was coated on the surface using 0.5% v/v 3-mercaptopropyltrimethoxysilane (MPTMS) and 0.5% v/v $H_2O$ in IPA. Hydrophilic, hydroxyl group was treated with 1% polyethylene glycol (PEG) with additives of triethylamine and silicon tetrachloride. The hydrophobic surface was derivatized by 5% chloro(dimethyl) octadecylsilane ($C_{18}$). After silanization, the particles can be washed 5 times by in solvent, and dried for 2 hr at 110° C. The physical (charge) and functional group can be measured. For example, the amount of charge on the APTES treated surface can be measured by the zeta potential measurement, while the functional amino group density can be determined by Fmoc method, using, for example, 0.4 ml peperidine, 0.4 ml DCM, and 1.6 ml MeOH. Both non-treated and hydrophobic nanoporous surface can be used as a control to study a contribution of the functional group on the enrichment LMWP.

Production of Recombinant Proteins:

Since these experiments were the first identification of differential expression of VEGF transcripts in a mouse system, sequences of $VEGF_{144}$ and $VEGF_{205}$* were cloned and confirmed. Recombinant proteins were produced to analyze functional activities of the newly identified $VEGF_{144}$ and $VEGF_{205}$* splice variants.

Fractionation of Low Molecular Weight Proteins:

The chip surface can be wetted using isopropanol. After a water wash, 5 µL of serum/tumor sample can be applied to the chip surface and allowed to incubate for 30 min at room temperature in 100% humidity. Excess samples can be removed using a micropipet. The surface can then be washed by addition of 5 sequential 5 µL aliquots of sterile, deionized, surfactant free HPLC grade water, allowing a droplet to rest on the surface for 1 minute each time. After the last wash, 3 µL of a MALDI matrix solution of 3 mg/mL α-cyano-4-hydroxycinnamic acid (CHCA) in a 1:1 mixture of acetonitrile and 0.1% trifluoroacetic acid (TFA) (v/v) can be used to extract analytes bound to the chip surface. 1 µL of the extract can be deposited onto a MALDI sample plate and allowed to dry before mass spectrometric analysis.

Mass Spectrometry:

MALDI-TOF can be performed using a Voyager-DE™ STR MALDI-TOF (Applied Biosystems) Mass Spectrometer equipped with a nitrogen laser emitting at 337 nm. Spectra are acquired in linear positive mode using a delayed extraction time of 700 nanoseconds and an accelerating voltage of 20 kV. 500-600 laser shots are typically averaged to produce the final sample spectrum.

Protein Sequence Studies:

Protein Assay: fractionated samples were assayed by a traditional Bradford assay using bovine serum albumin (BSA) standard ranging from 200 µg/mL to 1 mg/mL monitored at 595 nm on a UV-VIS spectrophotometer (Spectramax® Plus 384, Molecular Devices).

1D gel separation and digestion: 15 g of each bead fractionated sample and 3 µL of serum can be diluted in 30 µL of LDS sample buffer and boiled for 5 minutes at 95° C. The fractions can be run on a 1D pre-cast gel (4-12% Bis-tris) to isolate desired molecular weight regions of the complex protein mixture. Gels can then be washed thoroughly with dd$H_2O$, fixed in a 50% methanol/10% acetic acid solution for 30 minutes, stained with Sypro® ruby stain overnight, and destained in dd$H_2O$ for 3 hours prior to UV excitation and visualization. The gel can then be sliced into 1 mm² gel regions and the gel bands destained in 50% methanol. Gel bands can be reduced and alkylated with 10 mM DTT and 55 mM iodoacetamide, incubated at 4° C. for 1 hour in trypsin (20 ng/µL) and allowed to digest overnight (16 hours) at 37° C. in 25 mM $NH_4HCO_3$. The following morning, proteins can be extracted from the gel with repeated incubations of 70% ACN/5% formic acid solution.

LC/MS/MS analysis: Samples can be lyophilized to near dryness and reconstituted in 6.5 µL of HPLC buffer A (95% $H_2O$, 5% ACN, 0.1% FA) for Mass Spectrometry analysis. Microcapillary reverse phase LC/MS/MS analysis can be performed with Dionex's LC Packings liquid chromatography system coupled online to a ThermoFinnigan LCQ Classic ion trap mass spectrometer (San Jose, Calif.) with a modified nanospray source. Reverse phase separations were performed with an in-house, slurry packed capillary column. The $C_1$ silica-bonded column is 75 µm i.d., 360 µm o.d., 10 cm long fused silica packed with 5 µm beads with 300 Angstrom pores (Vydac, Hesperia, Calif.). A µ-precolumn PepMap, 5 mm, $C_{18}$ cartridge (Dionex) acts as a desalting column. Sample is injected in µL pick-up mode and washed with Buffer A for five minutes prior to a linear gradient elution with Buffer B (95% ACN/5% $H_2O$/0.1% formic acid) up to 85% over 95 minutes at a flow rate of 200 nL/minute. Full MS scans are followed by four MS/MS scans of the most abundant peptide ions (in a data dependant mode) and collision induced dissociation (CID) is performed at a collision energy of 38% with the ion spray voltage set to 2.00 kV, capillary voltage and temperature to 22.80 V and 180° C., respectively.

Data analysis: Data analysis was performed by searching MS/MS spectra against the European Bioinformatics Institute of the non-redundant proteome set of Swiss-Prot, TrEMBL and Ensembl entries through the Sequest Bioworks Browser (ThermoFinnigan). Peptides were considered legitimate hits after filtering the correlation scores (see Table 2) and manual inspection of the MS/MS data. The criteria used to filter data are at least as stringent as most literature citations.

TABLE 2

| Charge | $X_{corr}$ | DeltaCN | Ions | Rsp |
|---|---|---|---|---|
| +1 | >1.9 | >0.1 | >50% | =1 |
| +2 | >2.5 | >0.1 | >50% | =1 |
| +3 | >3.5 | >0.1 | >50% | =1 |

Accepted peptide hits are required to have an $X_{corr}$ ranking = 1 relative to all other peptides in the database.

REFERENCES

1. Folkman, J. Fundamental concepts of the angiogenic process. Curr Mol. Med. 2003 November; 3(7):643-51.
2. Affara N I, Robertson F M. Vascular endothelial growth factor as a survival factor in tumor-associated angiogenesis. In Vivo. 2004 September-October; 18(5):525-42.
3. L. A. Liotta, M. Ferrari, E. Petricoin "Clinical Proteomics: Written in Blood", Nature 425, 301, Oct. 30, 2003.
4. Terracciano R., Gaspari M., Testa F., Pasqua L., Cuda G., Tagliaferri P., Cheng M. C., Petricoin E. F., Liotta L. A., Ferrari M., Venuta S., "Selective Binding and Enrichment for Low Molecular Weight Biomarker Molecules in Human Plasma after Exposure to Nanoporous Silica Particles", Proteomics, Volume 6, Issue 11, Date: No. 11 Jun. 2006, Pages: 3243-3250.
5. Gaspari M, Cheng M C, Terraccianol R, Liu X, Nijdam A J, di Fabrizio E, Petricoin E F, Liotta L A, Cuda G, Ferrari M, Venutal S, "Nanoporous surfaces as harvesting agents for mass spectrometric analysis of peptides in human plasma" J. Proteome Res. 2006 May; 5(5): 1261-6.
6. Ferrara N, Hillan K J, Novotny W. Bevacizumab (Avastin), a humanized anti-VEGF monoclonal antibody for cancer therapy. Biochem Biophys Res Commun. 2005 Jul. 29; 333(2):328-35.

7. Sunia A. Trauger, Eden P. Go, Z Shen, Junefredo V. Apon, Bruce J. Compton, Edouard S. P. Bouvier, M. G. Finn, and Gary Siuzdak, High Sensitivity and Analyte Capture with Desorption/Ionization Mass Spectrometry on Silylated Porous Silicon" Analytical Chemistry, 76, 4484-4489 (2004).
8. E. F. Petricoin III et, al "Use of proteomic patterns in serum to identify ovarian cancer" Lancet 359 572-77 (2002).
9. D. Geho, N. Lahar, M. Ferrari, E. Petricoin, L. Liotta, "Opportunities for Nanotechnology-Based Innovation in Tissue Proteomics", Biomedical Microdevices, Vol. 6, No. 3, September, 2004, 231-240.
10. M. Ferrari, Cancer Nanotechnology; Opportunities and Challenges, Nature Reviews, Cancer, Vol. 5, n.3, pp. 161-171, 2005.
11. M. Ferrari, therapeutic microdevices and methods for making and using sames, U.S. Pat. No. 6,107,102.
12. Geho D, Cheng M C, Killian K, Lowenthal M, Ross S, Frogale K, Nijdam A J, Lahar N, Herrmann P, Johann D, Whiteley G, Ferrari M, Petricoin E, Liotta L, "Fractionation of Serum Components Using Nanoporous Substrates" Bioconjug. Chem. 2006 May-June; 17(3):654-61.
13. Walczak, et al., in preparation.
14. Martin F J, Melnik K, West T, Shapiro J, Cohen M, Boiarski A A, Ferrari M. Acute toxicity of intravenously administered microfabricated silicon dioxide drug delivery particles in mice: preliminary findings. Drugs R D. 2005; 6(2):71-81.
15. Ferrari M. Nanovector Therapeutics, Current Opinions in Chemical Biology, Vol. 9, No. 4, 343-346, 2005.
16. Cohen M H, Melnik K, Boiarski A A, Ferrari M, Martin F J. Microfabrication of Silicon-Based Nanoporous Particulates for Medical Applications, Biomedical Microdevices, Vol. 5, No. 3, September, 2003.
17. M. Ferrari, therapeutic microdevices and methods for making and using sames, U.S. Pat. No. 6,107,102.
18. Decuzzi P, Lee S, Bhushan B, Ferrari M. A Theoretical Model for the Margination of Nanoparticles within Blood Vessels. Annals of Biomedical Engineering, Vol. 33, No. 2, February 2005, pp. 179-190.
19. Nashat A H, Moronne M, Ferrari M. Detection of Functional Groups and Antibodies on Microfabricated Surfaces by Confocal Microscopy. Biotechnology and Bioengineering, Vol. 60 No. 2 pp. 137-146, 1998.
20. M. Zhang, T. Desai, and M. Ferrari, "Proteins and Cells on PEG Immobilized Silicon Surfaces," Biomaterials, Vol. 19, 1998, 953-960.
21. J. K. Tu, T. Huen, R. Szema, and M. Ferrari, "Filtration of Sub-100 nm Particles Using a Bulk-Micromachined, Direct-Bonded Silicon Filter", Biomedical Microdevices, Vol. 1, No. 2, 113-120, 1999.
22. Nijdam A J, Cheng M C, Geho D H, Fedele R, Herrmann P, Killian K, Espina V, Petricoin E P, Liotta L A, Ferrari M, "Physicochemically Modified Silicon as Candidate Substrate for Protein Microarrays", Biomaterials. 2007 January; 28(3):550-8. Epub 2006 Sep. 20.
23. Crouch M F, Davy D A, Willard F S, Berven L A Insulin induces epidermal growth factor (EGF) receptor clustering and potentiates EGF-stimulated DNA synthesis in Swiss 3T3 cells: a mechanism for costimulation in mitogenic synergy. Immunol Cell Biol. 2000. 78(4):408-414.
24. Kute T E and Quadri Y. Measurement of proliferation nuclear and membrane markers in tumor cells by flow cytometry. J. Histochem. Cytochem. 1991. 39(8):1125-1130.

Example 5

Nanoporous Particles for Proteolytic Fragment Harvesting

The development of approaches using the combination of nanotechnology and Mass Spectrometry (MS) holds the promise of rapidly identifying known and novel proteins within the low-molecular weight proteome (LMWP; <20 kDa or <15 kDa) present in serum of patients with breast cancer. Challenges of such task can be diminishing masking effects of larger serum carrier proteins, such as albumin, while increasing the concentration of lower molecular weight, lower abundance proteins, which may be useful for detection and diagnosis of a disease such as a breast cancer, as predictors of prognosis or evaluation of an individual patient's response to different types of therapy. In these studies, nano-textured silica/silicon based chips have been developed, which have specific pore sizes and have specific surface characteristics, such as either positive, or negative charge or hydrophobic characteristics, that can differentially enhance adsorption of proteins within different molecular weight ranges that are present in serum isolated from nude mice bearing human breast tumor xenografts. Serum was isolated from human MCF-7/Cyclooxygenase-2 (MCF-7/Cox-2) breast tumor xenografts which produce 50-fold greater levels of prostaglandin E2 (PGE2) and 5-fold increased estradiol levels compared to MCF-7/vector control cells. MCF-7/Cox-2 human breast tumor cells were injected into the mammary fat pad of female 8-10 week old ovariectomized nude mice implanted with sustained release pellets of beta-estradiol. At days 15, 28, 42 and 60 after tumor cell injection, blood was isolated by cardiac puncture and processed to isolate serum samples, eluted onto nanochips, which were then combined with Matrix-assisted laser desorption/ionization-Time of Flight (MALDI-TOF) proteomic analysis and Mass Spectrometry/Microsequencing (MS/MS). At the same time points, breast tumor xenografts were measured and isolated for proteomic analysis and for histological evaluation. These studies demonstrate a utility of silica/silicon nanochips with specific surface characteristics in combination with MS approaches to provide reproducible and sensitive spectral portraits of low molecular weight proteins in serum of mice bearing human breast tumor xenografts as well as for sensitive detection of proteins produced by breast tumors during their early stages of development, invasion, and metastasis. Thus far, 79 unique proteins have been identified within the LMWP of serum isolated from mice bearing human tumor xenografts.

Experiments Design and Method

TEST ANIMALS Blood can be collected from mice according to the following schedule established for tumor development.

Samples include:
15 control mice-0.8-1.5 ml blood (0.4-0.75 ml serum)
15 mice bearing human breast tumor xenografts for 28 days-0.8-1.5 ml blood (0.4-0.74 ml serum)
15 mice bearing human breast tumor xenografts for 42 days-0.8-1.5 ml blood (0.4-0.74 ml serum)
15 mice bearing human breast tumor xenografts for 60 days-0.8-1.5 ml blood (0.4-0.74 ml serum)

All analysis can be carried out on serum obtained from the blood samples.

Serum Collection and Storage

Blood can be obtained by cardiac puncture and collected in red top tubes, allowed to coagulate at 4° C. for 2 hours, and the clot removed.

Serum from each mouse can be collected after centrifugation and aliquoted into cryoviles for storage at −80° C. as follows. Mice from each time point can be divided into three groups at random A, B, and C, each containing 5 mice. After serum collection, equal volume of serum collected from each mouse in group A (A1, A2, A3, A4, and A5) can be pooled, and stored in 100 µl aliquots. A similar set of samples can be collected from animals in groups B and C. Pooled sera from groups A, B, and C can be used for analysis and incubation with the nanobeads. All of the analysis can be carried out on samples thawed directly from frozen stocks, and samples undergoing a second or repeated freeze thaw cycles can not be considered as part of these studies.

Sample Distribution and Processing.

400 µl of the pooled serum collected can be used for experiments. The remaining pooled sera can be stored at −80° C., and utilized for subsequent analysis.

Sample Storage.

Serum from each mouse can be collected after centrifugation and aliquoted into cryoviles for storage at −80° C. as follows. All of the analysis can be carried out on samples thawed directly from frozen stocks. Serum samples designated for processing and analysis can be shipped on dry ice.

Incubation with Nanoporous Beads (MW Cut Off 16 kDa)

Aliquots of raw serum (20 µl) can be thawed and diluted (1:5) by the addition of 80 µl of deionized water (total sample volume 100 µl). The diluted serum can be incubated with 1 mg of nanobeads, which were prewashed 4× with deionized water, at RT for 1 hour (samples can be monitored during incubation for bead suspension, and as necessary nanobeads can be resuspended in the diluted serum every 15 minutes during the incubation). Following the incubation, the beads can be separated from the serum by microfuge centrifugation (30 sec, 10,000 rpm), the bead depleted diluted serum can be removed for analysis and/or storage at −80° C., and the beads can be washed 3 times with 100 µl of 0.1% TFA in deionized water (5 minutes each at RT). After the final wash, beads can be incubated with 80 µl of acetonitrile/0.1% TFA (75:25) for 30 min at RT, and the eluate removed, aliquoted, and stored at −80° C. This procedure can be followed for each of the different nanobeads to be examined.

Each of the serum samples collected can be incubated with a total of 12 different nanobead preparations including: particles with pore sizes of 7 nm or 20 nm; particles with different chemistry oxide, $NH_2$, PEG-NHS; and particles with diameters 5 µm or 20 µm. Complete analysis of a single serum sample with the complete series of nanobeads can require approximately 300 µl of serum (12 beads×25 µl serum/incubation).

SELDI Analysis of Samples

SELDI-TOF mass spectra can be obtained for each of the pooled serum samples and compared to spectra of the nanobead depleted serum and the nanobead eluate. Weak cation exchange chips (WCX2 ProteinChips, Ciphergen Biosystems, Inc.) can be used to obtain profiles of bound proteins. Chips can be processed as follows. Chips placed in a bioreactor can be incubated with 100 µl of 10 mM HCl for 5 min at room temperature (RT). Following aspiration of the HCL, the chip spot can be washed 2× in 100 µl deionized water 1 min each at RT. The chip is then incubated 2× in 100 µl of 10 mM ammonium acetate containing 0.1% Triton X-100 for 5 min each. The final ammonium acetate rinse is aspirated and the chips allowed to dry. 5 µl of sample is then applied to the chip spots and incubated for 55 min in a humidified chamber at RT. The chips are washed with 3 changes of phosphate buffered saline (150 µl each), followed by a single rinse in 150 µl of deionized water. After drying, two applications of 1.0 µl of a 30% solution of cinnaminic acid in 50% (v/v) acetonitrile, 0.5% trifluoroacetic acid is applied to each spot with drying between applications. After drying the chips are examined using a PBS-II mass spectrometer (Ciphergen Biosystems, Inc.) Spectra can be acquired under identical conditions for comparative purposes. Spectra can be collected using the following instrument settings: using a detector voltage of 1,800 V, focus mass of 6,000 Da, with a high limit of 20,000 Da, sensitivity gain set to 5, and laser intensity of 145. 15 laser shots can be acquired per position (ranging from 20 to 80), at 5 position increments.

SELDI spectra can also be collected after spotting 5 µl of diluted raw serum (1:5 with deionized water) analogous to serum prior to nanobead incubation, and from 5 µl of diluted serum following incubation with each nanobead (nanobead depleted serum) to directly compare the intensity and profile of serum protein peaks before and after bead incubation. These spectra can be compared to SELDI spectra obtained from an equivalent volume of each nanobead eluate (4 µl total).

Protein Analysis of Bead Eluate

Protein concentration in the nanobead eluate can be determined using standard microprotein assays (Bradford or BCA assay) using bovine serum albumin (BSA) as the protein standard.

1D Gel Separation

Following protein determination, samples can be analyzed by 1D gel separation. 15 µg of each nanobead eluate fraction can be incubated in 30 µl of SDS sample buffer and boiled for 5 min at 95° C. The fractions can then be separated by 1D electrophoresis using precast gels (4-12% Bis-Tris). Following electrophoresis, the gels can be washed in deionized water, fixed in 50% methanol/10% acetic acid solution for 30 min, and stained with Sypro® ruby stain overnight. The gels can be destained for 3 hours in deionized water prior to imaging using a Versadoc 3000 image analysis system. Regions of the gel below 20 kDa can be examined and bands selected for coring using a BioRad gel spotcutter. Excised gel pieces are placed in a 96-well multiplate. Gel pieces can be transferred to the CCC Proteomics Core for processing and analysis by LC/MS/MS.

LC/MS/MS

Gel pieces can be washed in 50% methanol/5% acetic acid for one hour. The wash step can be repeated once before gel pieces are dehydrated in acetonitrile. The gel pieces can be rehydrated in 10 mM dithiothreitol (DTT) in 0.1 M ammonium bicarbonate and reduced at room temperature for 0.5 h. The DTT solution can be removed and the sample can be alkylated with 50 mM iodoacetamide in 0.1 M ammonium bicarbonate at room temperature for 0.5 h. The iodoacetamide reagent can be removed and the gel pieces are washed with 100 mM ammonium bicarbonate before drying in acetonitrile in 5 minute increments. The gels can be again washed in 100 mM ammonium bicarbonate for 5 min. prior to dehydration with acetonitrile for 5 min. The gels can be dried for 5 min. The protease can be driven into the gel pieces by rehydrating them in 25 µL of sequencing grade modified trypsin at 20 µg/mL in 50 mM ammonium bicarbonate for 10 min prior to the addition of 20 µL of 50 mM ammonium bicarbonate. The sample is incubated at 40° C. for 6 h. The peptides that are formed are extracted from the polyacrylamide with two 20 min washes of 50% acetonitrile/5% formic acid. These extracts are combined in a clean 96-well multiplate and dried for 90 min.

Capillary-liquid chromatography-nanospray tandem mass spectrometry (Nano-LC/MS/MS) can be performed on a Thermo Finnigan LTQ mass spectrometer equipped with a nanospray source operated in positive ion mode. The LC system can be a UltiMate™ Plus system from LC-Packings A Dionex Co (Sunnyvale, Calif.) with a Famous autosampler and Switchos column switcher. The solvent A can be water containing 50 mM acetic acid and the solvent B can be acetonitrile. 5 microliters of each sample can be first injected on to the trapping column (LC-Packings A Dionex Co, Sunnyvale, Calif.), and washed with 50 mM acetic acid. The injector port can be switched to inject and the peptides can be eluted off of the trap onto the column. A 5 cm 75 mm ID ProteoPep II C18 column (New Objective, Inc. Woburn, Mass.) packed directly in the nanospray tip can be used for chromatographic separations. Peptides can be eluted directly off the column into the LTQ system using a gradient of 2-80% B over 30 minutes, with a flow rate of 300 nl/min. A total run time can be 58 minutes. The scan sequence of the mass spectrometer can be programmed for a full scan, a zoom scan to determine the charge of the peptide and a MS/MS scan of the most abundant peak in the spectrum. Dynamic exclusion can be used to exclude multiple MS/MS of the same peptide.

Sequence information from the MS/MS data can be processed using Mascot Distiller to form a peaklist and by using Turbo SEQUEST algorithm in BioWorks 3.1 Software. Data processing can be performed following the guidelines in Molec. Cell. Proteomics. Assigned peaks have a minimum of 10 counts (S/N of 3). The mass accuracy of the precursor ions can be set to 1.5 Da to accommodate accidental selection of the C13 ion and the fragment mass accuracy can be set to 0.5 Da. Considered modifications (variable) were methionine oxidation and carbamidomethyl cysteine.

Experimental Results

I Mass Spectrometry MALDI-TOF

Nanoporous were beads used for these experiments.

4×12 aliquots of silica beads were available (4 different surface chemistries: silica small and large pore, APTES and MPTMS small pore)

MALDI-TOF Analysis Protocol

Extracted peptides were mixed with an α-cyano-4-hydroxycinnamic acid (CHCA) solution, 4 mg/mL in 50% (v/v) acetonitrile, 0.1% TFA. Matrix/sample ratio is specified for each single experiment. 1 µl of the sample/matrix solution was spotted on a stainless steel MALDI target plate and air-dried. MALDI-TOF spectra were acquired on a Voyager-DEL STR mass spectrometer (Applied Biosystems, Framingham, Mass.) in delayed extraction, linear positive ion mode using the following settings: accelerating voltage 20,000 V, grid voltage 91.5%, extraction delay time 200 nsec, acquisition mass range 800-20,000 m/z, laser intensity range 2100-2300. Each spectrum was the average of 400-1000 individual laser shots acquired in series of 100 consecutive shots. External instrument calibration was performed daily using a mixture of standard peptides (Applied Biosystems calmix 2+calmix 3). A linear 6-point calibration was used (approx. Mw: 1300, 2090, 3600, 5700, 8100, 11000 Da).

Optimization of the Protocol for MS MALDI Spotting

Figure 19:
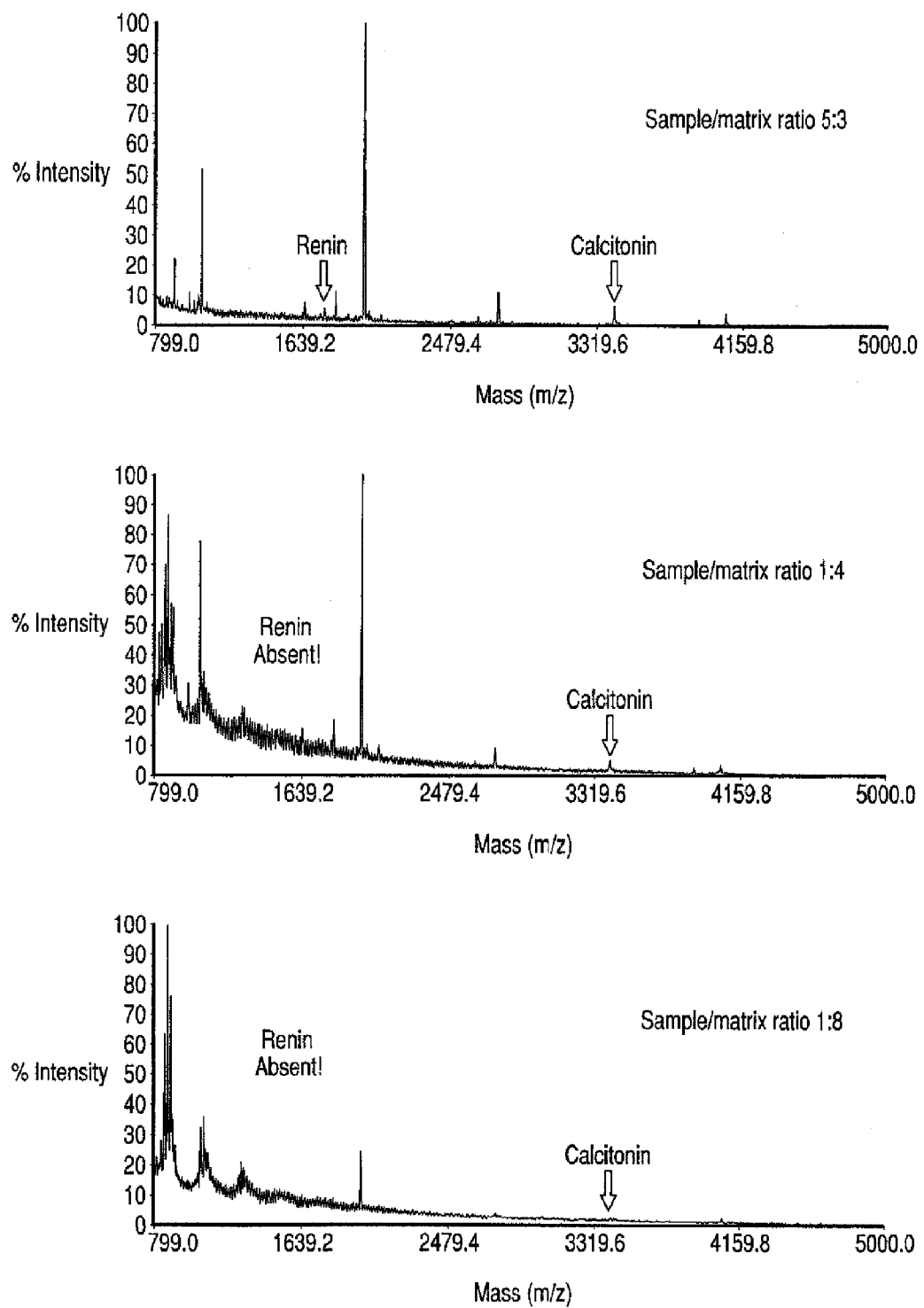
FIG. 19 shows MALDI-TOF mass spectra for three different sample/matrix MALDI preparation.

Three different sample/matrix ratios were tested: (i) 1:8; (ii) 1:4; and (iii) 5:3. Mouse control serum spiked with 200 ng/mL of two standard peptides, renin and calcitonin was analyzed. The three spectra in FIG. 19 indicate that 5:3 ratio may be the best experimental setting in view of the following factors: (i) number of detectable peaks in the spectrum from mouse serum; (ii) overall absolute intensity of peaks; and (iii) signal-to-noise ratio of spiked peptides (calcitonin and renin).

An alternative protocol aiming at sensitivity improvement was also tested. Silica small pore beads were used. After the last washing, 4 µL of MALDI matrix solution was added to the beads, and 1.5 µL of the resulting suspension was spotted onto the MALDI target plate. Resulting MALDI-TOF spectra gave superior signal intensity with respect to a standard dried droplet preparation.

As (i) the presence of beads in the matrix suspension may affect uniformity of matrix crystallization and may worsen mass accuracy of the measurement; (ii) introducing silica particles in the mass spectrometer may cause some performance loss with time due to deposition of these particles in the inside of the mass spectrometer (voltage grids, etc.), it was decided to adopt standard extraction conditions and 5:3 sample/matrix ratio for subsequent analyses of mouse sera.

Figure 20:
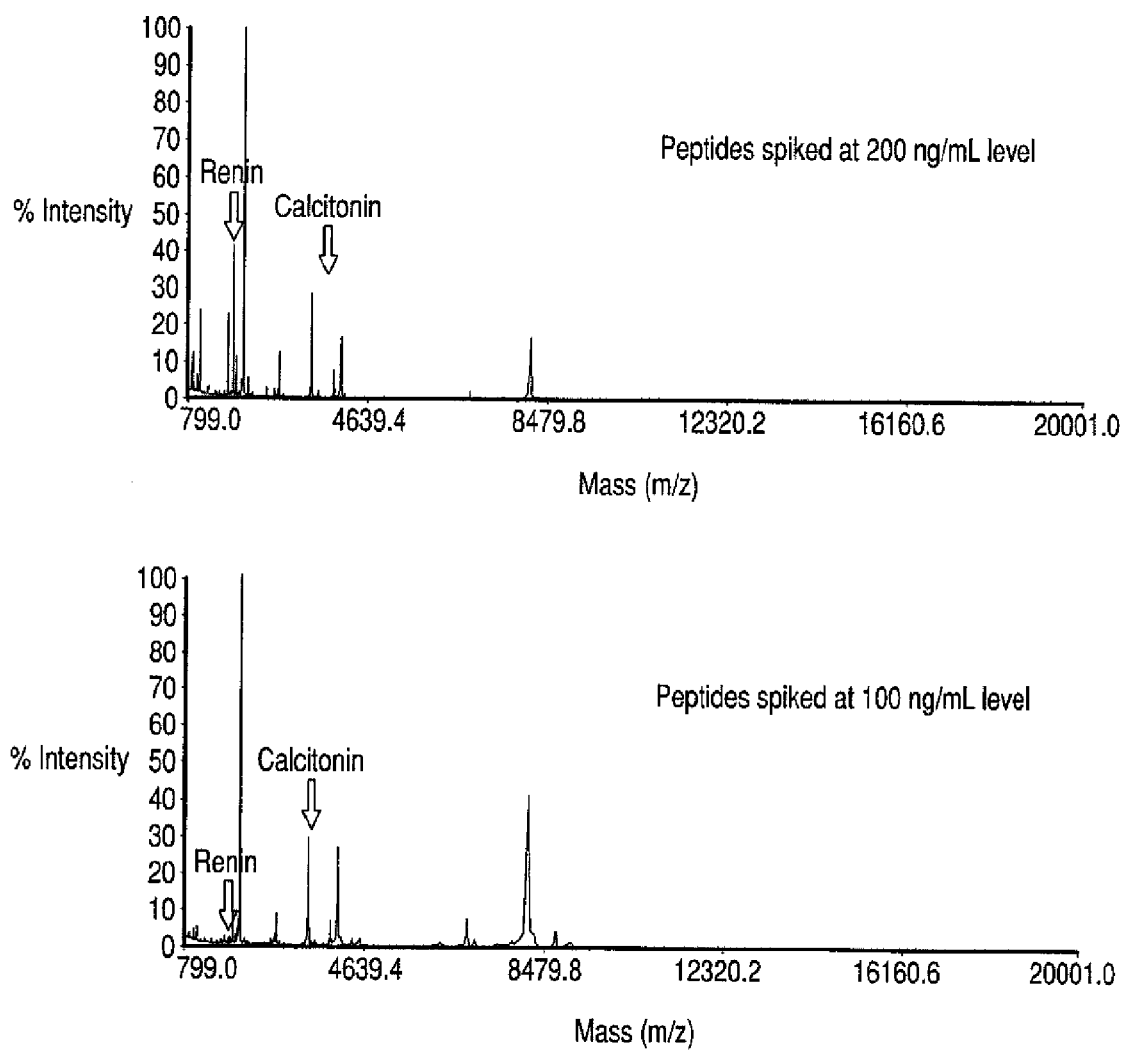
FIG. 20 shows MALDI-TOF mass spectra of control mouse serum.

Here below, MALDI-TOF spectra of control mouse serum obtained with the described method are reported. Two different peptide spiking were performed in order to have an additional reference peak for comparison to other MALDI preparations, see, for example, FIG. 20. Signal intensity from calcitonin (100 ng/mL spiked in mouse serum) is higher than with the standard preparation method.

Incubation of Control Serum Samples with Nanoporous Beads

The following protocol was adopted for mouse serum analysis.

Beads pre-washing: 4×100 µL $H_2O$.

Incubation: 100 µL of diluted serum with 1 mg beads, 1 hour at RT.

Washings of beads: 2×100 µL $H_2O$, followed by a single 100 µL wash in 0.1% TFA.

Extraction: 80 µL of 75/25 $CH_3CN$/0.1% TFA, 30 minutes incubation at RT.

MALDI preparation: sample/matrix ratio of 5:3.

MALDI-TOF analysis as described earlier in this example.

Spectra shown in FIG. 21 were acquired on mouse control serum using four different beads (silica small and large pore, APTES small pore and MPTMS small pore).

Experiments on Reproducibility.

To assess a reproducibility of the beads preparation, five replicate incubations of mouse control serum were undertaken using 5× large pore silica beads kits. Duplicate MALDI-TOF analyses for each incubation yielded 10 spectra. The 28 highest intensity peaks automatically detected by the peak picking software (Applied Biosystems), which were common to all 10 spectra, were used for statistical analysis. After normalization on the total signal intensity (peak height), coefficients of variation for the normalized intensities were calculated (28 peaks, 10 replicates). Results are reported in Table 3, together with a typical MS spectrum obtained. Average CV on m/z determination was 0.02%. Average CV on peak height was 21.8.

TABLE 3

Peak height for ten replicate experiments (5 replicate incubations, duplicate MALDI-TOF analyses) of silica beads LMWP harvesting and MS analysis.

| Peak m/z | CV on m/z value | Peak height in exp 1 | Peak height in exp 2 | Peak height in exp 3 | Peak height in exp 4 | Peak height in exp 5 | Peak height in exp 6 | Peak height in exp 7 | Peak height in exp 8 | Peak height in exp 9 | Peak height in exp 10 | Average peak height | CV value |
|---|---|---|---|---|---|---|---|---|---|---|---|---|---|
| 905.4 | 0.05 | 491 | 541 | 528 | 470 | 398 | 393 | 475 | 502 | 462 | 476 | 473 | 10.2 |
| 1061.6 | 0.04 | 2623 | 2863 | 2768 | 2696 | 2844 | 2738 | 2655 | 3123 | 2168 | 2571 | 2705 | 9.1 |
| 1823.2 | 0.02 | 277 | 289 | 353 | 320 | 383 | 384 | 411 | 373 | 519 | 533 | 384 | 22.5 |
| 1979.5 | 0.02 | 2260 | 1897 | 2496 | 2625 | 3290 | 3293 | 2972 | 2740 | 2805 | 2655 | 2703 | 16.0 |
| 2082.4 | 0.02 | 373 | 473 | 308 | 297 | 644 | 605 | 474 | 595 | 300 | 332 | 440 | 31.1 |
| 2482.5 | 0.02 | 51 | 44 | 72 | 61 | 74 | 79 | 85 | 67 | 65 | 69 | 67 | 18.6 |
| 2640.2 | 0.01 | 40 | 38 | 51 | 47 | 31 | 33 | 42 | 36 | 41 | 37 | 40 | 15.4 |
| 2707.9 | 0.02 | 62 | 51 | 59 | 68 | 52 | 44 | 59 | 48 | 46 | 40 | 53 | 17.0 |
| 2755.5 | 0.02 | 150 | 153 | 167 | 159 | 118 | 134 | 172 | 126 | 147 | 132 | 146 | 12.1 |
| 2822.5 | 0.01 | 31 | 29 | 45 | 38 | 37 | 40 | 42 | 36 | 46 | 40 | 38 | 14.4 |

TABLE 3-continued

Peak height for ten replicate experiments (5 replicate incubations, duplicate MALDI-TOF analyses) of silica beads LMWP harvesting and MS analysis.

| Peak m/z | CV on m/z value | Peak height in exp 1 | Peak height in exp 2 | Peak height in exp 3 | Peak height in exp 4 | Peak height in exp 5 | Peak height in exp 6 | Peak height in exp 7 | Peak height in exp 8 | Peak height in exp 9 | Peak height in exp 10 | Average peak height | CV value |
|---|---|---|---|---|---|---|---|---|---|---|---|---|---|
| 3413.6 | 0.01 | 319 | 322 | 273 | 275 | 172 | 195 | 212 | 167 | 345 | 304 | 258 | 25.7 |
| 3497.9 | 0.01 | 137 | 141 | 118 | 121 | 74 | 86 | 83 | 76 | 142 | 116 | 109 | 24.9 |
| 3581.1 | 0.02 | 55 | 49 | 81 | 72 | 48 | 48 | 68 | 60 | 71 | 59 | 61 | 18.8 |
| 3907.3 | 0.02 | 41 | 39 | 46 | 42 | 70 | 69 | 55 | 46 | 84 | 76 | 57 | 28.9 |
| 4040.6 | 0.02 | 89 | 76 | 71 | 67 | 51 | 49 | 59 | 55 | 66 | 50 | 63 | 20.3 |
| 4061.8 | 0.02 | 688 | 615 | 511 | 641 | 410 | 418 | 544 | 446 | 460 | 402 | 513 | 20.3 |
| 4069.1 | 0.02 | 266 | 250 | 231 | 273 | 134 | 145 | 197 | 189 | 178 | 144 | 201 | 25.9 |
| 4104.8 | 0.02 | 175 | 160 | 127 | 133 | 107 | 120 | 72 | 106 | 120 | 104 | 122 | 24.0 |
| 4283.8 | 0.02 | 30 | 30 | 34 | 30 | 27 | 26 | 31 | 25 | 28 | 29 | 29 | 8.0 |
| 4360.9 | 0.02 | 24 | 30 | 40 | 29 | 23 | 26 | 36 | 28 | 41 | 37 | 31 | 21.2 |
| 4533.2 | 0.02 | 91 | 81 | 54 | 55 | 44 | 45 | 47 | 47 | 47 | 45 | 56 | 30.0 |
| 6785.5 | 0.03 | 36 | 38 | 54 | 38 | 26 | 28 | 31 | 28 | 66 | 56 | 40 | 34.7 |
| 6827.8 | 0.02 | 400 | 467 | 399 | 364 | 223 | 276 | 301 | 226 | 579 | 563 | 380 | 33.7 |
| 6996.2 | 0.02 | 148 | 174 | 165 | 134 | 79 | 87 | 96 | 80 | 218 | 199 | 138 | 37.0 |
| 8125.5 | 0.03 | 877 | 866 | 707 | 749 | 485 | 474 | 654 | 603 | 723 | 696 | 683 | 20.0 |
| 8212.2 | 0.02 | 180 | 195 | 154 | 127 | 102 | 108 | 67 | 110 | 156 | 158 | 136 | 29.1 |
| 8571.1 | 0.03 | 32 | 31 | 40 | 32 | 24 | 26 | 28 | 29 | 36 | 36 | 31 | 15.8 |
| 9069.6 | 0.03 | 54 | 60 | 48 | 39 | 30 | 31 | 32 | 33 | 40 | 41 | 41 | 25.4 |

II Mass Spectrometry SELDI
Processing of Serum From Tumor Bearing Animals:
Pooled serum samples were provided from 12 sets of animals as follows:
1. Control serum pool A
2. Control serum pool B
3. Control serum pool C
4. Day 28 tumor bearing serum (tumors derived from MCF7 cell clone 8)
5. Day 28 tumor bearing serum (tumors derived from MCF7 cell clone 10)
6. Day 42 tumor bearing serum (tumors derived from MCF7 cell clone 8)
7. Day 42 tumor bearing serum (tumors derived from MCF7 cell clone 10)
8. Day 60 serum negative control (animals injected with matrigel)
9. Day 60 tumor bearing serum control 1 (tumors derived from cell line BT-474)
10. Day 60 tumor bearing serum control 2 (tumors derived from baseline MCF7 cell line)
11. Day 60 tumor bearing serum (tumors derived from MCF7 cell clone 8)
12. Day 60 tumor bearing serum (tumors derived from MCF7 cell clone 10) 6 bead sets were used for incubation with the pooled sera samples. Each set of beads contained 12 individual bead kits, one kit for each of the 12 serum pools. The bead sets used were as follows:

Set A. 10 μm diameter, small pore, silica
Set B. 10 μm diameter, small pore, APTES derivatized, (+) charged
Set C. 10 μm diameter, small pore, MPTMS derivatized, (−) charged
Set D. 10 μm diameter, large pore, silica
Set E. 10 μm diameter, large pore, APTES derivatized, (+) charged
Set F. 10 μm diameter, large pore, MPTMS derivatized, (−) charged Serum samples were incubated with the bead kits as follows. All bead kits were first washed 4 times in HPLC grade water prior to incubation with the serum. Serum samples were thawed and diluted 1:5 with HPLC grade water, and 100 μl of diluted serum was incubated with the bead kit for 1 hour at room temperature. For example, 100 μl of diluted serum sample 1 above (pooled control serum A) was incubated with each of the six bead types A through F, giving samples 1 through 6 respectively (see Table 4). Similarly, each of the remaining 12 serum samples were also incubated with each of the separate bead sets, yielding a total of 72 samples (see Table 4).

After the incubation with the serum, the beads were pelleted, and the depleted serum removed. The beads were then washed in HPLC grade water 2×, and 0.1% TFA 1×, before elution for 30 minutes in 0.1% TFA/acetonitrile (25:75) at room temperature. Final eluates (80 μl) were collected (72 total samples, see Table 4) and stored at −80° C. until processed further.

TABLE 4

Key to bead samples and eluates (sample number)

| | BEAD | | | | | |
|---|---|---|---|---|---|---|
| SERUM SAMPLE | Small pore silica | Small Pore APTES | Small Pore MPTMS | Large pore silica | Large pore APTES | Large pore MPTMS |
| Control pool A | 1 | 2 | 3 | 4 | 5 | 6 |
| Control pool B | 7 | 8 | 9 | 10 | 11 | 12 |
| Control pool C | 13 | 14 | 15 | 16 | 17 | 18 |
| Day 28 pool, MCF7 clone 8 | 19 | 20 | 21 | 22 | 23 | 24 |
| Day 28 pool, MCF7 clone 10 | 25 | 26 | 27 | 28 | 29 | 30 |

TABLE 4-continued

Key to bead samples and eluates (sample number)

| | BEAD | | | | | |
|---|---|---|---|---|---|---|
| SERUM SAMPLE | Small pore silica | Small Pore APTES | Small Pore MPTMS | Large pore silica | Large pore APTES | Large pore MPTMS |
| Day 42 pool, MCF7 clone 8 | 31 | 32 | 33 | 34 | 35 | 36 |
| Day 42 pool, MCF7 clone 10 | 37 | 38 | 39 | 40 | 41 | 42 |
| Day 60 pool, matrigel control | 43 | 44 | 45 | 46 | 47 | 48 |
| Day 60 pool, BT-474 control | 49 | 50 | 51 | 52 | 53 | 54 |
| Day 60 pool, MCF7 control cell line | 55 | 56 | 57 | 58 | 59 | 60 |
| Day 60 pool, MCF7 clone 8 | 61 | 62 | 63 | 64 | 65 | 66 |
| Day 60 pool, MCF7 clone 10 | 67 | 68 | 69 | 70 | 71 | 72 |

Eluates were thawed 5 days after the incubation and 60 µl of the eluate removed and concentrated in the SpeedVav to ~25 µl total volume for 1D gel analysis. Both the concentrated eluate and remaining original eluate samples were stored at −80° C. until processed further for 1D gel and SELDI analysis respectively.

All of the concentrated bead eluates were mixed with SDS-PAGE sample buffer, and separated on an 8-16% Tris-glycine gradient gel and stained with Sypro ruby. After destaining, gels were imaged using a BioRad Versadoc system. Gel results are presented in FIGS. 22 through 30.

Eluate Gel Protein Band Excision for Tandem Mass Spectroscopy.

The 1D SDS-PAGE gels of the bead eluates showed similar protein banding patterns, see FIGS. 22-27. Analysis of the gels did not reveal any new pattern of protein bands that can be attributed to sera from the tumor bearing animals in comparison to the pooled sera from the three control animal samples. It was also noted that protein load varied from sample to sample with some individual lanes containing significantly higher amount of protein (see Gel 6, lane 8 (sample 42 in Table 4). Based upon these results, 90 bands were identified for excision and submission for identification by tandem mass spectrometry.

Gel 6, which separated the eluates samples obtained from the large pore MPTMS beads was selected for the most complete analysis. Four low molecular weight bands were excised from each lane to determine if the protein composition of the band changed with respect to the bead, and all of the major bands present in lane 8 (sample number 42 corresponding to pooled serum collected from day 42 clone 10 tumor bearing animals). Additional low molecular weight bands were excised from gel 4, large pore APTES modified beads, lanes 12 and 13, which corresponded to the pooled serum collected from day 60 tumor bearing animals from clone 8 and 10 respectively. Finally, additional bands from top to bottom of the gel were excised from lane 6 of gel 5, which corresponded to the eluates obtained from small pore MPTMS beads, sample number 27 (serum collected from day 28 clone 10 animals). Bands were identified and excised using a BioRad Gel cutting robot. Excised samples were deposited into wells of a 96 well microtitre plate and delivered to the CCIC proteomics core for tandem mass spectroscopy. The patterns of gel excision are shown in FIGS. 28, 29 and 30 along with the key in Table 4.

Protein identification results that were obtained from the tandem mass spectroscopic analysis of these samples is reported by the CCIC proteomics core elsewhere in this Example.

SELDI Analysis of Pooled Serum.

Pooled serum samples were removed from storage at −80° C., thawed, and a 150 µl aliquot of raw serum was removed and diluted by the addition of 600 µl HPLC grade water to give a stock 1:5 diluted serum sample. 25 µl of the diluted raw serum was removed, flash frozen in liquid nitrogen and placed in storage at −80° C. until processed for SELDI analysis. WCX2 chips were loaded into the Bioreactor, and sample spots were washed with 100 µl of 10 mM HCl for 5 min at RT. The solution was aspirated, and spots were washed 2× in 100 µl HPLC grade water for 1 min each rinse. The spots were then washed 2× in 100 µl of 10 mM ammonium acetate+0.1% Triton X-100 for 5 minutes each rinse. After the final buffer was aspirated, the WCX2 chips were removed from the Bioreactor and allowed to air dry at RT. The dried WCX2 chips were placed in the Bioreactor and 5 µl of diluted serum samples were added to the sample spots and the chips were incubated for 55 minutes at RT in a humidified chamber. The WCX2 chip spots were washed with 150 µl of PBS 3×, after the 55 minute incubation with the serum samples. Each spot was then rinsed with 150 µl of HPLC grade water, and the chip was removed from the Bioreactor and allowed to air dry at RT. Matrix (1 µl of alpha-CHCA in 50% acetonitrile and 0.5% TFA) was applied to each spot and dried. Matrix application was repeated, and the chip analyzed in the PBSII SELDI mass spectrometer. Resulting SELDI spectra are presented in FIGS. 31 through 33.

SELDI Analysis of Bead Eluates.

The eluate material recovered from each of the bead incubations were examined using a SELDI GoldChip. Eluate sample (1 µl) was applied to the chip spot and allowed to air dry. Matrix was added as described above and the sample was analyzed using the following instrument parameters. Eluate AU chip reading parameters at the LMW range were the same as indicated in the protocol for WCX2 chip analysis. Sample sets were analyzed in the same sequence as applied to the 1D SDS-PAGE gradient gels above. All 72 eluate samples have been analyzed, and duplicate spectra have been obtained.

Key to SELDI Spectra of Bead Eluates.

Figure 34A:
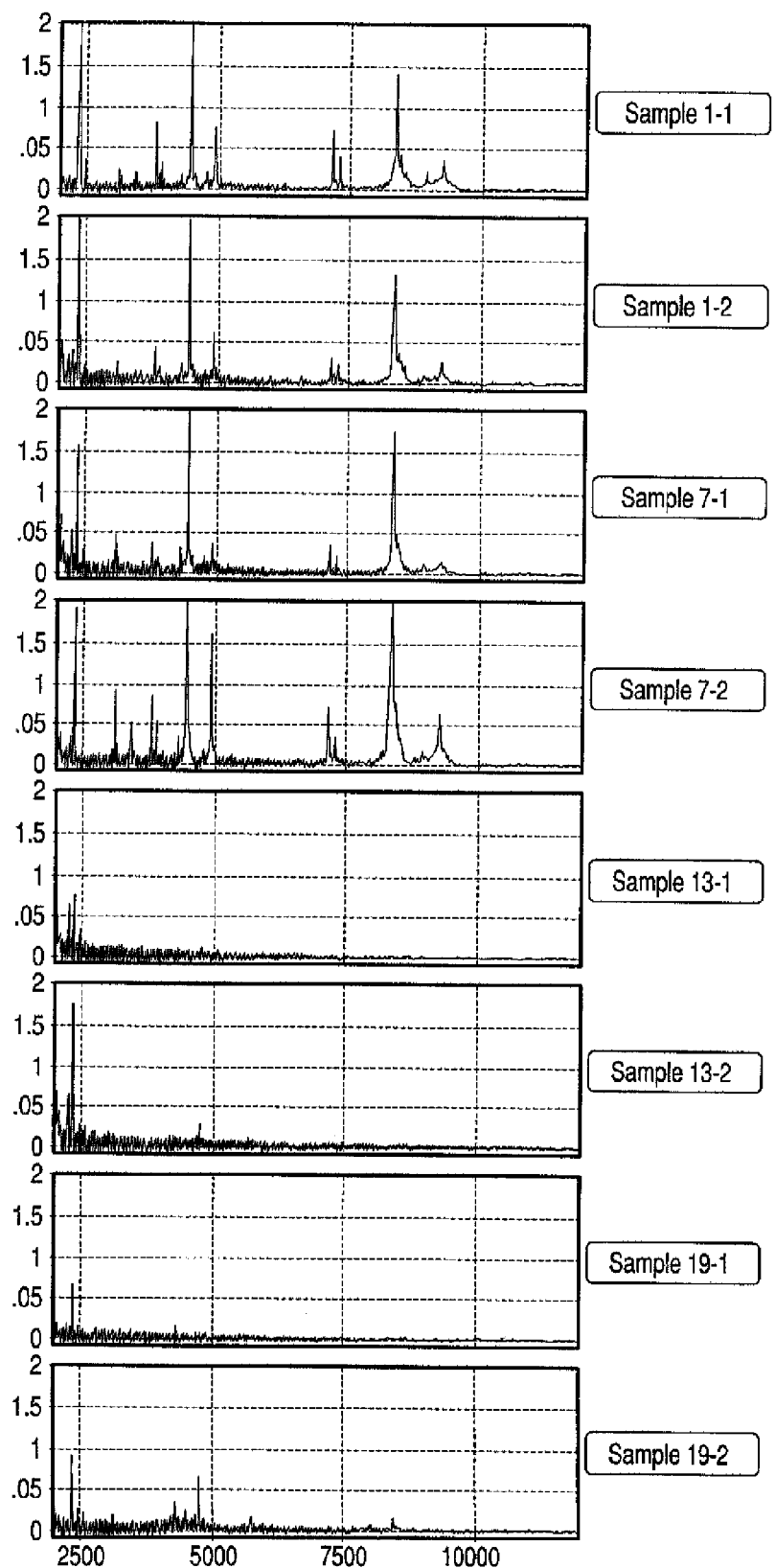
Figure 34B:
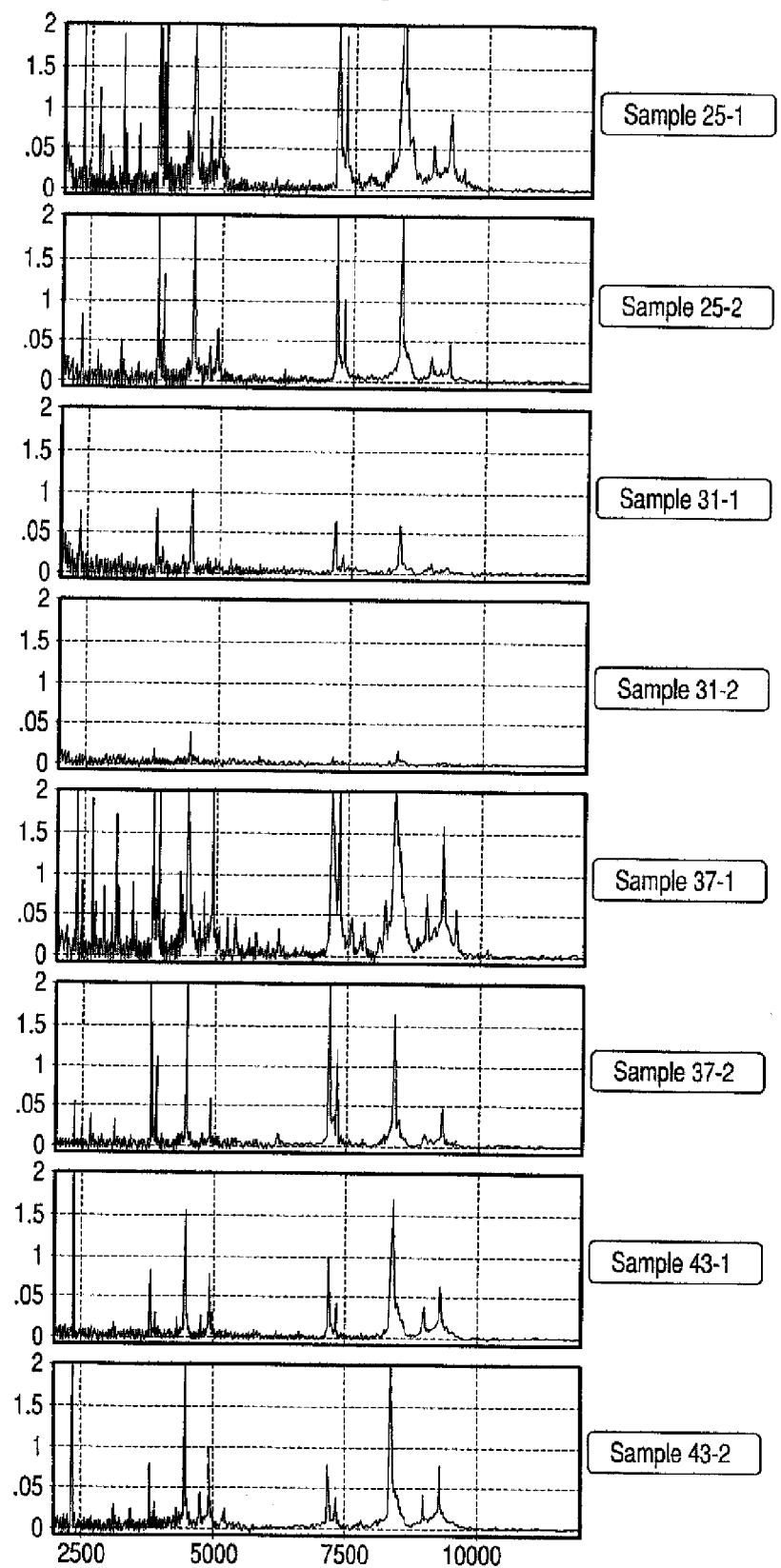
Figure 34C:
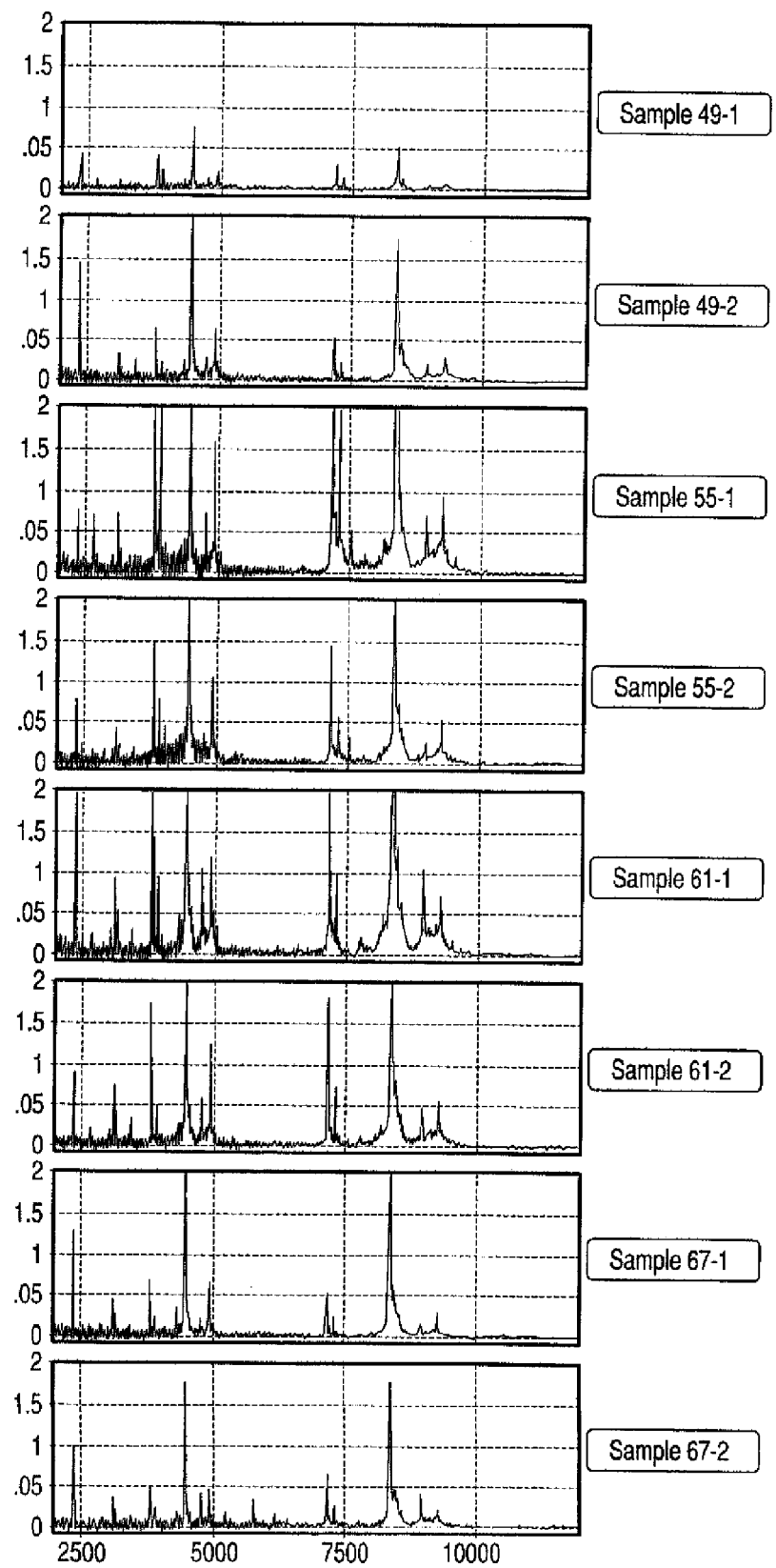
Figure 35A:
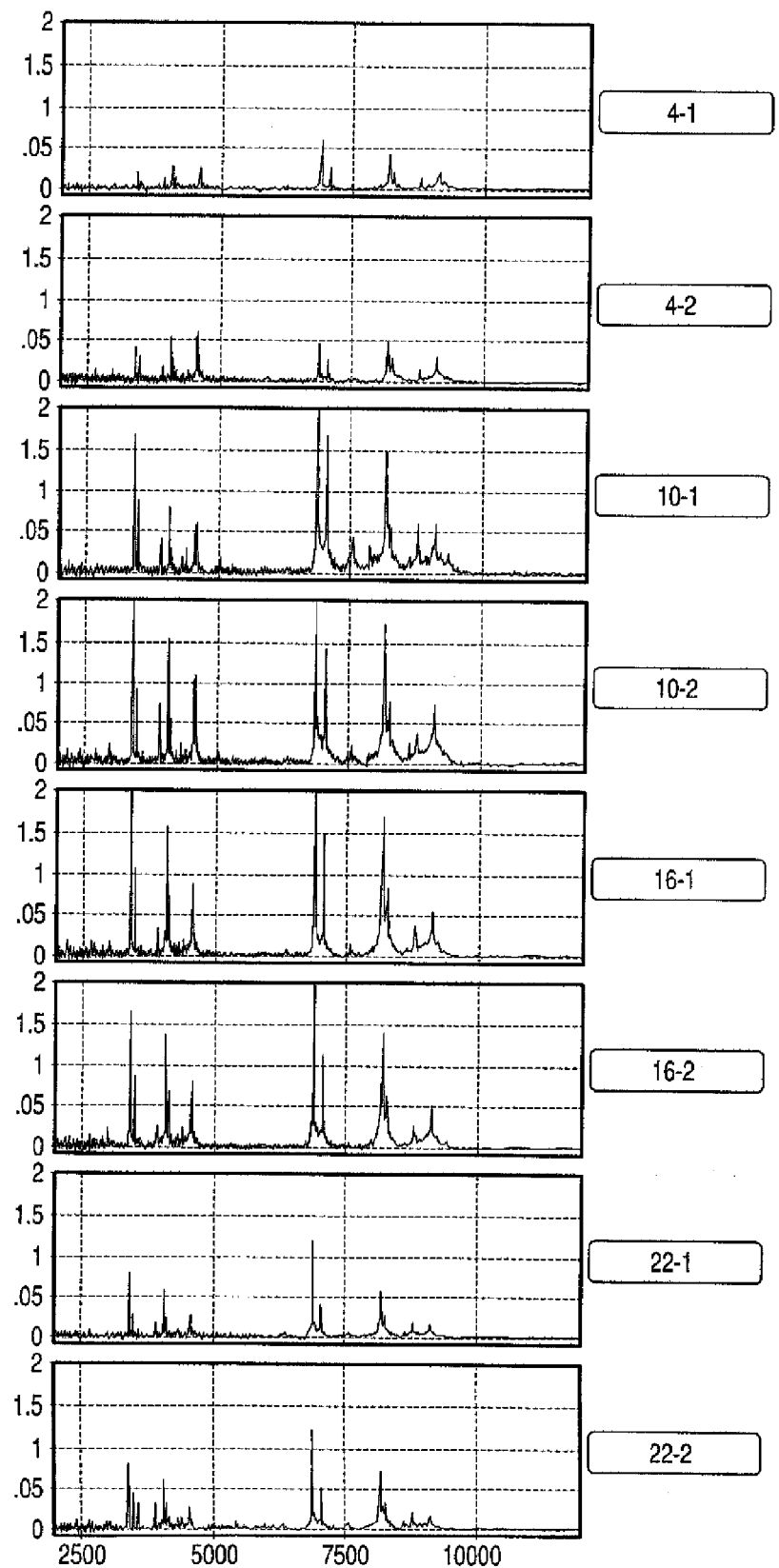
Figure 35B:
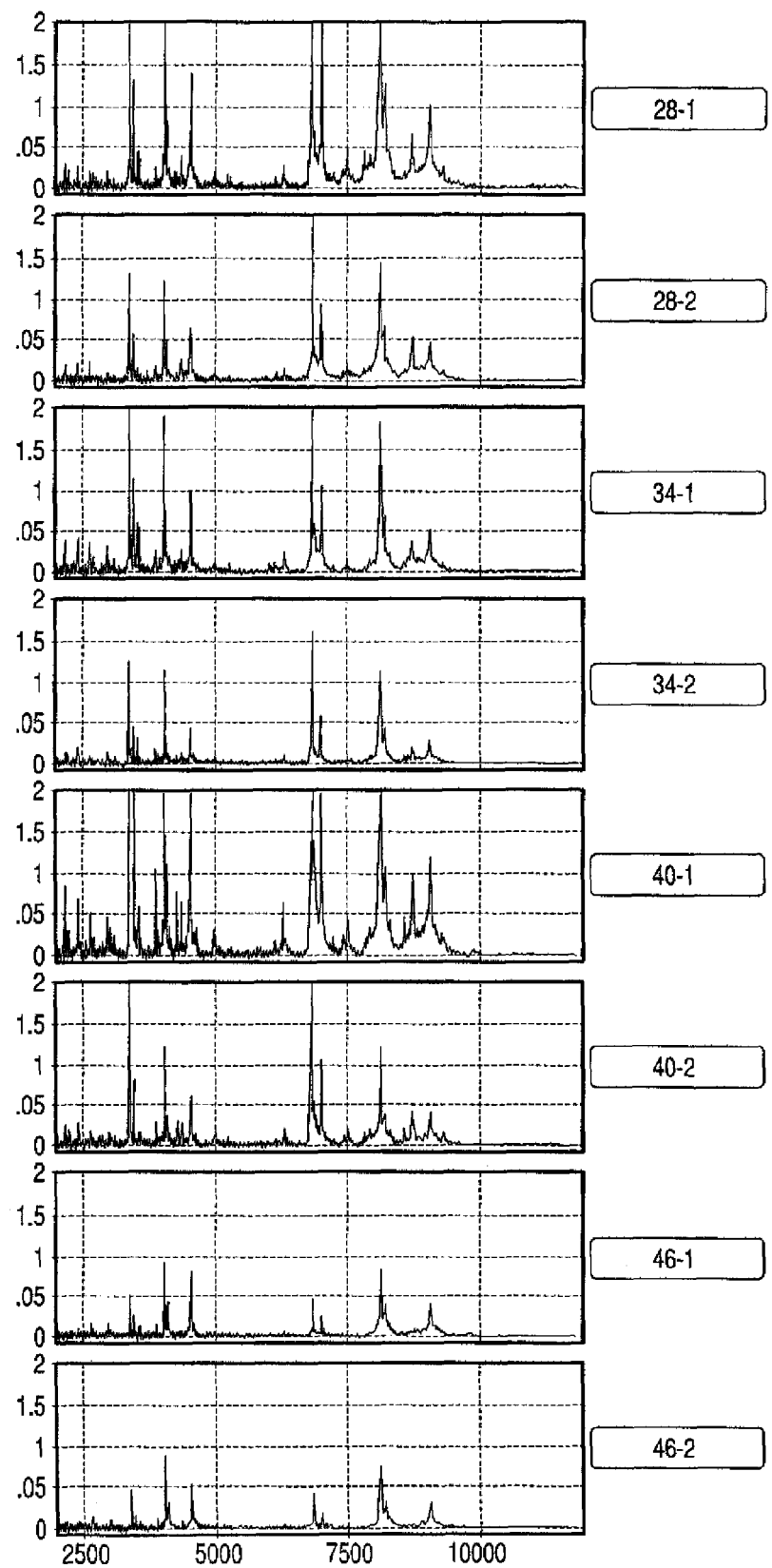
Figure 35C:
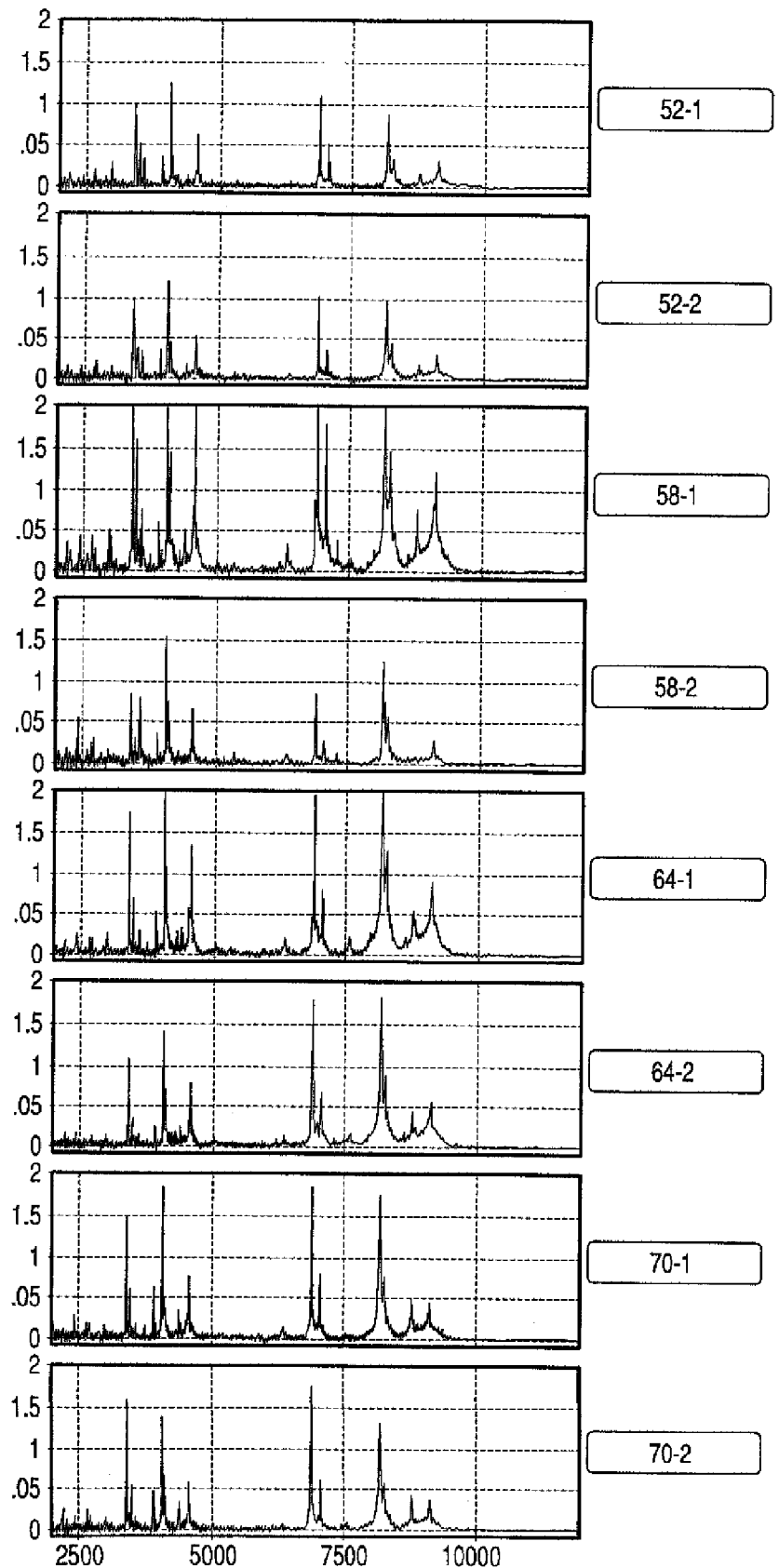
Figure 36A:
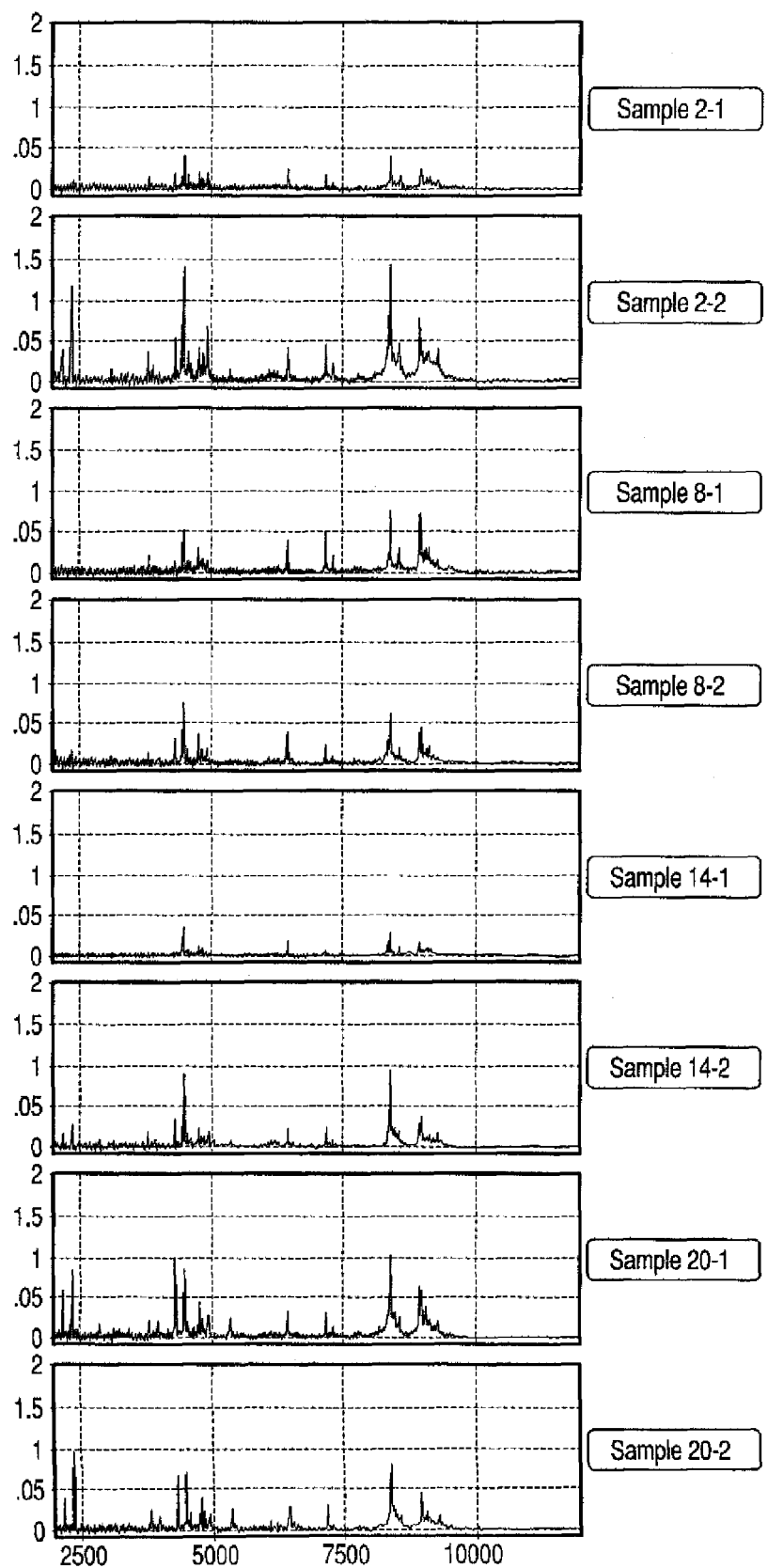
Figure 36B:
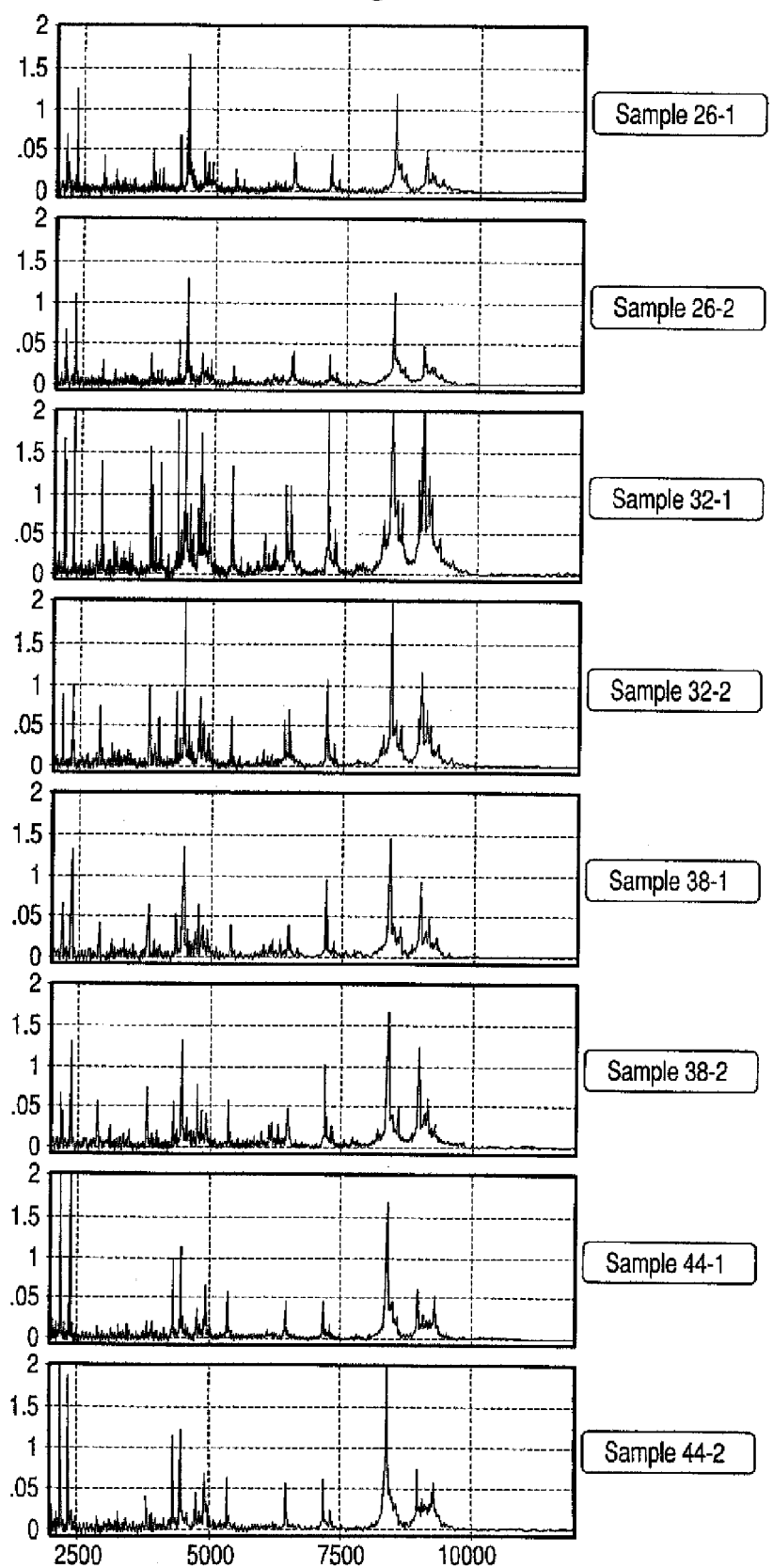
Figure 36C:
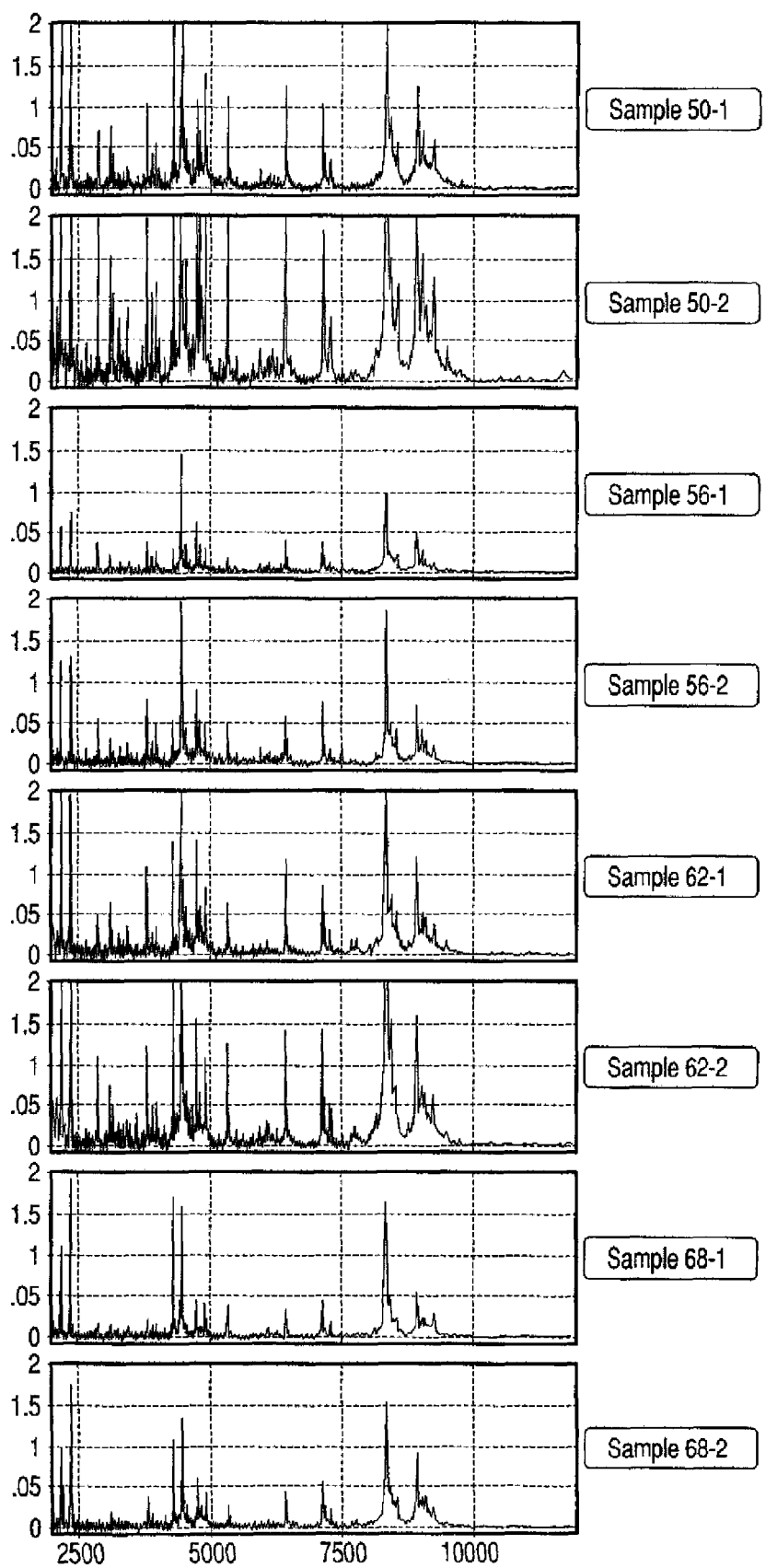
Figure 37A:
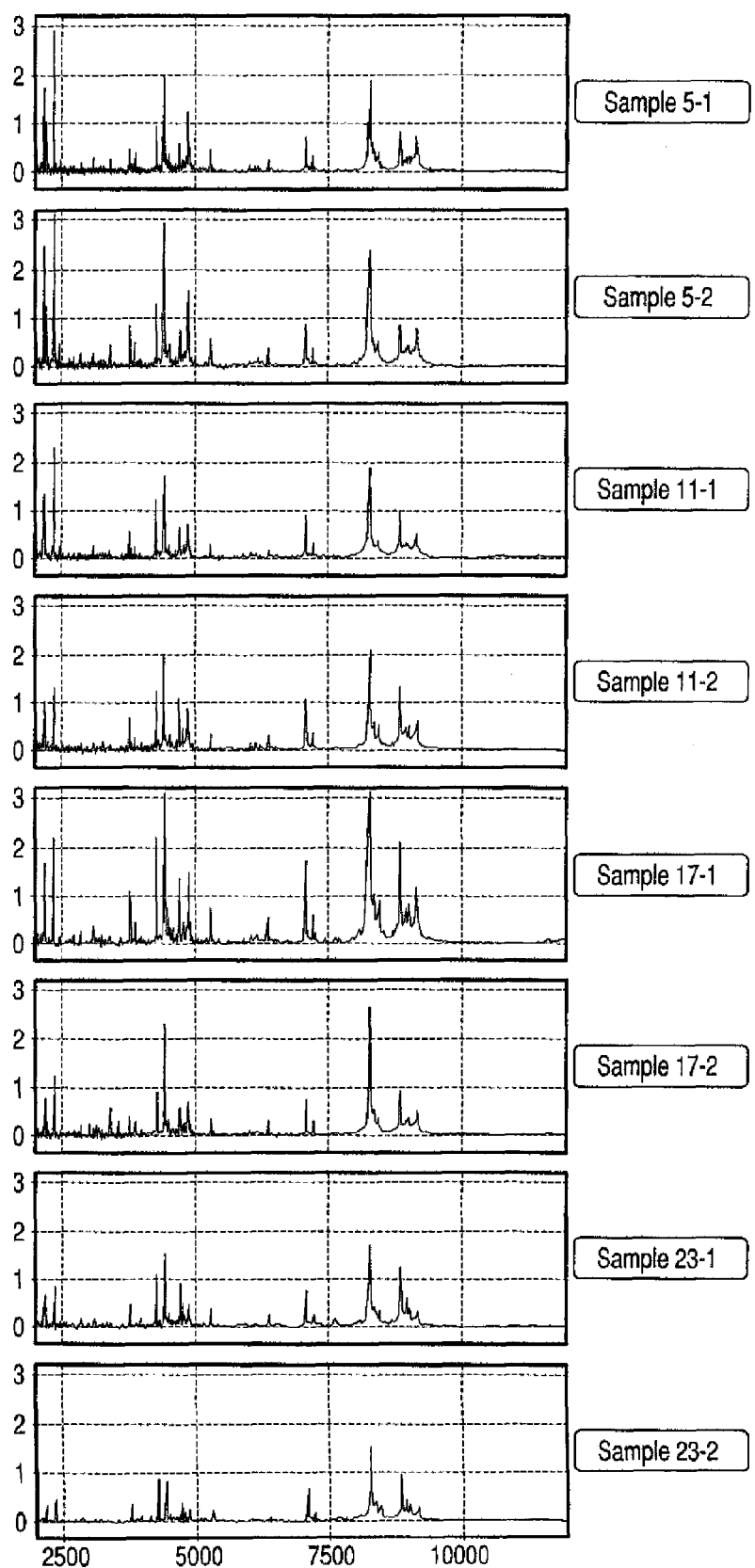
Figure 37B:
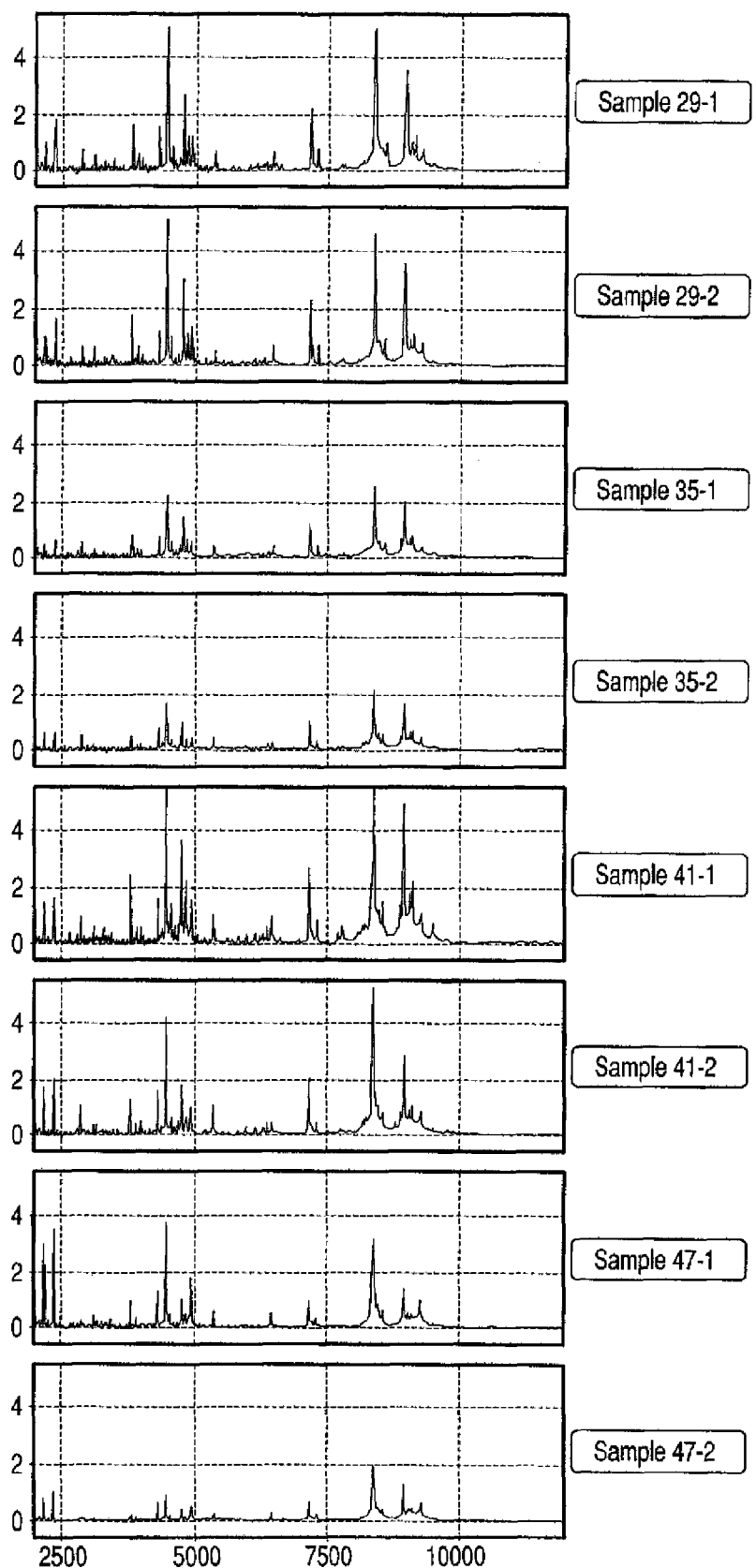
Figure 37C:
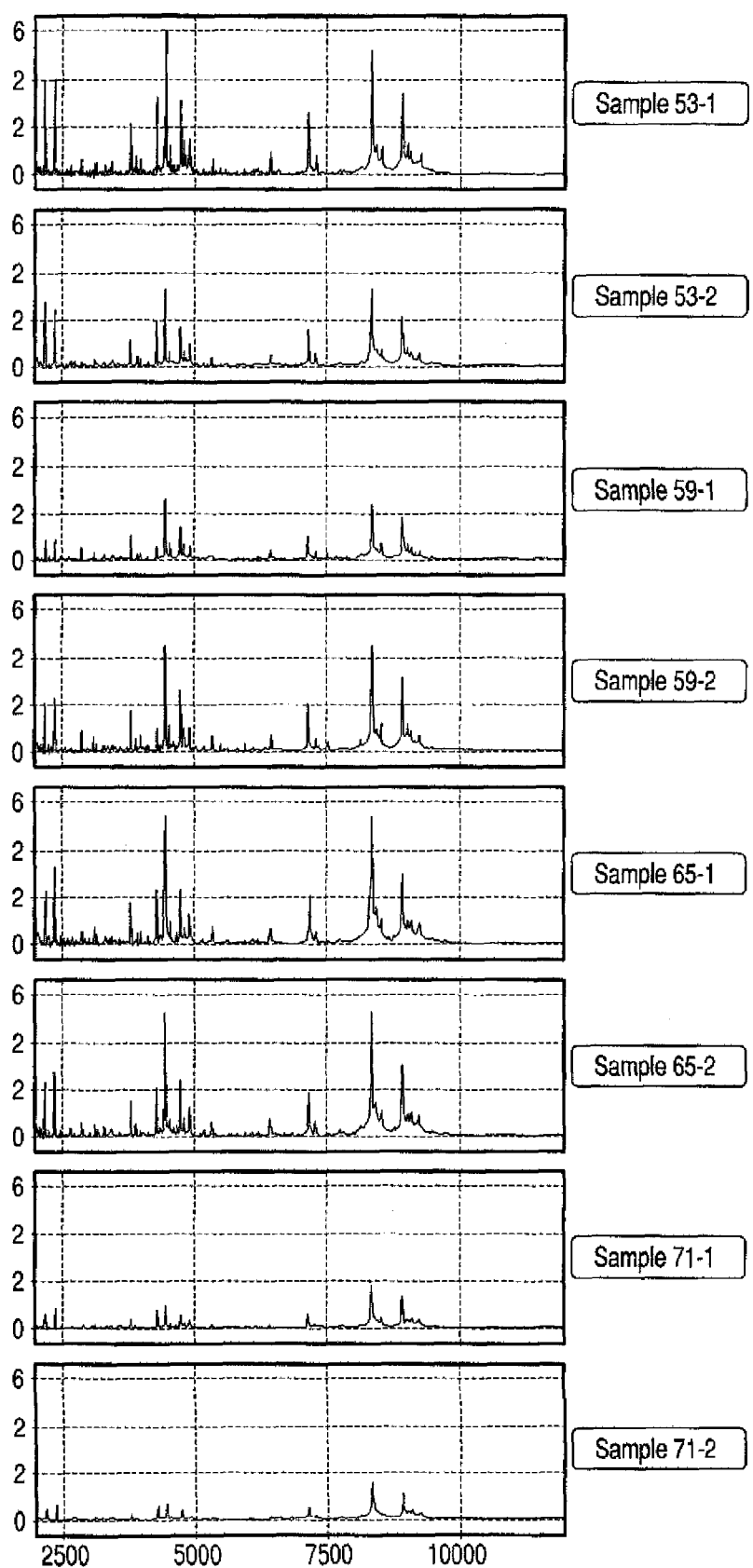
Figure 38A:
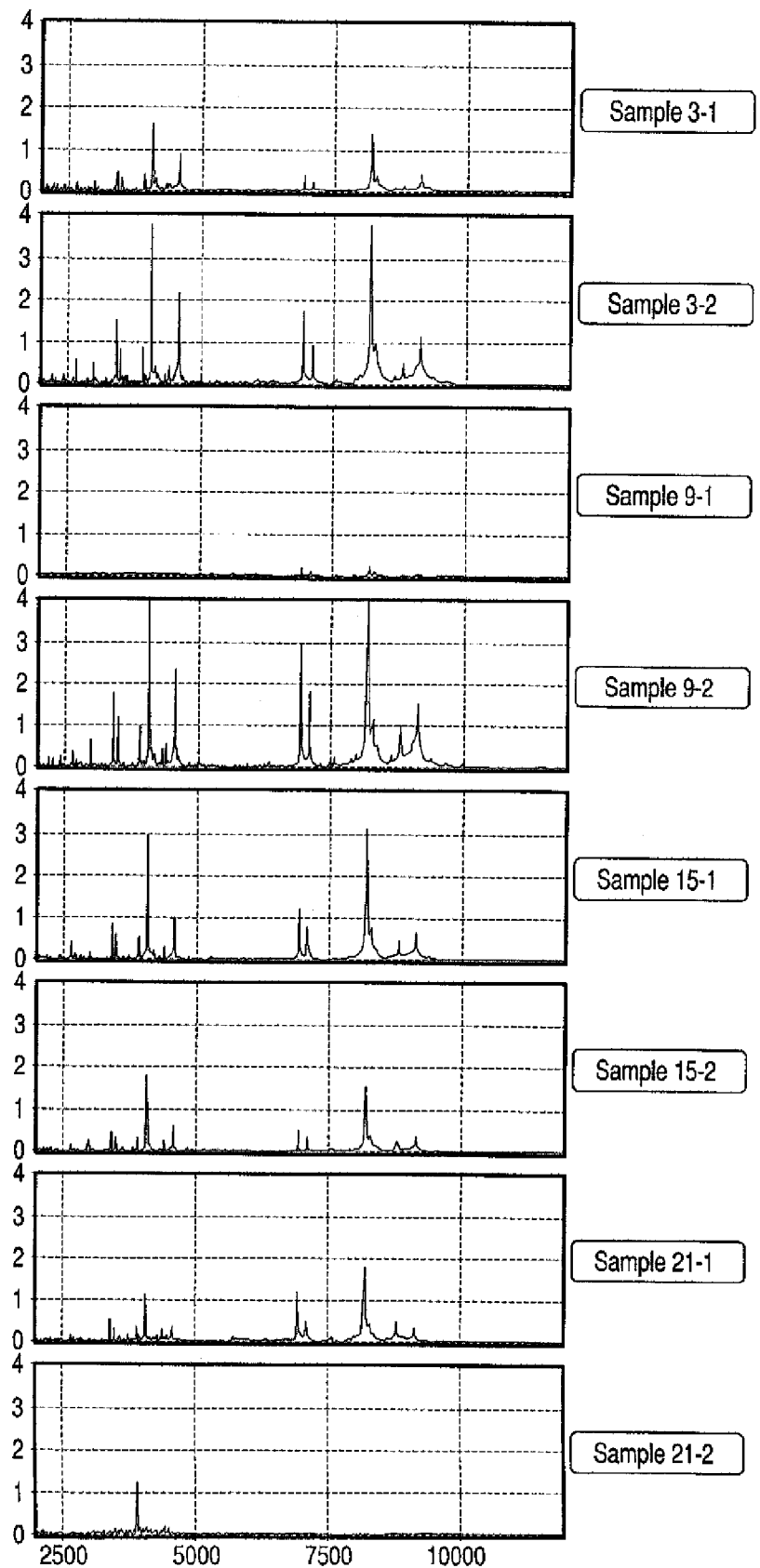
Figure 38B:
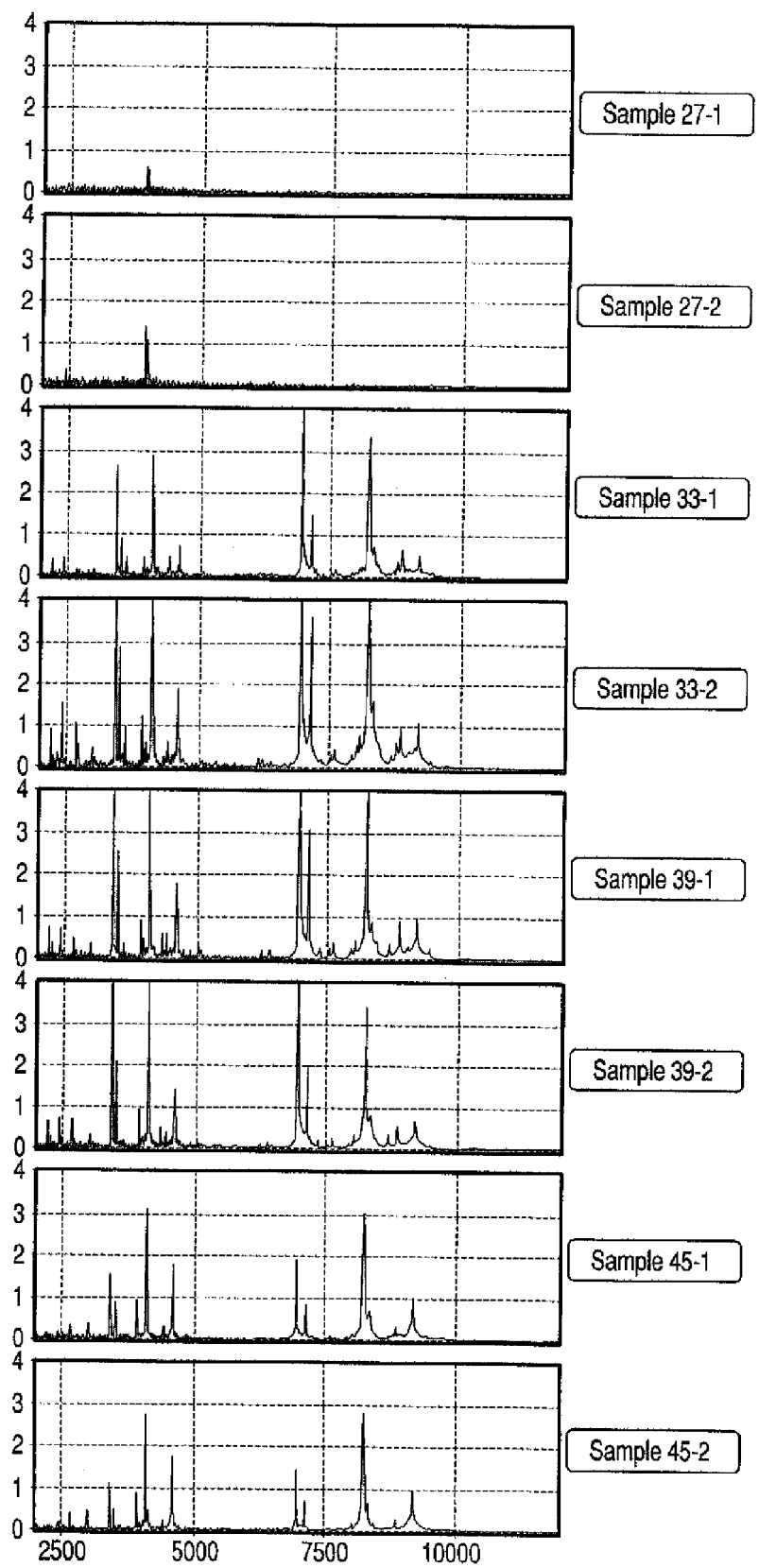
Figure 38C:
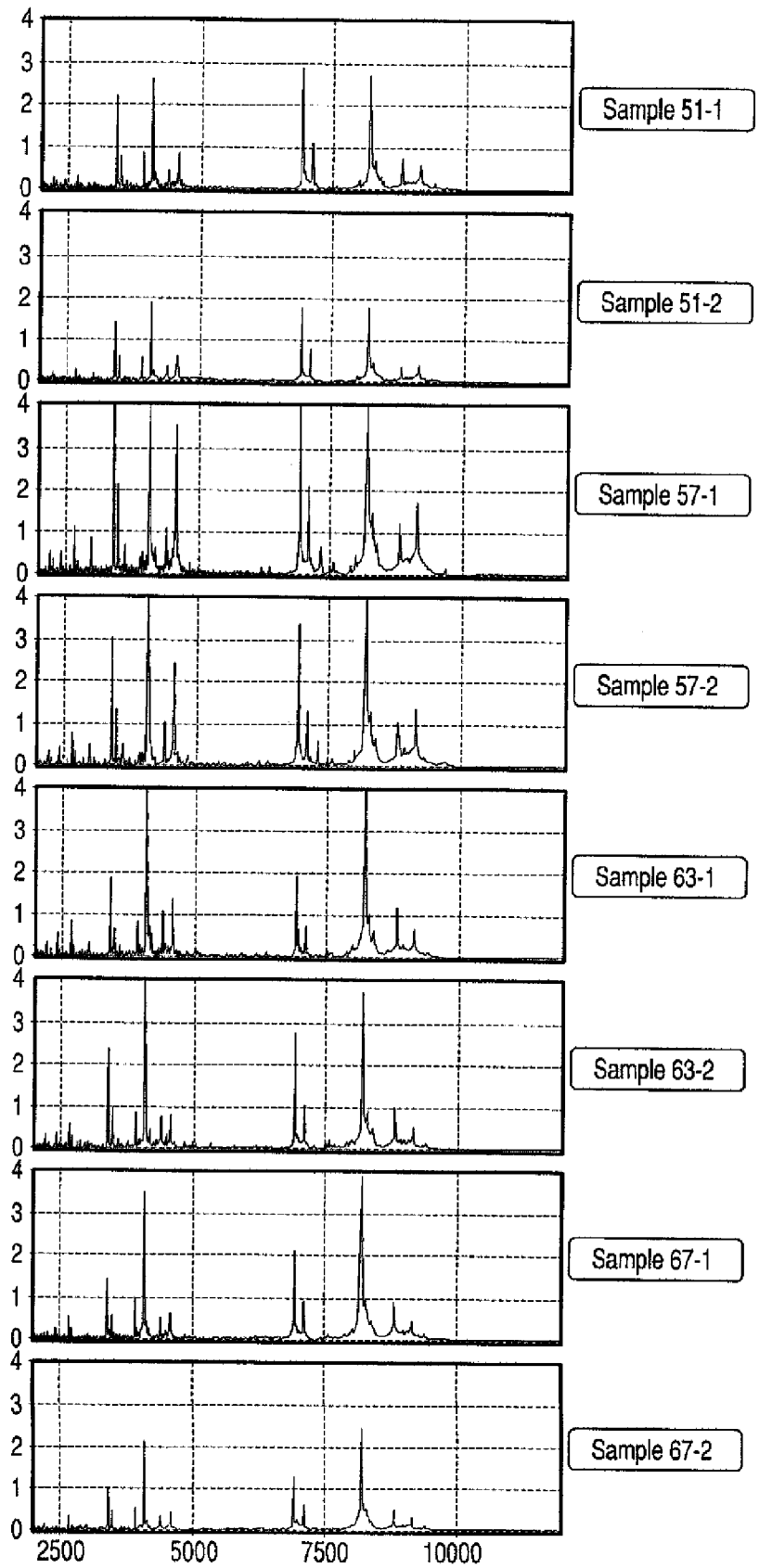
Figure 39A:
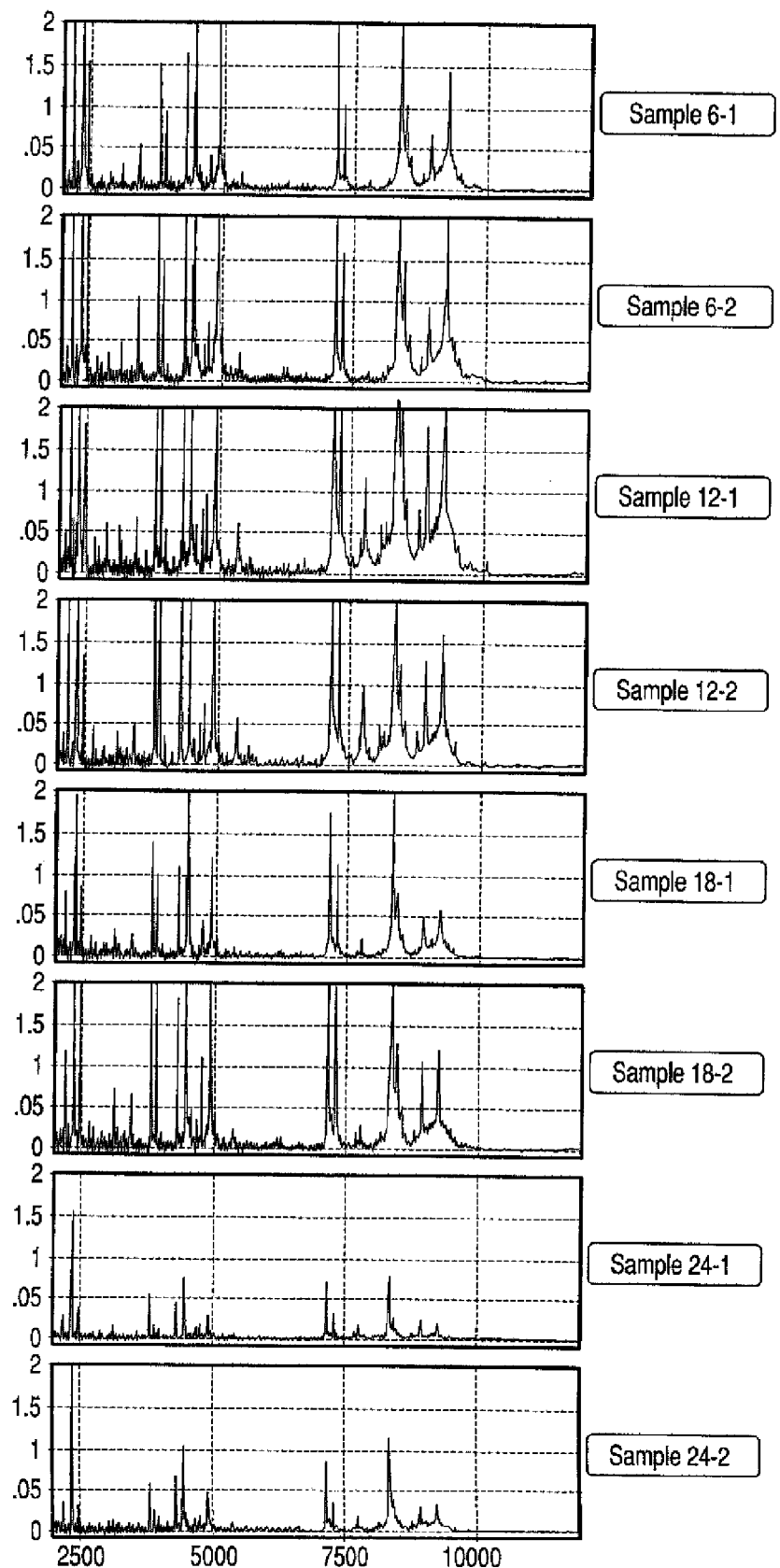
Figure 39B:
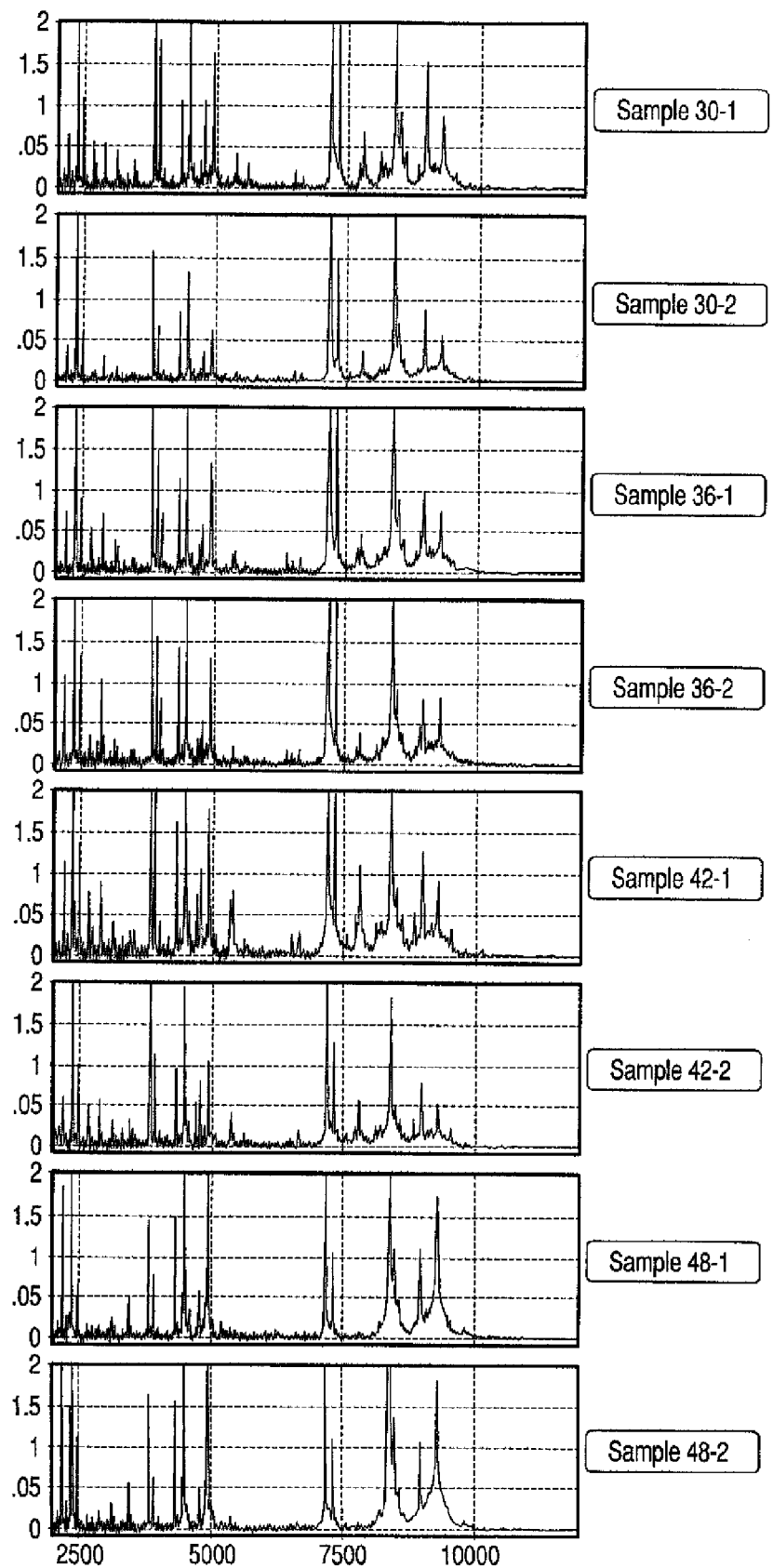
Figure 39C:
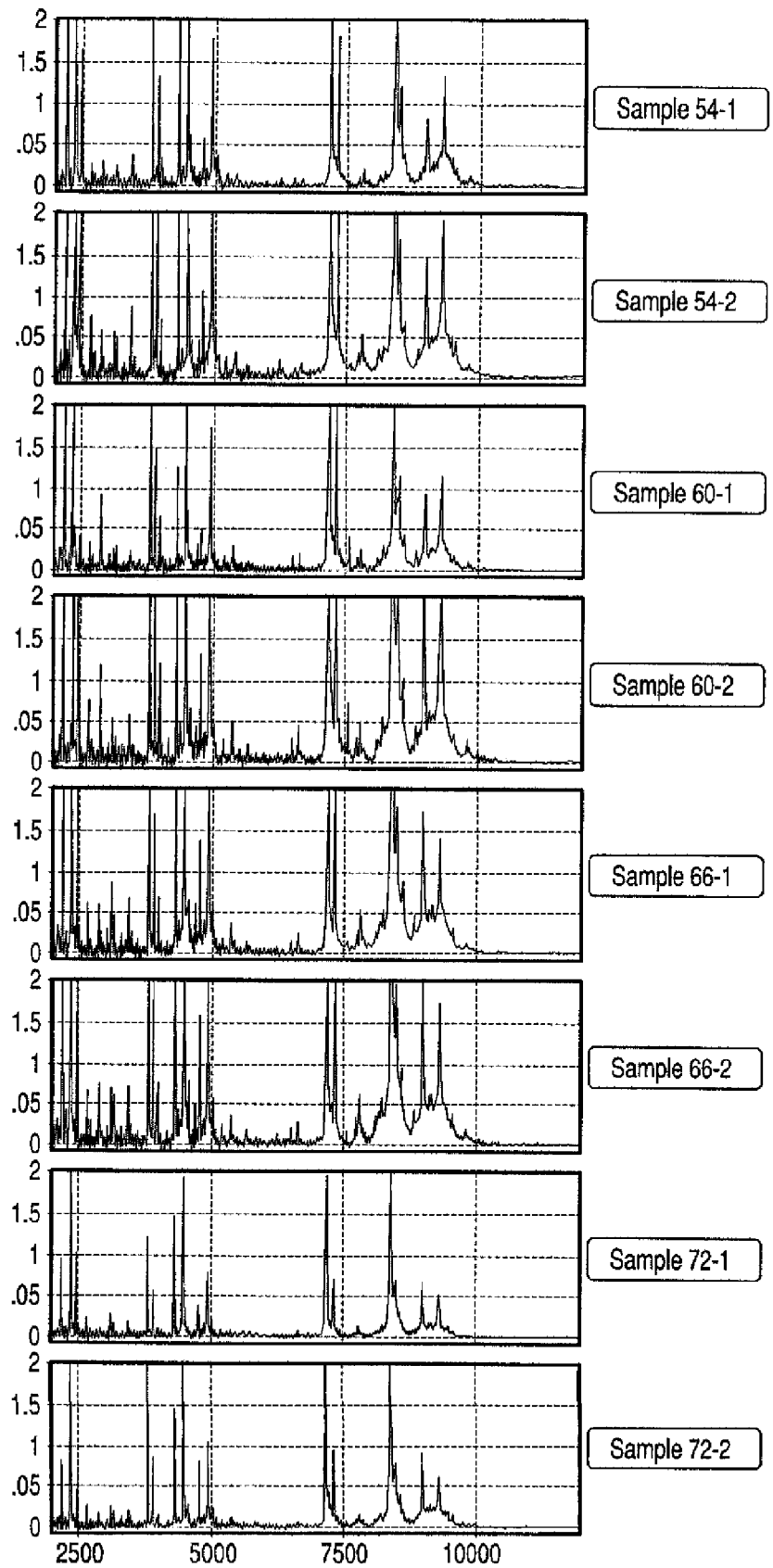

Sample numbers, indicated to the right of the spectra, refer to the sample numbers corresponding to those presented in Table 4. Each of the bead eluates was analyzed in duplicate as indicated in the spectra by sample number x-1 and sample number x-2. Each set of samples applied to an individual 1D gel (see FIGS. 22 through 27) were analyzed in sequence as applied to the gel. Therefore FIGS. 34A, 34B, and 34C represent SELDI spectra from eluate samples applied to gel 1 (FIG. 22); FIGS. 35A, 35B, and 35C represent SELDI spectra from eluate samples applied to gel number 2 (FIG. 23); FIGS. 36A, 36B, and 36C represent SELDI spectra from eluate samples applied to gel number 3 (FIG. 24); FIGS. 37A, 37B, and 37C represent SELDI spectra from eluate samples applied to gel number 4 (FIG. 25); FIGS. 38A, 38B, and 38C represent SELDI spectra from eluate samples applied to gel number 5 (FIG. 26); and FIGS. 39A, 39B, and 39C represent SELDI spectra from eluate samples applied to gel number 6 (FIG. 27).

III Mass Spectrometry LC/MS (OSU CCIC)
In Gel Digestion and Nano LC/MS/MS Protein Identification.

A total of 100 bands from 1D SDS-PAGE were digested and analyzed by nano LC/MS/MS. The detailed results were summarized in Table 5. 707 proteins were identified from the 100 bands examined. Among them, 225 keratin or keratin related proteins were identified. Trypsin was used for the digestion, therefore trypsin and trypsin related proteins are also identified in the samples with a total of 145 trypsin or trypsin related proteins identified. Finally, Lysozyme was used as an internal standard to ensure that the instrument performance and was identified 80 times (Table 6). After removing matches to keratin, lysozyme and trypsin, the total number of significant proteins from the 100 gel bands identified is 257.

As shown in Table 5, most of the proteins were identified multiple times within different lanes/bands. For example, heamoglobin beta-1 chain is identified several times in different lanes/bands. After counting each protein ID only once 154 unique proteins were identified (See Table 6). Among them, 64 were identified as keratin or keratin related proteins, 5 were identified as trypsin or trypsin related proteins and 6 were identified as lysozyme. Therefore, 79 unique SERUM proteins were identified significantly (Table 7).

Gels were digested with sequencing grade trypsin from Promega (Madison Wis.) using the Montage In-Gel Digestion Kit from Millipore (Bedford, Mass.) following manufactures recommended protocols. Briefly, bands were trimmed as close as possible to minimize background polyacrylamide material and cut into 2 mm*2 mm pieces. Gel pieces are then washed in 50% methanol/5% acetic acid for one hour. The wash step is repeated once before gel pieces are dehydrated in acetonitrile. The gel bands were rehydrated and incubated with dithiothertol (DTT) solution (5 mg/ml in 100 mM ammonium bicarbonate) for 30 minute prior to the addition of 15 mg/ml Iodoacetamide in 100 mM ammonium bicarbonate solution. Iodoacetamide was incubated with the gel bands in dark for 30 min before removed. The gel bands were washed again with cycles of acetonitrile and ammonium bicarbonate (100 mM) in 5 min increments. After the gels were dried in speed vac, the protease is driven into the gel pieces by rehydrating them in 50 µL of sequencing grade modified trypsin at 20 µg/mL in 50 mM ammonium bicarbonate for 10 min. 20 µL of 50 mM ammonium bicarbonate was then added to the gel bands and the mixture is incubated at room temperature for overnight. The peptides were extracted from the polyacrylamide gel pieces with 50% acetonitrile and 5% formic acid several times and pooled together. The extracted pools were concentrated in a speed vac to ~25 µL for nano LC/MS/MS analysis.

Capillary-liquid chromatography-nanospray tandem mass spectrometry (Nano-LC/MS/MS) was performed on a Thermo Finnigan LTQ mass spectrometer equipped with a nanospray source operated in positive ion mode. The LC system was an UltiMate™ Plus system (LC-Packings A Dionex Co, Sunnyvale, Calif.) with a Famous autosampler and Switchos column switcher. 5 microliters of each sample was first injected on to the trapping column (LC-Packings A Dionex Co, Sunnyvale, Calif.), and washed with 50 mM acetic acid. The injector port was then switched to injection and the peptides were eluted off the trap onto the column. A 5 cm 75 µm ID ProteoPep II C18 column (New Objective, Inc. Woburn, Mass.) was used for chromatographic separations. Solvent A was water containing 50 mM acetic acid and solvent B was acetonitrile. Peptides were eluted directly off the column into the LTQ system with a flow rate of 300 nl/min. The gradient was started with 2% B and B was kept at 2% for the first 3 minutes.

Then B was increased to 50% from 3-30 minutes and further increased to 80% from 30-45 minutes. B was kept at 80% for another 5 minutes before changed back to 2% in 0.1 minutes. The column was then washed with 98% A for 14.9 minutes before the next injection. The total run time was 65 minutes. The scan sequence of the mass spectrometer was programmed for a full scan and MS/MS scans of the 10 most abundant peptide peaks in the spectrum. Dynamic exclusion was used to exclude multiple MS/MS of the same peptide after detecting and performing MS/MS it 3 times.

Sequence information from the MS/MS data was processed using Mascot Batch to form a peaklist (.mgf file) and by using MASCOT MS/MS search. Data processing was performed following the guidelines in Mole. Cell. Proteomics. Assigned peaks have a minimum of 10 counts (S/N of 3). The mass accuracy of the precursor ions were set to 1.8 Da to accommodate accidental selection of the C13 ion and the fragment mass accuracy was set to 0.5 Da. Considered modifications (variable) were methionine oxidation and carbamidomethyl cysteine.

TABLE 5

| Sample | Protein ID | Score | Swiss-Prot Ascension |
|---|---|---|---|
| A1 | Analysis Of The Stabilization Of Hen Lysozyme With The Helix Dipole And Charged Side Chains | 234 | gi|2781269 |
|  | hemoglobin beta | 182 | gi|229301 |
|  | heamoglobin beta-1 chain [Mus musculus] | 176 | gi|1183932 |
|  | alpha globin [Homo sapiens] | 74 | gi|28549 |
| A2 | keratin 1 [Homo sapiens] | 545 | gi|17318569 |
|  | keratin 10 [Homo sapiens] | 534 | gi|40354192 |
|  | heamoglobin beta-1 chain [Mus musculus] | 499 | gi|1183932 |
|  | haemoglobin beta-2 chain [Mus musculus] | 297 | gi|1183933 |
|  | alpha-globin [Mus musculus] | 279 | gi|49900 |
|  | Analysis Of The Stabilization Of Hen Lysozyme With The Helix Dipole And Charged Side Chains | 235 | gi|2781269 |
|  | PREDICTED: similar to keratin 6 irs isoform 12 [Canis familiaris] | 209 | gi|73996330 |
|  | Keratin 6B [Homo sapiens] | 162 | gi|21961227 |
|  | beta globin chain [Homo sapiens] | 141 | gi|66473265 |

TABLE 5-continued

| Sample | Protein ID | Score | Swiss-Prot Ascension |
|---|---|---|---|
| | platelet factor 4 [*Mus musculus*] | 87 | gi|13560695 |
| | membrane-bound transcriptional regulator LytR [*Bacillus cereus* ATCC 10987] | 56 | gi|42784428 |
| A3 | heamoglobin beta-1 chain [*Mus musculus*] | 509 | gi|1183932 |
| | keratin 1 [*Homo sapiens*] | 500 | gi|17318569 |
| | haemoglobin beta-2 chain [*Mus musculus*] | 348 | gi|1183933 |
| | PREDICTED: similar to keratin 1; Keratin-1; cytokeratin 1; hair alpha protein [*Pan troglodytes*] | 265 | gi|55638031 |
| | keratin 10 [*Oryctolagus cuniculus*] | 258 | gi|87045985 |
| | Analysis Of The Stabilization Of Hen Lysozyme With The Helix Dipole And Charged Side Chains | 197 | gi|2781269 |
| | PREDICTED: similar to keratin 6 irs isoform 12 [*Canis familiaris*] | 172 | gi|73996330 |
| | alpha-globin [*Mus musculus*] | 171 | gi|49900 |
| | Trypsin precursor | 169 | gi|136429 |
| | Hemoglobin beta subunit (Hemoglobin beta chain) (Beta-globin) | 165 | gi|122643 |
| | beta globin chain [*Homo sapiens*] | 157 | gi|66473265 |
| | trypsinogen 10 [*Mus musculus*] | 71 | gi|2358087 |
| | cytokeratin 9 [*Homo sapiens*] | 66 | gi|435476 |
| A4 | Trypsin precursor | 211 | gi|136429 |
| | keratin 1, type II, cytoskeletal - human | 112 | gi|7428712 |
| | alpha globin [*Homo sapiens*] | 98 | gi|28549 |
| | lysozyme | 96 | gi|229157 |
| | cytokeratin 9 [*Homo sapiens*] | 72 | gi|435476 |
| | Hemoglobin beta subunit (Hemoglobin beta chain) (Beta-globin) | 58 | gi|122606 |
| A5 | heamoglobin beta-1 chain [*Mus musculus*] | 515 | gi|1183932 |
| | haemoglobin beta-2 chain [*Mus musculus*] | 351 | gi|1183933 |
| | Trypsin precursor | 265 | gi|136429 |
| | alpha globin [*Homo sapiens*] | 147 | gi|28549 |
| | epidermal cytokeratin 2 [*Homo sapiens*] | 75 | gi|181402 |
| | lysozyme | 65 | gi|229157 |
| A6 | heamoglobin beta-1 chain [*Mus musculus*] | 399 | gi|1183932 |
| | keratin 1 [*Homo sapiens*] | 370 | gi|7331218 |
| | Trypsin precursor | 263 | gi|136429 |
| | alpha-globin [*Mus musculus*] | 213 | gi|49900 |
| | keratin 10 [*Homo sapiens*] | 192 | gi|40354192 |
| | lysozyme | 67 | gi|229157 |
| | trypsinogen 10 [*Mus musculus*] | 62 | gi|2358087 |
| A7 | transferrin [*Mus musculus*] | 304 | gi|17046471 |
| | keratin 1 [*Homo sapiens*] | 244 | gi|17318569 |
| | inter alpha-trypsin inhibitor, heavy chain 4 [*Mus musculus*] | 201 | gi|9055252 |
| | Trypsin precursor | 162 | gi|136429 |
| | gelsolin, cytosolic - mouse | 112 | gi|90508 |
| | histidine-rich glycoprotein [*Mus musculus*] | 111 | gi|11066003 |
| | thioredoxin [*Escherichia coli*] | 98 | gi|148071 |
| | apolipoprotein A-I precursor - mouse | 61 | gi|109571 |
| | alpha-fetoprotein | 53 | gi|191765 |
| A8 | cytokeratin 9 [*Homo sapiens*] | 1282 | gi|435476 |
| | keratin 1 [*Homo sapiens*] | 1235 | gi|7331218 |
| | Chain E, Leech-Derived Tryptase InhibitorTRYPSIN COMPLEX | 294 | gi|3318722 |
| | PREDICTED: similar to keratin 6 irs isoform 12 [*Canis familiaris*] | 288 | gi|73996330 |
| | keratin 10 [*Homo sapiens*] | 219 | gi|40354192 |
| | epidermal keratin subunit II | 130 | gi|293686 |
| | apolipoprotein A-I precursor - mouse | 112 | gi|109571 |
| | lysozyme | 97 | gi|229157 |
| | trypsinogen 7 [*Mus musculus*] | 61 | gi|2358072 |
| | Short-chain dehydrogenase/reductase SDR [*Burkholderia* sp. 383] | 59 | gi|77965219 |
| A9 | heamoglobin beta-1 chain [*Mus musculus*] | 469 | gi|1183932 |
| | haemoglobin beta-2 chain [*Mus musculus*] | 448 | gi|1183933 |
| | keratin 1 [*Homo sapiens*] | 293 | gi|17318569 |
| | alpha-globin [*Mus musculus*] | 256 | gi|49900 |
| | Trypsin precursor | 208 | gi|136429 |
| | PREDICTED: similar to keratin 6 irs isoform 12 [*Canis familiaris*] | 168 | gi|73996330 |
| | Analysis Of The Stabilization Of Hen Lysozyme With The Helix Dipole And Charged Side Chains | 103 | gi|2781269 |
| | keratin 10 [*Homo sapiens*] | 87 | gi|40354192 |
| | membrane-bound transcriptional regulator LytR [*Bacillus cereus* ATCC 10987] | 59 | gi|42784428 |

TABLE 5-continued

| Sample | Protein ID | Score | Swiss-Prot Ascension |
|---|---|---|---|
| A10 | keratin 1 [Homo sapiens] | 223 | gi|17318569 |
| | Analysis Of The Stabilization Of Hen Lysozyme With The Helix Dipole And Charged Side Chains | 218 | gi|2781269 |
| | Trypsin precursor | 115 | gi|136429 |
| | Lysozyme C (1,4-beta-N-acetylmuramidase C) | 94 | gi|47117006 |
| A11 | type I keratin 16; K16 [Homo sapiens] | 1301 | gi|1195531 |
| | Keratin 14 [Homo sapiens] | 1134 | gi|17512236 |
| | keratin type II | 492 | gi|386849 |
| | Keratin 6B [Homo sapiens] | 435 | gi|21961227 |
| | keratin 1 [Homo sapiens] | 367 | gi|7331218 |
| | keratin 5 [Homo sapiens] | 349 | gi|4557890 |
| | PREDICTED: similar to keratin 6 irs isoform 12 [Canis familiaris] | 257 | gi|73996330 |
| | PREDICTED: similar to keratin 15 [Bos taurus] | 209 | gi|61813798 |
| | Trypsin precursor | 179 | gi|136429 |
| | Analysis Of The Stabilization Of Hen Lysozyme With The Helix Dipole And Charged Side Chains | 149 | gi|2781269 |
| | PREDICTED: similar to keratin 8, type II cytoskeletal - human [Pan troglodytes] | 90 | gi|55638407 |
| | cytokeratin 9 [Homo sapiens] | 88 | gi|435476 |
| | trypsinogen 10 [Mus musculus] | 66 | gi|2358087 |
| A12 | Analysis Of The Stabilization Of Hen Lysozyme With The Helix Dipole And Charged Side Chains | 204 | gi|2781269 |
| | Trypsin precursor | 178 | gi|136429 |
| | epidermal cytokeratin 2 [Homo sapiens] | 72 | gi|181402 |
| | trypsinogen 10 [Mus musculus] | 68 | gi|2358087 |
| B1 | Trypsin precursor | 180 | gi|136429 |
| | apolipoprotein C-III [Mus musculus] | 129 | gi|15421856 |
| | Analysis Of The Stabilization Of Hen Lysozyme With The Helix Dipole And Charged Side Chains | 111 | gi|2781269 |
| | complement component C3 precursor | 97 | gi|192392 |
| | trypsinogen 10 [Mus musculus] | 54 | gi|2358087 |
| B2 | keratin 1 [Homo sapiens] | 195 | gi|17318569 |
| | Trypsin precursor | 176 | gi|136429 |
| | apolipoprotein C-III [Mus musculus] | 124 | gi|15421856 |
| | Analysis Of The Stabilization Of Hen Lysozyme With The Helix Dipole And Charged Side Chains | 99 | gi|2781269 |
| | complement component C3 precursor | 72 | gi|192392 |
| | trypsinogen 7 [Mus musculus] | 67 | gi|2358072 |
| | trypsinogen 10 [Mus musculus] | 62 | gi|2358087 |
| B3 | Trypsin precursor | 275 | gi|136429 |
| | apolipoprotein C-III [Mus musculus] | 129 | gi|15421856 |
| | Analysis Of The Stabilization Of Hen Lysozyme With The Helix Dipole And Charged Side Chains | 123 | gi|2781269 |
| | complement component C3 precursor | 76 | gi|192392 |
| | trypsinogen 10 [Mus musculus] | 68 | gi|2358087 |
| B4 | Trypsin precursor | 265 | gi|136429 |
| | apolipoprotein C-III [Mus musculus] | 125 | gi|15421856 |
| | lysozyme | 74 | gi|229157 |
| | complement component C3 precursor | 71 | gi|192392 |
| | trypsinogen 10 [Mus musculus] | 68 | gi|2358087 |
| B5 | Trypsin precursor | 212 | gi|136429 |
| | apolipoprotein C-III [Mus musculus] | 120 | gi|15421856 |
| | complement component C3 precursor | 75 | gi|192392 |
| | lysozyme | 72 | gi|229157 |
| | trypsinogen 10 [Mus musculus] | 62 | gi|2358087 |
| B6 | Trypsin precursor | 176 | gi|136429 |
| | keratin 1, type II, cytoskeletal - human | 142 | gi|7428712 |
| | apolipoprotein C-III [Mus musculus] | 122 | gi|15421856 |
| | Analysis Of The Stabilization Of Hen Lysozyme With The Helix Dipole And Charged Side Chains | 95 | gi|2781269 |
| | complement component C3 precursor | 88 | gi|192392 |
| | trypsinogen 10 [Mus musculus] | 66 | gi|2358087 |
| B7 | Albumin 1 [Mus musculus] | 1536 | gi|29612571 |
| | keratin 1 [Homo sapiens] | 1518 | gi|17318569 |
| | cytokeratin 9 [Homo sapiens] | 649 | gi|435476 |
| | Trypsin precursor | 272 | gi|136429 |
| | PREDICTED: similar to keratin 6 irs isoform 12 [Canis familiaris] | 259 | gi|73996330 |
| | Complement C3 precursor (HSE-MSF) [Contains: Complement C3 beta chain; Complement C3 alpha chain; C | 99 | gi|1352102 |
| | trypsinogen 10 [Mus musculus] | 66 | gi|2358087 |
| | hypothetical protein SAV6338 [Streptomyces avermitilis MA-4680] | 62 | gi|29832880 |

TABLE 5-continued

| Sample | Protein ID | Score | Swiss-Prot Ascension |
|---|---|---|---|
| B8 | keratin 1 [Homo sapiens] | 913 | gi|17318569 |
| | keratin 10 [Homo sapiens] | 592 | gi|40354192 |
| | cytokeratin 9 [Homo sapiens] | 390 | gi|435476 |
| | heamoglobin, beta-1 chain [Mus musculus] | 350 | gi|1183932 |
| | hemoglobin, beta adult major chain [Mus musculus] | 349 | gi|31982300 |
| | PREDICTED: similar to keratin 6 irs isoform 12 [Canis familiaris] | 271 | gi|73996330 |
| | Trypsin precursor | 263 | gi|136429 |
| | PREDICTED: similar to Keratin, type II cytoskeletal 5 (Cytokeratin 5) (K5) (CK 5) (58 kDa cytokerat | 262 | gi|73996312 |
| | Analysis Of The Stabilization Of Hen Lysozyme With The Helix Dipole And Charged Side Chains | 260 | gi|2781269 |
| | type I keratin 16; K16 [Homo sapiens] | 252 | gi|1195531 |
| | PREDICTED: similar to keratin 1 isoform 2 [Bos taurus] | 243 | gi|76617876 |
| | haemoglobin beta-2 chain [Mus musculus] | 217 | gi|1183933 |
| | alpha-globin [Mus musculus] | 152 | gi|49900 |
| | profilin 1 [Mus musculus] | 111 | gi|56206029 |
| | PREDICTED: similar to trypsinogen 7 isoform 4 [Canis familiaris] | 102 | gi|73978531 |
| | cystatin C precursor [Mus musculus] | 98 | gi|11762010 |
| | Transthyretin [Mus musculus] | 95 | gi|56541070 |
| | type I keratin 10 [Protopterus aethiopicus] | 85 | gi|57335414 |
| | parvalbumin [Mus musculus] | 77 | gi|509139 |
| | lysozyme | 73 | gi|841217 |
| | Flp pilus assembly protein CpaB family [Burkholderia thailandensis E264] | 57 | gi|83719123 |
| | Hemoglobin beta subunit (Hemoglobin beta chain) (Beta-globin) | 55 | gi|122643 |
| B9 | keratin 10 [Homo sapiens] | 1068 | gi|40354192 |
| | keratin 1 [Homo sapiens] | 926 | gi|7331218 |
| | epidermal cytokeratin 2 [Homo sapiens] | 700 | gi|181402 |
| | cytokeratin 9 [Homo sapiens] | 551 | gi|435476 |
| | PREDICTED: similar to keratin 6 irs [Pan troglodytes] | 435 | gi|55638029 |
| | PREDICTED: similar to keratin 6 irs isoform 12 [Canis familiaris] | 319 | gi|73996330 |
| | Trypsin precursor | 237 | gi|136429 |
| | Analysis Of The Stabilization Of Hen Lysozyme With The Helix Dipole And Charged Side Chains | 230 | gi|2781269 |
| | apolipoprotein C-III [Mus musculus] | 129 | gi|15421856 |
| | complement component C3 precursor | 89 | gi|192392 |
| | type I keratin 10 [Protopterus aethiopicus] | 83 | gi|57335414 |
| | keratin 19 [Homo sapiens] | 71 | gi|7594734 |
| | trypsinogen 10 [Mus musculus] | 66 | gi|2358087 |
| | adenylate kinase [Clonorchis sinensis] | 59 | gi|22652628 |
| | nonsymbiotic hemoglobin [Alnus firma] | 58 | gi|84993584 |
| B10 | keratin 1 [Homo sapiens] | 1448 | gi|17318569 |
| | cytokeratin 9 [Homo sapiens] | 1294 | gi|435476 |
| | Keratin 6A [Homo sapiens] | 653 | gi|14250682 |
| | keratin 10 [Homo sapiens] | 568 | gi|40354192 |
| | PREDICTED: similar to Keratin, type I cytoskeletal 14 (Cytokeratin 14) (K14) (CK 14) isoform 3 [Bos | 445 | gi|76649703 |
| | PREDICTED: similar to keratin 6 irs [Pan troglodytes] | 410 | gi|55638029 |
| | PREDICTED: similar to keratin 6 irs isoform 12 [Canis familiaris] | 399 | gi|73996330 |
| | type I keratin 16; K16 [Homo sapiens] | 377 | gi|1195531 |
| | epidermal keratin subunit II | 347 | gi|293686 |
| | keratin complex 1, acidic, gene 14 [Mus musculus] | 311 | gi|21489935 |
| | Trypsin precursor | 118 | gi|136429 |
| | PREDICTED: similar to trypsinogen 7 isoform 4 [Canis familiaris] | 108 | gi|73978531 |
| | Analysis Of The Stabilization Of Hen Lysozyme With The Helix Dipole And Charged Side Chains | 94 | gi|2781269 |
| | type II alpha-keratin IIB [Gallus gallus] | 89 | gi|46399075 |
| | PREDICTED: similar to Keratin, type II cytoskeletal 8 (Cytokeratin 8) (Cytokeratin endo A) [Rattus | 87 | gi|62657929 |
| | trypsinogen 10 [Mus musculus] | 66 | gi|2358087 |
| | Short-chain dehydrogenase/reductase SDR [Burkholderia sp. 383] | 66 | gi|77965219 |
| B11 | Complement C3 precursor (HSE-MSF) [Contains: Complement C3 beta chain; Complement C3 alpha chain; C | 358 | gi|1352102 |
| | Chain E, Leech-Derived Tryptase Inhibitor TRYPSIN COMPLEX | 291 | gi|3318722 |
| | Analysis Of The Stabilization Of Hen Lysozyme With The Helix Dipole And Charged Side Chains | 216 | gi|2781269 |

TABLE 5-continued

| Sample | Protein ID | Score | Swiss-Prot Ascension |
|---|---|---|---|
| | keratin 1, type II, cytoskeletal - human | 175 | gi|7428712 |
| | keratin 15 [*Homo sapiens*] | 166 | gi|30583361 |
| | thioredoxin [*Escherichia coli*] | 69 | gi|148071 |
| | trypsinogen 10 [*Mus musculus*] | 66 | gi|2358087 |
| B12 | keratin 10 [*Homo sapiens*] | 872 | gi|40354192 |
| | keratin 1 [*Homo sapiens*] | 827 | gi|17318569 |
| | Keratin 6A [*Homo sapiens*] | 632 | gi|14250682 |
| | Keratin 17 [*Homo sapiens*] | 516 | gi|48735384 |
| | cytokeratin 9 [*Homo sapiens*] | 465 | gi|435476 |
| | PREDICTED: similar to Keratin, type I cytoskeletal 14 (Cytokeratin 14) (K14) (CK 14) isoform 3 [*Bos* | 444 | gi|76649703 |
| | keratin | 437 | gi|386848 |
| | keratin K5 | 390 | gi|386850 |
| | PREDICTED: similar to keratin 6 irs isoform 12 [*Canis familiaris*] | 310 | gi|73996330 |
| | keratin type 16 | 283 | gi|186685 |
| | Trypsin precursor | 275 | gi|136429 |
| | calmodulin-like 5 [*Homo sapiens*] | 195 | gi|55859601 |
| | PREDICTED: similar to keratin 17 [*Pan troglodytes*] | 184 | gi|55644941 |
| | type I keratin 10 [*Protopterus aethiopicus*] | 84 | gi|57335414 |
| | PREDICTED: similar to Keratin, type II cytoskeletal 8 (Cytokeratin-8) (CK-8) (Keraton-8) (K8) [*Homo* | 80 | gi|88988823 |
| | glyceraldehyde-3-phosphate dehydrogenase [*Homo sapiens*] | 62 | gi|31645 |
| | hypothetical protein FG03380.1 [*Gibberella zeae* PH-1] | 57 | gi|46115076 |
| C1 | Chain E, Leech-Derived Tryptase InhibitorTRYPSIN COMPLEX | 193 | gi|3318722 |
| | platelet basic protein [*Mus musculus*] | 156 | gi|13560694 |
| | PREDICTED: similar to keratin 6 irs isoform 12 [*Canis familiaris*] | 110 | gi|73996330 |
| | Apolipoprotein A-II [*Mus musculus*] | 99 | gi|21618837 |
| | ubiquitin | 85 | gi|223061 |
| C2 | keratin 10 [*Oryctolagus cuniculus*] | 288 | gi|87045985 |
| | keratin 1 [*Homo sapiens*] | 224 | gi|17318569 |
| | Trypsin precursor | 179 | gi|136429 |
| | platelet basic protein [*Mus musculus*] | 166 | gi|13560694 |
| | Apolipoprotein A-II [*Mus musculus*] | 162 | gi|21618837 |
| | lysozyme | 99 | gi|229157 |
| | cytokeratin 9 [*Homo sapiens*] | 75 | gi|435476 |
| | ubiquitin | 65 | gi|223061 |
| | Apolipoprotein C-I (Apo-CI) (ApoC-I) | 63 | gi|114017 |
| C3 | Trypsin precursor | 241 | gi|136429 |
| | platelet basic protein [*Mus musculus*] | 160 | gi|13560694 |
| | Apolipoprotein A-II [*Mus musculus*] | 105 | gi|21618837 |
| | lysozyme | 67 | gi|229157 |
| | ubiquitin | 64 | gi|223061 |
| | membrane-bound transcriptional regulator LytR [*Bacillus cereus* ATCC 10987] | 56 | gi|42784428 |
| C4 | Trypsin precursor | 172 | gi|136429 |
| | platelet basic protein [*Mus musculus*] | 126 | gi|13560694 |
| | trypsinogen 10 [*Mus musculus*] | 62 | gi|2358087 |
| | Apolipoprotein A-II [*Mus musculus*] | 61 | gi|21618837 |
| | Analysis Of The Stabilization Of Hen Lysozyme With The Helix Dipole And Charged Side Chains | 57 | gi|2781269 |
| C5 | Trypsin precursor | 167 | gi|136429 |
| | platelet basic protein [*Mus musculus*] | 127 | gi|13560694 |
| | keratin 1 [*Homo sapiens*] | 125 | gi|7331218 |
| | trypsinogen 10 [*Mus musculus*] | 58 | gi|2358087 |
| | Apolipoprotein A-II [*Mus musculus*] | 56 | gi|21618837 |
| C6 | Analysis Of The Stabilization Of Hen Lysozyme With The Helix Dipole And Charged Side Chains | 251 | gi|2781269 |
| | Trypsin precursor | 225 | gi|136429 |
| | platelet basic protein [*Mus musculus*] | 160 | gi|13560694 |
| | Apolipoprotein A-II [*Mus musculus*] | 92 | gi|21618837 |
| | trypsin (EC 3.4.21.4) precursor - bovine | 88 | gi|67549 |
| | membrane-bound transcriptional regulator LytR [*Bacillus cereus* ATCC 10987] | 55 | gi|42784428 |
| C7 | keratin 1 [*Homo sapiens*] | 1151 | gi|17318569 |
| | cytokeratin 9 [*Homo sapiens*] | 1009 | gi|435476 |
| | keratin 6C [*Homo sapiens*] | 539 | gi|17505189 |
| | keratin K5 | 375 | gi|386850 |
| | PREDICTED: similar to keratin 6 irs isoform 12 [*Canis familiaris*] | 348 | gi|73996330 |
| | type II keratin Kb1 [*Rattus norvegicus*] | 319 | gi|57012354 |
| | Trypsin precursor | 224 | gi|136429 |
| | Analysis Of The Stabilization Of Hen Lysozyme With The Helix Dipole And Charged Side Chains | 215 | gi|2781269 |

TABLE 5-continued

| Sample | Protein ID | Score | Swiss-Prot Ascension |
|---|---|---|---|
| | keratin 10 [Homo sapiens] | 215 | gi|40354192 |
| | inter alpha-trypsin inhibitor, heavy chain 4 [Mus musculus] | 162 | gi|9055252 |
| | alpha-fetoprotein | 61 | gi|191765 |
| | thioredoxin [Escherichia coli] | 61 | gi|148071 |
| C8 | heamoglobin beta-1 chain [Mus musculus] | 553 | gi|1183932 |
| | haemoglobin beta-2 chain [Mus musculus] | 493 | gi|1183933 |
| | hemoglobin, beta adult major chain [Mus musculus] | 451 | gi|31982300 |
| | beta-1-globin [Mus musculus] | 432 | gi|4760586 |
| | unnamed protein product [Mus musculus] | 352 | gi|12845853 |
| | alpha-globin [Mus musculus] | 321 | gi|49900 |
| | Trypsin precursor | 245 | gi|136429 |
| | Hemoglobin alpha subunit (Hemoglobin alpha chain) (Alpha-globin) | 172 | gi|122474 |
| | beta globin chain [Homo sapiens] | 134 | gi|66473265 |
| | beta globin [Callicebus torquatus] | 124 | gi|33415435 |
| | Analysis Of The Stabilization Of Hen Lysozyme With The Helix Dipole And Charged Side Chains | 104 | gi|2781269 |
| | Hemoglobin alpha subunit (Hemoglobin alpha chain) (Alpha-globin) | 96 | gi|122405 |
| C9 | Apolipoprotein A-II [Mus musculus] | 228 | gi|21618837 |
| | Trypsin precursor | 186 | gi|136429 |
| | alpha-globin [Mus musculus] | 138 | gi|49900 |
| | platelet basic protein [Mus musculus] | 127 | gi|13560694 |
| | Analysis Of The Stabilization Of Hen Lysozyme With The Helix Dipole And Charged Side Chains | 122 | gi|2781269 |
| | trypsinogen 10 [Mus musculus] | 68 | gi|2358087 |
| | apolipoprotein C2 [Mus musculus] | 67 | gi|817943 |
| | ubiquitin | 64 | gi|223061 |
| | adenylate kinase [Clonorchis sinensis] | 55 | gi|22652628 |
| C10 | keratin 1 [Homo sapiens] | 1055 | gi|7331218 |
| | cytokeratin 9 [Homo sapiens] | 508 | gi|435476 |
| | keratin 10 [Homo sapiens] | 414 | gi|40354192 |
| | epidermal cytokeratin 2 [Homo sapiens] | 252 | gi|181402 |
| | PREDICTED: similar to keratin 6 irs isoform 12 [Canis familiaris] | 176 | gi|73996330 |
| | Trypsin precursor | 166 | gi|136429 |
| | Analysis Of The Stabilization Of Hen Lysozyme With The Helix Dipole And Charged Side Chains | 129 | gi|2781269 |
| | epidermal keratin subunit II | 86 | gi|293686 |
| | thioredoxin [Escherichia coli] | 73 | gi|148071 |
| | trypsinogen 7 [Mus musculus] | 69 | gi|2358072 |
| C11 | apolipoprotein E | 374 | gi|192005 |
| | keratin 1 [Homo sapiens] | 303 | gi|7331218 |
| | Trypsin precursor | 266 | gi|136429 |
| | PREDICTED: similar to keratin 6 irs isoform 12 [Canis familiaris] | 167 | gi|73996330 |
| | Analysis Of The Stabilization Of Hen Lysozyme With The Helix Dipole And Charged Side Chains | 85 | gi|2781269 |
| D1 | Trypsin precursor | 216 | gi|136429 |
| | Analysis Of The Stabilization Of Hen Lysozyme With The Helix Dipole And Charged Side Chains | 104 | gi|2781269 |
| | lysozyme | 83 | gi|229157 |
| | pancreatic trypsin 1 [Rattus norvegicus] | 65 | gi|6981420 |
| | Hypothetical protein LOC338797 [Homo sapiens] | 55 | gi|70673359 |
| D2 | Chain E, Leech-Derived Tryptase InhibitorTRYPSIN COMPLEX | 139 | gi|3318722 |
| | epidermal cytokeratin 2 [Homo sapiens] | 93 | gi|181402 |
| | trypsinogen 10 [Mus musculus] | 64 | gi|2358087 |
| D3 | Trypsin precursor | 279 | gi|136429 |
| D4 | keratin 1 [Homo sapiens] | 302 | gi|7331218 |
| | Chain E, Leech-Derived Tryptase InhibitorTRYPSIN COMPLEX | 300 | gi|3318722 |
| | Unknown (protein for MGC: 116262) [Rattus norvegicus] | 190 | gi|71051822 |
| | PREDICTED: similar to keratin 6 irs isoform 12 [Canis familiaris] | 179 | gi|73996330 |
| | Analysis Of The Stabilization Of Hen Lysozyme With The Helix Dipole And Charged Side Chains | 78 | gi|2781269 |
| | unnamed protein product [Oryza sativa (japonica cultivar-group)] | 59 | gi|34906342 |
| D5 | Analysis Of The Stabilization Of Hen Lysozyme With The Helix Dipole And Charged Side Chains | 256 | gi|2781269 |
| | keratin 1 [Homo sapiens] | 230 | gi|7331218 |
| | Trypsin precursor | 178 | gi|136429 |
| | cytokeratin 9 [Homo sapiens] | 121 | gi|435476 |

TABLE 5-continued

| Sample | Protein ID | Score | Swiss-Prot Ascension |
|---|---|---|---|
| | trypsinogen 10 [*Mus musculus*] | 68 | gi|2358087 |
| | trypsinogen 7 [*Mus musculus*] | 68 | gi|2358072 |
| | membrane-bound transcriptional regulator LytR [*Bacillus cereus* ATCC 10987] | 56 | gi|42784428 |
| D6 | Trypsin precursor | 211 | gi|136429 |
| | Analysis Of The Stabilization Of Hen Lysozyme With The Helix Dipole And Charged Side Chains | 178 | gi|2781269 |
| | trypsinogen 7 [*Mus musculus*] | 70 | gi|2358072 |
| | trypsinogen 10 [*Mus musculus*] | 66 | gi|2358087 |
| D7 | Keratin 6A [*Homo sapiens*] | 491 | gi|14250682 |
| | Keratin 6B [*Homo sapiens*] | 435 | gi|21961227 |
| | PREDICTED: similar to Keratin, type I cytoskeletal 14 (Cytokeratin 14) (K14) (CK 14) isoform 3 [*Bos* | 372 | gi|76649703 |
| | keratin K5 | 359 | gi|386850 |
| | cytokeratin 9 [*Homo sapiens*] | 317 | gi|435476 |
| | keratin 1 [*Homo sapiens*] | 312 | gi|7331218 |
| | Trypsin precursor | 259 | gi|136429 |
| | PREDICTED: similar to keratin 6 irs isoform 12 [*Canis familiaris*] | 251 | gi|73996330 |
| | Analysis Of The Stabilization Of Hen Lysozyme With The Helix Dipole And Charged Side Chains | 144 | gi|2781269 |
| | thioredoxin [*Escherichia coli*] | 79 | gi|148071 |
| | countertrypin = fetuin type trypsin inhibitor [mice, plasma, Peptide Partial, 20 aa, segment 4 of 4] | 73 | gi|407619 |
| | countertrypin = fetuin type trypsin inhibitor [mice, plasma, Peptide Partial, 23 aa, segment 1 of 4] | 64 | gi|407613 |
| | trypsinogen 10 [*Mus musculus*] | 62 | gi|2358087 |
| | fetuin [*Mus musculus*] | 60 | gi|2546995 |
| D8 | hemoglobin, beta adult major chain [*Mus musculus*] | 324 | gi|31982300 |
| | Trypsin precursor | 260 | gi|136429 |
| | alpha-globin [*Mus musculus*] | 140 | gi|49900 |
| | apolipoprotein C-III [*Mus musculus*] | 129 | gi|15421856 |
| | complement component C3 precursor | 102 | gi|192392 |
| | lysozyme | 66 | gi|229157 |
| | Apolipoprotein A-II [*Mus musculus*] | 64 | gi|21618837 |
| | trypsinogen 10 [*Mus musculus*] | 64 | gi|2358087 |
| | nonsymbiotic hemoglobin [*Alnus firma*] | 64 | gi|84993584 |
| D9 | Trypsin precursor | 178 | gi|136429 |
| | Analysis Of The Stabilization Of Hen Lysozyme With The Helix Dipole And Charged Side Chains | 116 | gi|2781269 |
| | trypsinogen 10 [*Mus musculus*] | 69 | gi|2358087 |
| | membrane-bound transcriptional regulator LytR [*Bacillus cereus* ATCC 10987] | 55 | gi|42784428 |
| D10 | keratin 1 [*Homo sapiens*] | 500 | gi|17318569 |
| | inter alpha-trypsin inhibitor, heavy chain 4 [*Mus musculus*] | 400 | gi|9055252 |
| | Trypsin precursor | 261 | gi|136429 |
| | PREDICTED: similar to keratin 4 isoform 2 [*Bos taurus*] | 222 | gi|76617900 |
| | type II keratin Kb18 [*Rattus norvegicus*] | 182 | gi|57012352 |
| | PREDICTED: similar to keratin 6 irs isoform 12 [*Canis familiaris*] | 175 | gi|73996330 |
| | keratin complex 2, basic, gene 1 [*Mus musculus*] | 165 | gi|6678643 |
| | type II keratin Kb1 [*Rattus norvegicus*] | 165 | gi|57012354 |
| | PREDICTED: similar to keratin 25A [*Canis familiaris*] | 163 | gi|73965965 |
| | cytokeratin 9 [*Homo sapiens*] | 150 | gi|435476 |
| | larval keratin XLK [*Xenopus laevis*] | 141 | gi|13111394 |
| | thioredoxin [*Escherichia coli*] | 141 | gi|148071 |
| | Keratin, type II cytoskeletal 4 (Cytokeratin-4) (CK-4) (Keratin-4) (K4) (Cytoskeletal 57 kDa keratin) | 135 | gi|82654948 |
| | Three-Dimensional Structure Of *Escherichia Coli* Thioredoxin-S2 To 2.8 Angstroms Resolution | 133 | gi|230335 |
| | TPA: TPA_exp: keratin Kb40 [*Mus musculus*] | 125 | gi|46485130 |
| | inter-alpha-inhibitor H4 heavy chain [*Rattus norvegicus*] | 116 | gi|9506819 |
| | PREDICTED: similar to keratin 24 isoform 1 [*Bos taurus*] | 112 | gi|76644680 |
| | unnamed protein product [*Mus musculus*] | 109 | gi|26324736 |
| | TPA: TPA_exp: type II keratin Kb36 [*Mus musculus*] | 103 | gi|46485128 |
| | type I keratin 15 [*Protopterus aethiopicus*] | 102 | gi|57335394 |
| | thioredoxin 1 (TRX1) (TRX) [*Photorhabdus luminescens* subsp. *laumondii* TTO1] | 100 | gi|36787919 |
| | Analysis Of The Stabilization Of Hen Lysozyme With The Helix Dipole And Charged Side Chains | 100 | gi|2781269 |
| | LOC495267 protein [*Xenopus laevis*] | 98 | gi|54261576 |
| | hypothetical protein LOC77055 [*Mus musculus*] | 98 | gi|85701680 |
| | keratin 6 irs3 [*Homo sapiens*] | 96 | gi|27901522 |
| | thioredoxin [*Vibrio fischeri* ES114] | 90 | gi|59478765 |
| | Zgc: 92061 [*Danio rerio*] | 90 | gi|49902693 |

TABLE 5-continued

| Sample | Protein ID | Score | Swiss-Prot Ascension |
|---|---|---|---|
| | keratin 9 [*Canis familiaris*] | 79 | gi|62122767 |
| | phosphoserine phosphatase [*Picrophilus torridus* DSM 9790] | 79 | gi|48431085 |
| | pancreatic trypsin 1 [*Rattus norvegicus*] | 78 | gi|6981420 |
| | Zgc: 92035 [*Danio rerio*] | 74 | gi|49904349 |
| | PREDICTED: similar to Keratin, type I cytoskeletal 18 (Cytokeratin 18) (K18) (CK 18) [*Bos taurus*] | 71 | gi|76617986 |
| | keratin 19 [*Gallus gallus*] | 70 | gi|45384356 |
| | keratin complex 2, basic, gene 8 [*Mus musculus*] | 70 | gi|13624315 |
| | trypsinogen 10 [*Mus musculus*] | 62 | gi|2358087 |
| | hypothetical protein LOC496627 [*Xenopus tropicalis*] | 62 | gi|58332100 |
| | Transcriptional regulator, LytR family [*Bacillus thuringiensis* serovar *israelensis* ATCC 35646] | 58 | gi|75760497 |
| | PREDICTED: similar to keratin 5b [*Canis familiaris*] | 57 | gi|73996461 |
| | serine peptidase (alpha/beta hydrolase superfamily) fused to N-terminal uncharacterized domain specific to cyanobacteria [*Prochlorococcus marinus* str. NATL2A] | 55 | gi|72002395 |
| | PREDICTED: similar to otokeratin, partial [*Gallus gallus*] | 54 | gi|50795725 |
| D11 | unnamed protein product [*Mus musculus*] | 369 | gi|74146433 |
| | Trypsin precursor | 182 | gi|136429 |
| | thioredoxin [*Escherichia coli*] | 69 | gi|148071 |
| | lysozyme | 63 | gi|229157 |
| E1 | hemoglobin, beta adult major chain [*Mus musculus*] | 639 | gi|31982300 |
| | heamoglobin beta-1 chain [*Mus musculus*] | 636 | gi|1183932 |
| | haemoglobin beta-2 chain [*Mus musculus*] | 453 | gi|1183933 |
| | alpha-globin [*Mus musculus*] | 285 | gi|49900 |
| | Trypsin precursor | 274 | gi|136429 |
| | beta globin chain [*Homo sapiens*] | 131 | gi|66473265 |
| | Analysis Of The Stabilization Of Hen Lysozyme With The Helix Dipole And Charged Side Chains | 101 | gi|2781269 |
| | trypsinogen 10 [*Mus musculus*] | 66 | gi|2358087 |
| E2 | heamoglobin beta-1 chain [*Mus musculus*] | 476 | gi|1183932 |
| | hemoglobin, beta adult major chain [*Mus musculus*] | 475 | gi|31982300 |
| | haemoglobin beta-2 chain [*Mus musculus*] | 334 | gi|1183933 |
| | Trypsin precursor | 186 | gi|136429 |
| | alpha-globin [*Mus musculus*] | 184 | gi|49900 |
| | recombinant platelet factor 4 | 54 | gi|209286 |
| E3 | heamoglobin beta-1 chain [*Mus musculus*] | 606 | gi|1183932 |
| | hemoglobin, beta adult major chain [*Mus musculus*] | 590 | gi|31982300 |
| | haemoglobin beta-2 chain [*Mus musculus*] | 474 | gi|1183933 |
| | alpha-globin [*Mus musculus*] | 287 | gi|49900 |
| | Trypsin precursor | 279 | gi|136429 |
| | beta globin chain [*Homo sapiens*] | 89 | gi|66473265 |
| | Analysis Of The Stabilization Of Hen Lysozyme With The Helix Dipole And Charged Side Chains | 66 | gi|2781269 |
| E4 | hemoglobin, beta adult major chain [*Mus musculus*] | 440 | gi|31982300 |
| | heamoglobin beta-1 chain [*Mus musculus*] | 396 | gi|1183932 |
| | Trypsin precursor | 310 | gi|136429 |
| | Analysis Of The Stabilization Of Hen Lysozyme With The Helix Dipole And Charged Side Chains | 249 | gi|2781269 |
| | alpha-globin [*Mus musculus*] | 106 | gi|49900 |
| | Lysozyme C (1,4-beta-N-acetylmuramidase C) | 100 | gi|47117006 |
| | epidermal cytokeratin 2 [*Homo sapiens*] | 75 | gi|181402 |
| | membrane-bound transcriptional regulator LytR [*Bacillus cereus* ATCC 10987] | 56 | gi|42784428 |
| E5 | heamoglobin beta-1 chain [*Mus musculus*] | 477 | gi|1183932 |
| | hemoglobin, beta adult major chain [*Mus musculus*] | 464 | gi|31982300 |
| | haemoglobin beta-2 chain [*Mus musculus*] | 346 | gi|1183933 |
| | keratin 10 [*Homo sapiens*] | 300 | gi|40354192 |
| | alpha-globin [*Mus musculus*] | 247 | gi|49900 |
| | keratin 1 [*Homo sapiens*] | 225 | gi|17318569 |
| | Trypsin precursor | 174 | gi|136429 |
| | Analysis Of The Stabilization Of Hen Lysozyme With The Helix Dipole And Charged Side Chains | 155 | gi|2781269 |
| | epidermal cytokeratin 2 [*Homo sapiens*] | 132 | gi|181402 |
| | beta globin chain [*Homo sapiens*] | 93 | gi|66473265 |
| | Lysozyme C-3 (1,4-beta-N-acetylmuramidase) | 74 | gi|126595 |
| | major surface glycoprotein [*Pneumocystis carinii* f. sp. *hominis*] | 59 | gi|3560519 |
| | keratin 19 [*Homo sapiens*] | 58 | gi|7594734 |
| E6 | keratin 1 [*Homo sapiens*] | 845 | gi|17318569 |
| | Trypsin precursor | 296 | gi|136429 |
| | Chain E, Leech-Derived Tryptase Inhibitor TRYPSIN COMPLEX | 291 | gi|3318722 |
| | Analysis Of The Stabilization Of Hen Lysozyme With The Helix Dipole And Charged Side Chains | 267 | gi|2781269 |

TABLE 5-continued

| Sample | Protein ID | Score | Swiss-Prot Ascension |
|---|---|---|---|
| | PREDICTED: similar to keratin 6 irs isoform 12 [*Canis familiaris*] | 194 | gi|73996330 |
| | cytokeratin 9 [*Homo sapiens*] | 158 | gi|435476 |
| | Lysozyme C-3 (1,4-beta-N-acetylmuramidase) | 76 | gi|126595 |
| E7 | type I keratin 16; K16 [*Homo sapiens*] | 1177 | gi|1195531 |
| | Keratin 14 [*Homo sapiens*] | 887 | gi|17512236 |
| | Apoa4 protein [*Mus musculus*] | 475 | gi|14789706 |
| | Trypsin precursor | 178 | gi|136429 |
| | PREDICTED: similar to keratin 1 isoform 2 [*Bos taurus*] | 140 | gi|76617876 |
| | epidermal cytokeratin 2 [*Homo sapiens*] | 104 | gi|181402 |
| | mutant keratin 9 [*Homo sapiens*] | 102 | gi|1890020 |
| | lysozyme | 87 | gi|229157 |
| | gelsolin, cytosolic - mouse | 68 | gi|90508 |
| E8 | Trypsin precursor | 227 | gi|136429 |
| | unknown [*Theileria lestoquardi*] | 207 | gi|82622379 |
| | platelet basic protein [*Mus musculus*] | 158 | gi|13560694 |
| | Analysis Of The Stabilization Of Hen Lysozyme With The Helix Dipole And Charged Side Chains | 116 | gi|2781269 |
| | Apolipoprotein A-II [*Mus musculus*] | 115 | gi|21618837 |
| | hemoglobin beta | 112 | gi|229255 |
| | Apolipoprotein C-I (Apo-CI) (ApoC-I) | 67 | gi|114017 |
| E9 | Trypsin precursor | 251 | gi|136429 |
| | Coagulation factor II [*Mus musculus*] | 160 | gi|15489100 |
| | Analysis Of The Stabilization Of Hen Lysozyme With The Helix Dipole And Charged Side Chains | 105 | gi|2781269 |
| | Apolipoprotein A-II [*Mus musculus*] | 59 | gi|21618837 |
| E10 | PREDICTED: similar to Keratin, type I cytoskeletal 14 (Cytokeratin 14) (K14) (CK 14) isoform 3 [*Bos* | 311 | gi|76649703 |
| | gelsolin, cytosolic - mouse | 228 | gi|90508 |
| | Trypsin precursor | 113 | gi|136429 |
| | thioredoxin [*Escherichia coli*] | 81 | gi|148071 |
| E11 | Trypsin precursor | 180 | gi|136429 |
| | lysozyme | 86 | gi|229157 |
| | trypsinogen 10 [*Mus musculus*] | 61 | gi|2358087 |
| F1 | Trypsin precursor | 210 | gi|136429 |
| | hemoglobin beta | 136 | gi|229255 |
| | apolipoprotein C-III [*Mus musculus*] | 129 | gi|15421856 |
| | Analysis Of The Stabilization Of Hen Lysozyme With The Helix Dipole And Charged Side Chains | 77 | gi|2781269 |
| | complement component C3 precursor | 72 | gi|192392 |
| | trypsinogen 10 [*Mus musculus*] | 64 | gi|2358087 |
| | Apolipoprotein A-II [*Mus musculus*] | 60 | gi|21618837 |
| F2 | Trypsin precursor | 215 | gi|136429 |
| | apolipoprotein C-III [*Mus musculus*] | 120 | gi|15421856 |
| | complement component C3 precursor | 83 | gi|192392 |
| | trypsinogen 10 [*Mus musculus*] | 68 | gi|2358087 |
| | Apolipoprotein A-II [*Mus musculus*] | 60 | gi|21618837 |
| F3 | keratin 1 [*Homo sapiens*] | 264 | gi|7331218 |
| | Analysis Of The Stabilization Of Hen Lysozyme With The Helix Dipole And Charged Side Chains | 247 | gi|2781269 |
| | Trypsin precursor | 182 | gi|136429 |
| | keratin 10 [*Homo sapiens*] | 179 | gi|40354192 |
| | apolipoprotein C-III [*Mus musculus*] | 119 | gi|15421856 |
| | complement component C3 precursor | 79 | gi|192392 |
| | Apolipoprotein A-II [*Mus musculus*] | 62 | gi|21618837 |
| F4 | Chain E, Leech-Derived Tryptase InhibitorTRYPSIN COMPLEX | 336 | gi|3318722 |
| | Analysis Of The Stabilization Of Hen Lysozyme With The Helix Dipole And Charged Side Chains | 236 | gi|2781269 |
| | apolipoprotein C-III [*Mus musculus*] | 112 | gi|15421856 |
| | epidermal cytokeratin 2 [*Homo sapiens*] | 72 | gi|181402 |
| | complement component C3 precursor | 69 | gi|192392 |
| F5 | Trypsin precursor | 258 | gi|136429 |
| | Analysis Of The Stabilization Of Hen Lysozyme With The Helix Dipole And Charged Side Chains | 148 | gi|2781269 |
| | apolipoprotein C-III [*Mus musculus*] | 122 | gi|15421856 |
| | keratin 1, type II, cytoskeletal - human | 117 | gi|7428712 |
| | complement component C3 precursor | 104 | gi|192392 |
| | alpha-globin [*Mus musculus*] | 69 | gi|49900 |
| | Apolipoprotein A-II [*Mus musculus*] | 63 | gi|21618837 |
| F6 | keratin 1 [*Homo sapiens*] | 749 | gi|17318569 |
| | cytokeratin 9 [*Homo sapiens*] | 443 | gi|435476 |
| | keratin 10 [*Oryctolagus cuniculus*] | 277 | gi|87045985 |
| | Trypsin precursor | 195 | gi|136429 |
| | Analysis Of The Stabilization Of Hen Lysozyme With The Helix Dipole And Charged Side Chains | 124 | gi|2781269 |
| | thioredoxin [*Escherichia coli*] | 112 | gi|148071 |

TABLE 5-continued

| Sample | Protein ID | Score | Swiss-Prot Ascension |
|---|---|---|---|
| | Albumin 1 [*Mus musculus*] | 69 | gi|29612571 |
| | gelsolin, cytosolic - mouse | 58 | gi|90508 |
| | Tyrosyl-tRNA synthetase [*Lactobacillus sakei* subsp. *sakei* 23K] | 56 | gi|81428383 |
| F7 | Complement C3 precursor (HSE-MSF) [Contains: Complement C3 beta chain; Complement C3 alpha chain; C | 540 | gi|1352102 |
| | inter alpha-trypsin inhibitor, heavy chain 4 [*Mus musculus*] | 275 | gi|9055252 |
| | cytokeratin 9 [*Homo sapiens*] | 175 | gi|435476 |
| | Trypsin precursor | 171 | gi|136429 |
| | PREDICTED: similar to keratin 1 isoform 2 [*Bos taurus*] | 141 | gi|76617876 |
| | Analysis Of The Stabilization Of Hen Lysozyme With The Helix Dipole And Charged Side Chains | 103 | gi|2781269 |
| | apolipoprotein J; SGP-2; TRPM-2 [*Mus musculus*] | 94 | gi|6273853 |
| | apolipoprotein A-I precursor - mouse | 85 | gi|109571 |
| | trypsinogen 10 [*Mus musculus*] | 68 | gi|2358087 |
| | gelsolin, cytosolic - mouse | 55 | gi|90508 |
| F8 | keratin 1 [*Homo sapiens*] | 451 | gi|7331218 |
| | cytokeratin 9 [*Homo sapiens*] | 387 | gi|435476 |
| | keratin 10 [*Homo sapiens*] | 275 | gi|40354192 |
| | PREDICTED: similar to keratin 6 irs isoform 12 [*Canis familiaris*] | 188 | gi|73996330 |
| | Trypsin precursor | 175 | gi|136429 |
| | Analysis Of The Stabilization Of Hen Lysozyme With The Helix Dipole And Charged Side Chains | 105 | gi|2781269 |
| F9 | hemoglobin, beta adult major chain [*Mus musculus*] | 317 | gi|31982300 |
| | keratin 1 [*Homo sapiens*] | 247 | gi|7331218 |
| | Trypsin precursor | 190 | gi|136429 |
| | alpha-globin [*Mus musculus*] | 186 | gi|49900 |
| | Analysis Of The Stabilization Of Hen Lysozyme With The Helix Dipole And Charged Side Chains | 127 | gi|2781269 |
| | trypsinogen 10 [*Mus musculus*] | 68 | gi|2358087 |
| F10 | keratin 1 [*Homo sapiens*] | 2235 | gi|7331218 |
| | cytokeratin 9 [*Homo sapiens*] | 1608 | gi|435476 |
| | type II keratin subunit protein | 1400 | gi|386854 |
| | PREDICTED: similar to keratin 1; Keratin-1; cytokeratin 1; hair alpha protein [*Pan troglodytes*] | 697 | gi|55638031 |
| | keratin 10 [*Homo sapiens*] | 633 | gi|40354192 |
| | keratin 5 [*Rattus norvegicus*] | 469 | gi|33519156 |
| | PREDICTED: similar to keratin 4 isoform 2 [*Bos taurus*] | 428 | gi|76617900 |
| | epidermal cytokeratin 2 [*Homo sapiens*] | 394 | gi|181402 |
| | PREDICTED: similar to keratin 6 irs isoform 12 [*Canis familiaris*] | 376 | gi|73996330 |
| | PREDICTED: similar to Keratin, type I cytoskeletal 14 (Cytokeratin 14) (K14) (CK 14) isoform 3 [*Bos* | 307 | gi|76649703 |
| | Trypsin precursor | 264 | gi|136429 |
| | epidermal keratin subunit II | 222 | gi|293686 |
| | lysozyme | 94 | gi|229157 |
| | Albumin 1 [*Mus musculus*] | 87 | gi|29612571 |
| | trypsinogen 10 [*Mus musculus*] | 68 | gi|2358087 |
| | Short-chain dehydrogenase/reductase SDR [*Burkholderia* sp. 383] | 66 | gi|77965219 |
| F11 | hemoglobin, beta adult major chain [*Mus musculus*] | 495 | gi|31982300 |
| | heamoglobin beta-1 chain [*Mus musculus*] | 427 | gi|1183932 |
| | keratin 1 [*Homo sapiens*] | 333 | gi|7331218 |
| | Trypsin precursor | 268 | gi|136429 |
| | haemoglobin beta-2 chain [*Mus musculus*] | 216 | gi|1183933 |
| | cytokeratin 9 [*Homo sapiens*] | 184 | gi|435476 |
| | alpha-globin [*Mus musculus*] | 141 | gi|49900 |
| | Analysis Of The Stabilization Of Hen Lysozyme With The Helix Dipole And Charged Side Chains | 100 | gi|2781269 |
| | membrane-bound transcriptional regulator LytR [*Bacillus cereus* ATCC 10987] | 56 | gi|42784428 |
| G1 | Trypsin precursor | 267 | gi|136429 |
| | keratin 1 [*Homo sapiens*] | 198 | gi|7331218 |
| | Apolipoprotein A-II [*Mus musculus*] | 164 | gi|21618837 |
| | platelet basic protein [*Mus musculus*] | 134 | gi|13560694 |
| | ubiquitin | 121 | gi|223061 |
| | Analysis Of The Stabilization Of Hen Lysozyme With The Helix Dipole And Charged Side Chains | 93 | gi|2781269 |
| G2 | keratin 1 [*Homo sapiens*] | 621 | gi|17318569 |
| | keratin 10 [*Homo sapiens*] | 344 | gi|40354192 |
| | cytokeratin 9 [*Homo sapiens*] | 338 | gi|435476 |
| | epidermal cytokeratin 2 [*Homo sapiens*] | 293 | gi|181402 |
| | Analysis Of The Stabilization Of Hen Lysozyme With The Helix Dipole And Charged Side Chains | 270 | gi|2781269 |

TABLE 5-continued

| Sample | Protein ID | Score | Swiss-Prot Ascension |
|---|---|---|---|
|  | Trypsin precursor | 261 | gi|136429 |
|  | PREDICTED: similar to keratin 6 irs isoform 12 [*Canis familiaris*] | 179 | gi|73996330 |
|  | platelet basic protein [*Mus musculus*] | 143 | gi|13560694 |
|  | Apolipoprotein A-II [*Mus musculus*] | 130 | gi|21618837 |
|  | Lysozyme C (1,4-beta-N-acetylmuramidase C) | 124 | gi|47117006 |
|  | epidermal keratin subunit II | 92 | gi|293686 |
|  | ubiquitin | 66 | gi|223061 |
|  | trypsinogen 10 [*Mus musculus*] | 64 | gi|2358087 |
|  | alpha globin [*Homo sapiens*] | 62 | gi|28549 |
| G3 | Analysis Of The Stabilization Of Hen Lysozyme With The Helix Dipole And Charged Side Chains | 197 | gi|2781269 |
|  | Trypsin precursor | 173 | gi|136429 |
|  | Apolipoprotein A-II [*Mus musculus*] | 147 | gi|21618837 |
|  | platelet basic protein [*Mus musculus*] | 139 | gi|13560694 |
|  | ubiquitin | 78 | gi|223061 |
|  | trypsinogen 10 [*Mus musculus*] | 66 | gi|2358087 |
|  | membrane-bound transcriptional regulator LytR [*Bacillus cereus* ATCC 10987] | 55 | gi|42784428 |
| G4 | Trypsin precursor | 184 | gi|136429 |
|  | Analysis Of The Stabilization Of Hen Lysozyme With The Helix Dipole And Charged Side Chains | 150 | gi|2781269 |
|  | PREDICTED: similar to keratin 1 isoform 2 [*Bos taurus*] | 139 | gi|76617876 |
|  | platelet basic protein [*Mus musculus*] | 128 | gi|13560694 |
|  | Apolipoprotein A-II [*Mus musculus*] | 96 | gi|21618837 |
|  | membrane-bound transcriptional regulator LytR [*Bacillus cereus* ATCC 10987] | 54 | gi|42784428 |
| G5 | Trypsin precursor | 172 | gi|136429 |
|  | Analysis Of The Stabilization Of Hen Lysozyme With The Helix Dipole And Charged Side Chains | 147 | gi|2781269 |
|  | platelet basic protein [*Mus musculus*] | 127 | gi|13560694 |
|  | ubiquitin | 63 | gi|223061 |
|  | Apolipoprotein A-II [*Mus musculus*] | 60 | gi|21618837 |
| G6 | Inter alpha-trypsin inhibitor, heavy chain 4 [*Mus musculus*] | 1044 | gi|16741341 |
|  | keratin 1 [*Homo sapiens*] | 736 | gi|17318569 |
|  | cytokeratin 9 [*Homo sapiens*] | 483 | gi|435476 |
|  | Trypsin precursor | 253 | gi|136429 |
|  | PREDICTED: similar to keratin 6 irs isoform 12 [*Canis familiaris*] | 177 | gi|73996330 |
|  | thioredoxin [*Escherichia coli*] | 114 | gi|148071 |
|  | unnamed protein product [*Homo sapiens*] | 111 | gi|28317 |
|  | Analysis Of The Stabilization Of Hen Lysozyme With The Helix Dipole And Charged Side Chains | 107 | gi|2781269 |
|  | gelsolin, cytosolic - mouse | 74 | gi|90508 |
|  | trypsinogen 10 [*Mus musculus*] | 68 | gi|2358087 |
| G7 | apolipoprotein E | 814 | gi|192005 |
|  | Trypsin precursor | 245 | gi|136429 |
|  | inter alpha-trypsin inhibitor, heavy chain 4 [*Mus musculus*] | 213 | gi|9055252 |
|  | Analysis Of The Stabilization Of Hen Lysozyme With The Helix Dipole And Charged Side Chains | 149 | gi|2781269 |
|  | apolipoprotein A-I precursor - mouse | 86 | gi|109571 |
| G8 | Chain E, Leech-Derived Tryptase InhibitorTRYPSIN COMPLEX | 390 | gi|3318722 |
|  | Analysis Of The Stabilization Of Hen Lysozyme With The Helix Dipole And Charged Side Chains | 74 | gi|2781269 |
|  | trypsinogen 10 [*Mus musculus*] | 68 | gi|2358087 |
| G9 | Trypsin precursor | 271 | gi|136429 |
|  | apolipoprotein C-III [*Mus musculus*] | 116 | gi|15421856 |
|  | complement component C3 precursor | 80 | gi|192392 |
|  | trypsinogen 10 [*Mus musculus*] | 66 | gi|2358087 |
|  | Apolipoprotein A-II [*Mus musculus*] | 57 | gi|21618837 |
|  | nonsymbiotic hemoglobin [*Alnus firma*] | 55 | gi|84993584 |
| G10 | Keratin 6A [*Homo sapiens*] | 1409 | gi|15559584 |
|  | keratin 6C [*Homo sapiens*] | 1346 | gi|17505189 |
|  | keratin 6B [*Homo sapiens*] | 1295 | gi|5031841 |
|  | keratin 6 isoform K6e [*Homo sapiens*] | 1245 | gi|27465517 |
|  | Keratin 6B [*Homo sapiens*] | 1240 | gi|21961227 |
|  | keratin 1 [*Homo sapiens*] | 1182 | gi|17318569 |
|  | keratin 10 [*Homo sapiens*] | 938 | gi|40354192 |
|  | PREDICTED: similar to keratin 6 irs [*Pan troglodytes*] | 765 | gi|55638029 |
|  | cytokeratin 9 [*Homo sapiens*] | 440 | gi|435476 |

TABLE 5-continued

| Sample | Protein ID | Score | Swiss-Prot Ascension |
|---|---|---|---|
|  | PREDICTED: similar to keratin 6 irs isoform 12 [*Canis familiaris*] | 387 | gi|73996330 |
|  | Trypsin precursor | 180 | gi|136429 |
|  | keratin 19 [*Homo sapiens*] | 85 | gi|7594734 |
|  | hypothetical protein FG03380.1 [*Gibberella zeae* PH-1] | 61 | gi|46115076 |
| G11 | Trypsin precursor | 219 | gi|136429 |
|  | apolipoprotein C-III [*Mus musculus*] | 119 | gi|15421856 |
|  | complement component C3 precursor | 94 | gi|192392 |
| H1 | Analysis Of The Stabilization Of Hen Lysozyme With The Helix Dipole And Charged Side Chains | 232 | gi|2781269 |
|  | Trypsin precursor | 183 | gi|136429 |
| H2 | Analysis Of The Stabilization Of Hen Lysozyme With The Helix Dipole And Charged Side Chains | 214 | gi|2781269 |
|  | Trypsin precursor | 188 | gi|136429 |
| H3 | Trypsin precursor | 182 | gi|136429 |
|  | Analysis Of The Stabilization Of Hen Lysozyme With The Helix Dipole And Charged Side Chains | 96 | gi|2781269 |
|  | unnamed protein product [*Tetraodon nigroviridis*] | 63 | gi|47227197 |
| H4 | Trypsin precursor | 161 | gi|136429 |
|  | Analysis Of The Stabilization Of Hen Lysozyme With The Helix Dipole And Charged Side Chains | 100 | gi|2781269 |
|  | trypsinogen 10 [*Mus musculus*] | 66 | gi|2358087 |
| H5 | Trypsin precursor | 259 | gi|136429 |
|  | Analysis Of The Stabilization Of Hen Lysozyme With The Helix Dipole And Charged Side Chains | 148 | gi|2781269 |
|  | trypsinogen 10 [*Mus musculus*] | 62 | gi|2358087 |
|  | membrane-bound transcriptional regulator LytR [*Bacillus cereus* ATCC 10987] | 56 | gi|42784428 |
| H6 | Gsn protein [*Mus musculus*] | 1111 | gi|18606238 |
|  | keratin 1 [*Homo sapiens*] | 404 | gi|7331218 |
|  | cytokeratin 9 [*Homo sapiens*] | 399 | gi|435476 |
|  | inter alpha-trypsin inhibitor, heavy chain 4 [*Mus musculus*] | 399 | gi|9055252 |
|  | Trypsin precursor | 178 | gi|136429 |
|  | thioredoxin [*Escherichia coli*] | 103 | gi|148071 |
|  | lysozyme | 70 | gi|229157 |
|  | trypsinogen 10 [*Mus musculus*] | 64 | gi|2358087 |
| H7 | unnamed protein product [*Mus musculus*] | 856 | gi|74146433 |
|  | keratin 1 [*Homo sapiens*] | 273 | gi|17318569 |
|  | epidermal cytokeratin 2 [*Homo sapiens*] | 269 | gi|181402 |
|  | Chain E, Leech-Derived Tryptase InhibitorTRYPSIN COMPLEX | 211 | gi|3318722 |
|  | keratin 10 [*Oryctolagus cuniculus*] | 156 | gi|87045985 |
|  | thioredoxin [*Escherichia coli*] | 84 | gi|148071 |
|  | thrombospondin | 65 | gi|554390 |
| H8 | Trypsin precursor | 305 | gi|136429 |
|  | Coagulation factor II [*Mus musculus*] | 185 | gi|15489100 |
|  | PREDICTED: similar to keratin 1 isoform 2 [*Bos taurus*] | 135 | gi|76617876 |
|  | Analysis Of The Stabilization Of Hen Lysozyme With The Helix Dipole And Charged Side Chains | 127 | gi|2781269 |
|  | apolipoprotein A-I precursor - mouse | 107 | gi|109571 |
|  | PREDICTED: similar to trypsinogen 7 isoform 4 [*Canis familiaris*] | 96 | gi|73978531 |
|  | trypsinogen 10 [*Mus musculus*] | 68 | gi|2358087 |
|  | membrane-bound transcriptional regulator LytR [*Bacillus cereus* ATCC 10987] | 56 | gi|42784428 |
| H9 | keratin 1 [*Homo sapiens*] | 426 | gi|7331218 |
|  | Apolipoprotein A-II [*Mus musculus*] | 280 | gi|21618837 |
|  | Trypsin precursor | 267 | gi|136429 |
|  | cytokeratin 9 [*Homo sapiens*] | 156 | gi|435476 |
|  | platelet basic protein [*Mus musculus*] | 103 | gi|13560694 |
|  | trypsinogen 10 [*Mus musculus*] | 69 | gi|2358087 |
| H10 | Keratin 6A [*Homo sapiens*] | 1851 | gi|15559584 |
|  | keratin 6C [*Homo sapiens*] | 1802 | gi|17505189 |
|  | TPA: TPA_exp: type II keratin K6h [*Homo sapiens*] | 1665 | gi|32964837 |
|  | keratin 6 isoform K6e [*Homo sapiens*] | 1650 | gi|27465517 |
|  | Keratin 6B [*Homo sapiens*] | 1581 | gi|21961227 |
|  | keratin 10 [*Homo sapiens*] | 1196 | gi|40354192 |
|  | keratin 1 [*Homo sapiens*] | 1190 | gi|17318569 |
|  | Keratin 5 [*Homo sapiens*] | 1076 | gi|18999435 |
|  | type II keratin subunit protein | 871 | gi|386854 |
|  | epidermal keratin subunit II | 603 | gi|293686 |
|  | PREDICTED: similar to keratin 6 irs isoform 12 [*Canis familiaris*] | 601 | gi|73996330 |
|  | cytokeratin 9 [*Homo sapiens*] | 575 | gi|435476 |
|  | keratin 3 [*Homo sapiens*] | 458 | gi|42760012 |
|  | type II alpha-keratin IIA [*Gallus gallus*] | 326 | gi|46399073 |

TABLE 5-continued

| Sample | Protein ID | Score | Swiss-Prot Ascension |
|---|---|---|---|
| | Chain E, Leech-Derived Tryptase InhibitorTRYPSIN COMPLEX | 315 | gi|3318722 |
| | K15 intermediate filament type I keratin [Ovis aries] | 279 | gi|3550539 |
| | type I keratin 10 [Protopterus aethiopicus] | 100 | gi|57335414 |
| | PREDICTED: similar to trypsinogen 7 isoform 4 [Canis familiaris] | 97 | gi|73978531 |
| | keratin 19 [Homo sapiens] | 91 | gi|7594734 |
| | trypsinogen 7 [Mus musculus] | 74 | gi|2358072 |
| | hypothetical protein FG03380.1 [Gibberella zeae PH-1] | 61 | gi|46115076 |
| | membrane-bound transcriptional regulator LytR [Bacillus cereus ATCC 10987] | 56 | gi|42784428 |
| H11 | Trypsin precursor | 85 | gi|136429 |
| | platelet basic protein [Mus musculus] | 80 | gi|13560694 |
| | possible glycosyltransferase [Synechococcus sp. WH 8102] | 65 | gi|33632163 |
| | keratin 10 [Homo sapiens] | 57 | gi|40354192 |
| | Apolipoprotein A-II [Mus musculus] | 56 | gi|21618837 |

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| B9 | adenylate kinase [Clonorchis sinensis] | 59 | gi|22652628 | 2 | | | |
| B7 | Albumin 1 [Mus musculus] | 1536 | gi|29612571 | 3 | | | |
| A5 | alpha globin [Homo sapiens] | 147 | gi|28549 | 4 | | | |
| C7 | alpha-fetoprotein | 61 | gi|191765 | 2 | | | |
| C8 | alpha-globin [Mus musculus] | 321 | gi|49900 | 16 | | | |
| G2 | Analysis Of The Stabilization Of Hen Lysozyme With The Helix Dipole And Charged Side Chains | 270 | gi|2781269 | 59 | | | + |
| E7 | Apoa4 protein [Mus musculus] | 475 | gi|14789706 | 1 | | | |
| A8 | apolipoprotein A-I precursor - mouse | 112 | gi|109571 | 5 | | | |
| H9 | Apolipoprotein A-II [Mus musculus] | 280 | gi|21618837 | 22 | | | |
| C9 | apolipoprotein C2 [Mus musculus] | 67 | gi|817943 | 1 | | | |
| E8 | Apolipoprotein C-I (Apo-CI) (ApoC-I) | 67 | gi|114017 | 2 | | | |
| F1 | apolipoprotein C-III [Mus musculus] | 129 | gi|15421856 | 15 | | | |
| G7 | apolipoprotein E | 814 | gi|192005 | 2 | | | |
| F7 | apolipoprotein J; SGP-2; TRPM-2 [Mus musculus] | 94 | gi|6273853 | 1 | | | |
| C8 | beta globin [Callicebus torquatus] | 124 | gi|33415435 | 1 | | | |
| C8 | beta globin chain [Homo sapiens] | 134 | gi|66473265 | 6 | | | |
| C8 | beta-1-globin [Mus musculus] | 432 | gi|4760586 | 1 | | | |
| B12 | calmodulin-like 5 [Homo sapiens] | 195 | gi|55859601 | 1 | | | |
| F4 | Chain E, Leech-Derived Tryptase InhibitorTRYPSIN COMPLEX | 336 | gi|3318722 | 10 | | + | |
| H8 | Coagulation factor II [Mus musculus] | 185 | gi|15489100 | 2 | | | |

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| F7 | Complement C3 precursor (HSE-MSF) [Contains: Complement C3 beta chain; Complement C3 alpha chain; C | 540 | gi\|1352102 | 3 | | | |
| F5 | complement component C3 precursor | 104 | gi\|192392 | 15 | | | |
| D7 | countertrypin = fetuin type trypsin inhibitor [mice, plasma, Peptide Partial, 20 aa, segment 4 of 4] | 73 | gi\|407619 | 2 | | + | |
| B8 | cystatin C precursor [Mus musculus] | 98 | gi\|11762010 | 1 | | | |
| F10 | cytokeratin 9 [Homo sapiens] | 1608 | gi\|435476 | 27 | + | | |
| B9 | epidermal cytokeratin 2 [Homo sapiens] | 700 | gi\|181402 | 12 | + | | |
| H10 | epidermal keratin subunit II | 603 | gi\|293686 | 6 | + | | |
| D7 | fetuin [Mus musculus] | 60 | gi\|2546995 | 1 | | | |
| B8 | Flp pilus assembly protein CpaB family [Burkholderia thailandensis E264] | 57 | gi\|83719123 | 1 | | | |
| E10 | gelsolin, cytosolic - mouse | 228 | gi\|90508 | 6 | | | |
| B12 | glyceraldehyde-3-phosphate dehydrogenase [Homo sapiens] | 62 | gi\|31645 | 1 | | | |
| H6 | Gsn protein [Mus musculus] | 1111 | gi\|18606238 | 1 | | | |
| C8 | haemoglobin beta-2 chain [Mus musculus] | 493 | gi\|1183933 | 11 | | | |
| E1 | heamoglobin beta-1 chain [Mus musculus] | 636 | gi\|1183932 | 14 | | | |
| C8 | Hemoglobin alpha subunit (Hemoglobin alpha chain) (Alpha-globin) | 96 | gi\|122405 | 1 | | | |
| C8 | Hemoglobin alpha subunit (Hemoglobin alpha chain) (Alpha-globin) | 172 | gi\|122474 | 1 | | | |
| F1 | hemoglobin beta | 136 | gi\|229255 | 2 | | | |
| A1 | hemoglobin beta | 182 | gi\|229301 | 1 | | | |
| A4 | Hemoglobin beta subunit (Hemoglobin beta chain) (Beta-globin) | 58 | gi\|122606 | 1 | | | |
| A3 | Hemoglobin beta subunit (Hemoglobin beta chain) (Beta-globin) | 165 | gi\|122643 | 2 | | | |
| E1 | hemoglobin, beta adult major chain [Mus musculus] | 639 | gi\|31982300 | 10 | | | |
| A7 | histidine-rich glycoprotein [Mus musculus] | 111 | gi\|11066003 | 1 | | | |
| H10 | hypothetical protein FG03380.1 [Gibberella zeae PH-1] | 61 | gi\|46115076 | 3 | | | |
| D1 | Hypothetical protein LOC338797 [Homo sapiens] | 55 | gi\|70673359 | 1 | | | |
| D10 | hypothetical protein LOC496627 [Xenopus tropicalis] | 62 | gi\|58332100 | 1 | | | |
| D10 | hypothetical protein LOC77055 [Mus musculus] | 98 | gi\|85701680 | 1 | | | |

-continued

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| B7 | hypothetical protein SAV6338 [*Streptomyces avermitilis* MA-4680] | 62 | gi\|29832880 | 1 | | | |
| G6 | Inter alpha-trypsin inhibitor, heavy chain 4 [*Mus musculus*] | 1044 | gi\|16741341 | 1 | | | |
| D10 | inter alpha-trypsin inhibitor, heavy chain 4 [*Mus musculus*] | 400 | gi\|9055252 | 6 | | | |
| D10 | inter-alpha-inhibitor H4 heavy chain [*Rattus norvegicus*] | 116 | gi\|9506819 | 1 | | | |
| H10 | K15 intermediate filament type I keratin [*Ovis aries*] | 279 | gi\|3550539 | 1 | + | | |
| B12 | keratin | 437 | gi\|386848 | 1 | + | | |
| B7 | keratin 1 [*Homo sapiens*] | 1518 | gi\|17318569 | 21 | + | | |
| F10 | keratin 1 [*Homo sapiens*] | 2235 | gi\|7331218 | 18 | + | | |
| B6 | keratin 1, type II, cytoskeletal - human | 142 | gi\|7428712 | 4 | + | | |
| H10 | keratin 10 [*Homo sapiens*] | 1196 | gi\|40354192 | 18 | + | | |
| C2 | keratin 10 [*Oryctolagus cuniculus*] | 288 | gi\|87045985 | 4 | + | | |
| A11 | Keratin 14 [*Homo sapiens*] | 1134 | gi\|17512236 | 2 | + | | |
| B11 | keratin 15 [*Homo sapiens*] | 166 | gi\|30583361 | 1 | + | | |
| B12 | Keratin 17 [*Homo sapiens*] | 516 | gi\|48735384 | 1 | + | | |
| D10 | keratin 19 [*Gallus gallus*] | 70 | gi\|45384356 | 1 | + | | |
| H10 | keratin 19 [*Homo sapiens*] | 91 | gi\|7594734 | 4 | + | | |
| H10 | keratin 3 [*Homo sapiens*] | 458 | gi\|42760012 | 1 | + | | |
| H10 | Keratin 5 [*Homo sapiens*] | 1076 | gi\|18999435 | 1 | + | | |
| A11 | keratin 5 [*Homo sapiens*] | 349 | gi\|4557890 | 1 | + | | |
| F10 | keratin 5 [*Rattus norvegicus*] | 469 | gi\|33519156 | 1 | + | | |
| D10 | keratin 6 irs3 [*Homo sapiens*] | 96 | gi\|27901522 | 1 | + | | |
| H10 | keratin 6 isoform K6e [*Homo sapiens*] | 1650 | gi\|27465517 | 2 | + | | |
| B10 | Keratin 6A [*Homo sapiens*] | 653 | gi\|14250682 | 3 | + | | |
| H10 | Keratin 6A [*Homo sapiens*] | 1851 | gi\|15559584 | 2 | + | | |
| H10 | Keratin 6B [*Homo sapiens*] | 1581 | gi\|21961227 | 5 | + | | |
| G10 | keratin 6B [*Homo sapiens*] | 1295 | gi\|5031841 | 1 | + | | |
| H10 | keratin 6C [*Homo sapiens*] | 1802 | gi\|17505189 | 3 | + | | |
| D10 | keratin 9 [*Canis familiaris*] | 79 | gi\|62122767 | 1 | + | | |
| B10 | keratin complex 1, acidic, gene 14 [*Mus musculus*] | 311 | gi\|21489935 | 1 | + | | |
| D10 | keratin complex 2, basic, gene 1 [*Mus musculus*] | 165 | gi\|6678643 | 1 | + | | |
| D10 | keratin complex 2, basic, gene 8 [*Mus musculus*] | 70 | gi\|13624315 | 1 | + | | |
| B12 | keratin K5 | 390 | gi\|386850 | 3 | + | | |
| B12 | keratin type 16 | 283 | gi\|186685 | 1 | + | | |
| A11 | keratin type II | 492 | gi\|386849 | 1 | + | | |
| D10 | Keratin, type II cytoskeletal 4 (Cytokeratin-4) (CK-4) (Keratin-4) (K4) (Cytoskeletal 57 kDa keratin) | 135 | gi\|82654948 | 1 | + | | |
| D10 | larval keratin XLK [*Xenopus laevis*] | 141 | gi\|13111394 | 1 | + | | |
| D10 | LOC495267 protein [*Xenopus laevis*] | 98 | gi\|54261576 | 1 | | | |
| C2 | lysozyme | 99 | gi\|229157 | 15 | | | + |

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| B8 | lysozyme | 73 | gi\|841217 | 1 | | | + |
| G2 | Lysozyme C (1,4-beta-N-acetylmuramidase C) | 124 | gi\|47117006 | 3 | | | + |
| E6 | Lysozyme C-3 (1,4-beta-N-acetylmuramidase) | 76 | gi\|126595 | 2 | | | + |
| E5 | major surface glycoprotein [*Pneumocystis carinii* f. sp. *hominis*] | 59 | gi\|3560519 | 1 | | | |
| H8 | membrane-bound transcriptional regulator LytR [*Bacillus cereus* ATCC 10987] | 56 | gi\|42784428 | 13 | | | |
| E7 | mutant keratin 9 [*Homo sapiens*] | 102 | gi\|1890020 | 1 | + | | |
| D8 | nonsymbiotic hemoglobin [*Alnus firma*] | 64 | gi\|84993584 | 3 | | | |
| D10 | pancreatic trypsin 1 [*Rattus norvegicus*] | 78 | gi\|6981420 | 2 | | + | |
| B8 | parvalbumin [*Mus musculus*] | 77 | gi\|509139 | 1 | | | |
| D10 | phosphoserine phosphatase [*Picrophilus torridus* DSM 9790] | 79 | gi\|48431085 | 1 | | | |
| C2 | platelet basic protein [*Mus musculus*] | 166 | gi\|13560694 | 15 | | | |
| A2 | platelet factor 4 [*Mus musculus*] | 87 | gi\|13560695 | 1 | | | |
| H11 | possible glycosyltransferase [*Synechococcus* sp. WH 8102] | 65 | gi\|33632163 | 1 | | | |
| B8 | PREDICTED: similar to keratin 1 isoform 2 [*Bos taurus*] | 243 | gi\|76617876 | 5 | + | | |
| F10 | PREDICTED: similar to keratin 1; Keratin-1; cytokeratin 1; hair alpha protein [*Pan troglodytes*] | 697 | gi\|55638031 | 2 | + | | |
| A11 | PREDICTED: similar to keratin 15 [*Bos taurus*] | 209 | gi\|61813798 | 1 | + | | |
| B12 | PREDICTED: similar to keratin 17 [*Pan troglodytes*] | 184 | gi\|55644941 | 1 | + | | |
| D10 | PREDICTED: similar to keratin 24 isoform 1 [*Bos taurus*] | 112 | gi\|76644680 | 1 | + | | |
| D10 | PREDICTED: similar to keratin 25A [*Canis familiaris*] | 163 | gi\|73965965 | 1 | + | | |
| F10 | PREDICTED: similar to keratin 4 isoform 2 [*Bos taurus*] | 428 | gi\|76617900 | 2 | + | | |
| D10 | PREDICTED: similar to keratin 5b [*Canis familiaris*] | 57 | gi\|73996461 | 1 | + | | |
| G10 | PREDICTED: similar to keratin 6 irs [*Pan troglodytes*] | 765 | gi\|55638029 | 3 | + | | |
| H10 | PREDICTED: similar to keratin 6 irs isoform 12 [*Canis familiaris*] | 601 | gi\|73996330 | 24 | + | | |
| A11 | PREDICTED: similar to keratin 8, type II cytoskeletal - human [*Pan troglodytes*] | 90 | gi\|55638407 | 1 | + | | |
| B10 | PREDICTED: similar to Keratin, type I cytoskeletal 14 (Cytokeratin 14) (K14) (CK 14) isoform 3 [*Bos* | 445 | gi\|76649703 | 5 | + | | |

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| D10 | PREDICTED: similar to Keratin, type I cytoskeletal 18 (Cytokeratin 18) (K18) (CK 18) [*Bos taurus*] | 71 | gi\|76617986 | 1 | + | | |
| B8 | PREDICTED: similar to Keratin, type II cytoskeletal 5 (Cytokeratin 5) (K5) (CK 5) (58 kDa cytokerat | 262 | gi\|73996312 | 1 | + | | |
| B10 | PREDICTED: similar to Keratin, type II cytoskeletal 8 (Cytokeratin 8) (Cytokeratin endo A) [*Rattus* | 87 | gi\|62657929 | 1 | + | | |
| B12 | PREDICTED: similar to Keratin, type II cytoskeletal 8 (Cytokeratin-8) (CK-8) (Keraton-8) (K8) [*Homo* | 80 | gi\|88988823 | 1 | + | | |
| D10 | PREDICTED: similar to otokeratin, partial [*Gallus gallus*] | 54 | gi\|50795725 | 1 | + | | |
| B10 | PREDICTED: similar to trypsinogen 7 isoform 4 [*Canis familiaris*] | 108 | gi\|73978531 | 4 | | + | |
| B8 | profilin 1 [*Mus musculus*] | 111 | gi\|56206029 | 1 | | | |
| E2 | recombinant platelet factor 4 | 54 | gi\|209286 | 1 | | | |
| D10 | serine peptidase (alpha/beta hydrolase superfamily) fused to N-terminal uncharacterized domain specific to cyanobacteria [*Prochlorococcus marinus* str. NATL2A] | 55 | gi\|72002395 | 1 | | | |
| F10 | Short-chain dehydrogenase/reductase SDR [*Burkholderia* sp. 383] | 66 | gi\|77965219 | 3 | | | |
| D10 | thioredoxin [*Escherichia coli*] | 141 | gi\|148071 | 12 | | | |
| D10 | thioredoxin [*Vibrio fischeri* ES114] | 90 | gi\|59478765 | 1 | | | |
| D10 | thioredoxin 1 (TRX1) (TRX) [*Photorhabdus luminescens* subsp. *laumondii* TT01] | 100 | gi\|36787919 | 1 | | | |
| D10 | Three-Dimensional Structure Of *Escherichia Coli* Thioredoxin-S2 To 2.8 Angstroms Resolution | 133 | gi\|230335 | 1 | | | |
| H7 | thrombospondin | 65 | gi\|554390 | 1 | | | |
| D10 | TPA: TPA_exp: keratin Kb40 [*Mus musculus*] | 125 | gi\|46485130 | 1 | + | | |
| H10 | TPA: TPA_exp: type II keratin K6h [*Homo sapiens*] | 1665 | gi\|32964837 | 1 | + | | |
| D10 | TPA: TPA_exp: type II keratin Kb36 [*Mus musculus*] | 103 | gi\|46485128 | 1 | + | | |
| D10 | Transcriptional regulator, LytR family [*Bacillus thuringiensis* serovar *israelensis* ATCC 35646] | 58 | gi\|75760497 | 1 | | | |
| A7 | transferrin [*Mus musculus*] | 304 | gi\|17046471 | 1 | | | |

-continued

| Sample | Protein ID | Score | Swiss-Prot Ascension | Times identified | Keratin or keratin related proteins | Trypsin or trypsin related proteins | Lysozyme or lysozyme related proteins |
|---|---|---|---|---|---|---|---|
| B8 | Transthyretin [*Mus musculus*] | 95 | gi|56541070 | 1 | | | |
| C6 | trypsin (EC 3.4.21.4) precursor - bovine | 88 | gi|67549 | 1 | | + | |
| E4 | Trypsin precursor | 310 | gi|136429 | 79 | | + | |
| A3 | trypsinogen 10 [*Mus musculus*] | 71 | gi|2358087 | 41 | | + | |
| H10 | trypsinogen 7 [*Mus musculus*] | 74 | gi|2358072 | 6 | | + | |
| H10 | type I keratin 10 [*Protopterus aethiopicus*] | 100 | gi|57335414 | 4 | + | | |
| D10 | type I keratin 15 [*Protopterus aethiopicus*] | 102 | gi|57335394 | 1 | + | | |
| A11 | type I keratin 16; K16 [*Homo sapiens*] | 1301 | gi|1195531 | 4 | + | | |
| H10 | type II alpha-keratin IIA [*Gallus gallus*] | 326 | gi|46399073 | 1 | + | | |
| B10 | type II alpha-keratin IIB [*Gallus gallus*] | 89 | gi|46399075 | 1 | + | | |
| C7 | type II keratin Kb1 [*Rattus norvegicus*] | 319 | gi|57012354 | 2 | + | | |
| D10 | type II keratin Kb18 [*Rattus norvegicus*] | 182 | gi|57012352 | 1 | + | | |
| F10 | type II keratin subunit protein | 1400 | gi|386854 | 2 | + | | |
| F6 | Tyrosyl-tRNA synthetase [*Lactobacillus sakei* subsp. *sakei* 23K] | 56 | gi|81428383 | 1 | | | |
| G1 | ubiquitin | 121 | gi|223061 | 8 | | | |
| D4 | Unknown (protein for MGC: 116262) [*Rattus norvegicus*] | 190 | gi|71051822 | 1 | | | |
| E8 | unknown [*Theileria lestoquardi*] | 207 | gi|82622379 | 1 | | | |
| G6 | unnamed protein product [*Homo sapiens*] | 111 | gi|28317 | 1 | | | |
| C8 | unnamed protein product [*Mus musculus*] | 352 | gi|12845853 | 1 | | | |
| D10 | unnamed protein product [*Mus musculus*] | 109 | gi|26324736 | 1 | | | |
| H7 | unnamed protein product [*Mus musculus*] | 856 | gi|74146433 | 2 | | | |
| D4 | unnamed protein product [*Oryza sativa* (*japonica* cultivar-group)] | 59 | gi|34906342 | 1 | | | |
| H3 | unnamed protein product [*Tetraodon nigroviridis*] | 63 | gi|47227197 | 1 | | | |
| D10 | Zgc: 92035 [*Danio rerio*] | 74 | gi|49904349 | 1 | | | |
| D10 | Zgc: 92061 [*Danio rerio*] | 90 | gi|49902693 | 1 | | | |
| Total Numbers | | | | 707 | | | |
| | keratin or keratin related proteins | | | 225 | | | |
| | trypsin or trypsin related proteins | | | 145 | | | |
| | lysozyme or lysozyme related proteins | | | 80 | | | |
| Total protein numbers without keratin/trypsin/lysozyme | | | | 257 | | | |
| Unique protein numbers | | | | 154 | | | |
| | keratin or keratin related proteins | | | 64 | | | |
| | trypsin or trypsin related proteins | | | 7 | | | |
| | lysozyme or lysozyme related proteins | | | 6 | | | |
| Unique protein numbers without keratin/trypsin/lysozyme | | | | 77 | | | |

TABLE 7

| Sample | Protein ID | Score | Swiss-Prot Ascension | Times identified |
|---|---|---|---|---|
| H9 | Apolipoprotein A-II [*Mus musculus*] | 280 | gi|21618837 | 22 |
| C8 | alpha-globin [*Mus musculus*] | 321 | gi|49900 | 16 |
| C2 | platelet basic protein [*Mus musculus*] | 166 | gi|13560694 | 15 |
| F1 | apolipoprotein C-III [*Mus musculus*] | 129 | gi|15421856 | 15 |
| F5 | complement component C3 precursor | 104 | gi|192392 | 15 |
| E1 | heamoglobin beta-1 chain [*Mus musculus*] | 636 | gi|1183932 | 14 |
| H8 | membrane-bound transcriptional regulator LytR [*Bacillus cereus* ATCC 10987] | 56 | gi|42784428 | 13 |
| D10 | thioredoxin [*Escherichia coli*] | 141 | gi|148071 | 12 |
| C8 | haemoglobin beta-2 chain [*Mus musculus*] | 493 | gi|1183933 | 11 |
| E1 | hemoglobin, beta adult major chain [*Mus musculus*] | 639 | gi|31982300 | 10 |
| F4 | Chain E, Leech-Derived Tryptase InhibitorTRYPSIN COMPLEX | 336 | gi|3318722 | 10 |
| G1 | ubiquitin | 121 | gi|223061 | 8 |
| D10 | inter alpha-trypsin inhibitor, heavy chain 4 [*Mus musculus*] | 400 | gi|9055252 | 6 |
| E10 | gelsolin, cytosolic - mouse | 228 | gi|90508 | 6 |
| C8 | beta globin chain [*Homo sapiens*] | 134 | gi|66473265 | 6 |
| A8 | apolipoprotein A-I precursor - mouse | 112 | gi|109571 | 5 |
| A5 | alpha globin [*Homo sapiens*] | 147 | gi|28549 | 4 |
| B7 | Albumin 1 [*Mus musculus*] | 1536 | gi|29612571 | 3 |
| F7 | Complement C3 precursor (HSE-MSF) [Contains: Complement C3 beta chain; Complement C3 alpha chain; C | 540 | gi|1352102 | 3 |
| F10 | Short-chain dehydrogenase/reductase SDR [*Burkholderia* sp. 383] | 66 | gi|77965219 | 3 |
| D8 | nonsymbiotic hemoglobin [*Alnus firma*] | 64 | gi|84993584 | 3 |
| H10 | hypothetical protein FG03380.1 [*Gibberella zeae* PH-1] | 61 | gi|46115076 | 3 |
| H7 | unnamed protein product [*Mus musculus*] | 856 | gi|74146433 | 2 |
| G7 | apolipoprotein E | 814 | gi|192005 | 2 |
| H8 | Coagulation factor II [*Mus musculus*] | 185 | gi|15489100 | 2 |
| A3 | Hemoglobin beta subunit (Hemoglobin beta chain) (Beta-globin) | 165 | gi|122643 | 2 |
| F1 | hemoglobin beta | 136 | gi|229255 | 2 |
| D7 | countertrypin = fetuin type trypsin inhibitor [mice, plasma, Peptide Partial, 20 aa, segment 4 of 4] | 73 | gi|407619 | 2 |
| E8 | Apolipoprotein C-I (Apo-CI) (ApoC-I) | 67 | gi|114017 | 2 |
| C7 | alpha-fetoprotein | 61 | gi|191765 | 2 |
| B9 | adenylate kinase [*Clonorchis sinensis*] | 59 | gi|22652628 | 2 |
| H6 | Gsn protein [*Mus musculus*] | 1111 | gi|18606238 | 1 |
| G6 | Inter alpha-trypsin inhibitor, heavy chain 4 [*Mus musculus*] | 1044 | gi|16741341 | 1 |
| E7 | Apoa4 protein [*Mus musculus*] | 475 | gi|14789706 | 1 |
| C8 | beta-1-globin [*Mus musculus*] | 432 | gi|4760586 | 1 |
| C8 | Top of Form unnamed protein product [*Mus musculus*] | 352 | gi|12845853 | 1 |
| A7 | transferrin [*Mus musculus*] | 304 | gi|17046471 | 1 |
| E8 | unknown [*Theileria lestoquardi*] | 207 | gi|82622379 | 1 |
| B12 | calmodulin-like 5 [*Homo sapiens*] | 195 | gi|55859601 | 1 |
| D4 | Unknown (protein for MGC: 116262) [*Rattus norvegicus*] | 190 | gi|71051822 | 1 |
| A1 | hemoglobin beta | 182 | gi|229301 | 1 |
| C8 | Hemoglobin alpha subunit (Hemoglobin alpha chain) (Alpha-globin) | 172 | gi|122474 | 1 |
| D10 | Three-Dimensional Structure Of *Escherichia Coli* Thioredoxin-S2 To 2.8 Angstroms Resolution | 133 | gi|230335 | 1 |
| C8 | beta globin [*Callicebus torquatus*] | 124 | gi|33415435 | 1 |
| D10 | inter-alpha-inhibitor H4 heavy chain [*Rattus norvegicus*] | 116 | gi|9506819 | 1 |
| A7 | histidine-rich glycoprotein [*Mus musculus*] | 111 | gi|11066003 | 1 |
| B8 | profilin 1 [*Mus musculus*] | 111 | gi|56206029 | 1 |
| G6 | unnamed protein product [*Homo sapiens*] | 111 | gi|28317 | 1 |
| D10 | unnamed protein product [*Mus musculus*] | 109 | gi|26324736 | 1 |
| D10 | thioredoxin 1 (TRX1) (TRX) [*Photorhabdus luminescens* subsp. *laumondii* TTO1] | 100 | gi|36787919 | 1 |
| B8 | cystatin C precursor [*Mus musculus*] | 98 | gi|11762010 | 1 |
| D10 | hypothetical protein LOC77055 [*Mus musculus*] | 98 | gi|85701680 | 1 |
| D10 | LOC495267 protein [*Xenopus laevis*] | 98 | gi|54261576 | 1 |
| C8 | Hemoglobin alpha subunit (Hemoglobin alpha chain) (Alpha-globin) | 96 | gi|122405 | 1 |
| B8 | Transthyretin [*Mus musculus* | 95 | gi|56541070 | 1 |
| F7 | apolipoprotein J; SGP-2; TRPM-2 [*Mus musculus*] | 94 | gi|6273853 | 1 |
| D10 | thioredoxin [*Vibrio fischeri* ES114] | 90 | gi|59478765 | 1 |
| D10 | Zgc: 92061 [*Danio rerio*] | 90 | gi|49902693 | 1 |
| A2 | platelet factor 4 [*Mus musculus*] | 87 | gi|13560695 | 1 |

TABLE 7-continued

| Sample | Protein ID | Score | Swiss-Prot Ascension | Times identified |
|---|---|---|---|---|
| D10 | phosphoserine phosphatase [*Picrophilus torridus* DSM 9790] | 79 | gi|48431085 | 1 |
| B8 | parvalbumin [*Mus musculus*] | 77 | gi|509139 | 1 |
| D10 | Zgc: 92035 [*Danio rerio*] | 74 | gi|49904349 | 1 |
| C9 | apolipoprotein C2 [*Mus musculus*] | 67 | gi|817943 | 1 |
| H11 | possible glycosyltransferase [*Synechococcus* sp. WH 8102] | 65 | gi|33632163 | 1 |
| H7 | thrombospondin | 65 | gi|554390 | 1 |
| H3 | unnamed protein product [*Tetraodon nigroviridis*] | 63 | gi|47227197 | 1 |
| B12 | glyceraldehyde-3-phosphate dehydrogenase [*Homo sapiens*] | 62 | gi|31645 | 1 |
| B7 | hypothetical protein SAV6338 [*Streptomyces avermitilis* MA-4680] | 62 | gi|29832880 | 1 |
| D10 | hypothetical protein LOC496627 [*Xenopus tropicalis*] | 62 | gi|58332100 | 1 |
| D7 | fetuin [*Mus musculus*] | 60 | gi|2546995 | 1 |
| D4 | unnamed protein product [*Oryza sativa (japonica* cultivar-group)] | 59 | gi|34906342 | 1 |
| E5 | major surface glycoprotein [*Pneumocystis carinii* f. sp. *hominis*] | 59 | gi|3560519 | 1 |
| A4 | Hemoglobin beta subunit (Hemoglobin beta chain) (Beta-globin) | 58 | gi|122606 | 1 |
| D10 | Transcriptional regulator, LytR family [*Bacillus thuringiensis* serovar *israelensis* ATCC 35646] | 58 | gi|75760497 | 1 |
| B8 | Flp pilus assembly protein CpaB family [*Burkholderia thailandensis* E264] | 57 | gi|83719123 | 1 |
| F6 | Tyrosyl-tRNA synthetase [*Lactobacillus sakei* subsp. *sakei* 23K] | 56 | gi|81428383 | 1 |
| D1 | Hypothetical protein LOC338797 [*Homo sapiens*] serine peptidase (alpha/beta hydrolase superfamily) fused to N-terminal uncharacterized domain | 55 | gi|70673359 | 1 |
| D10 | specific to cyanobacteria [*Prochlorococcus marinus* str. NATL2A] | 55 | gi|72002395 | 1 |
| E2 | recombinant platelet factor 4 | 54 | gi|209286 | 1 |
| Total Numbers | | | | 257 |
| Unique protein numbers | | | | 77 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of fractionating or separating very low molecular weight components from a fluid sample, said method comprising the steps of:
   (a) providing a fluid sample comprising a first component consisting of molecules having a molecular weight no higher than 20 kDa and a second component having a molecular weight higher than 20 kDa;
   (b) providing a substrate comprising a nanoporous material, wherein the nanoporous material comprises pores with a defined specific pore size that allows the entry of molecules of the first component and retains substantially all molecules of the first component and excludes substantially all molecules of the second component;
   (c) exposing the substrate to the sample for a first period of time sufficient for the first component to penetrate a nanoporous surface of the substrate and enter into the pores of the nanoporous material while the second component does not penetrate the nanoporous material;
   (d) washing the substrate for a second period of time sufficient to displace the second component from the substrate without removing the first component from pores of the nanoporous material;
   (e) exposing the substrate to a solvent to extract the first component from the pores substrate; and
   (f) analyzing a fraction of the first component that penetrated and entered into the nanoporous material.

2. The method of claim 1, wherein the fluid sample is a biological fluid selected from the group consisting of blood serum, blood plasma, blood, urine, seminal fluid, seminal plasma, pleural fluid, ascites, nipple aspirate, feces or saliva.

3. The method of claim 1, wherein the first component comprises peptides, antigens, antibodies, proteins, protein fragments, RNA and/or DNA.

4. The method of claim 1, wherein the nanoporous material is a nanoporous silicon.

5. The method of claim 1, wherein the nanoporous material is a nanoporous oxide material.

6. The method of claim 5, wherein the nanoporous oxide material is a nanoporous silica.

7. The method of claim 1, wherein the surface of the nanoporous material is modified to promote binding or adsorption of the first component thereto.

8. The method of claim 7, wherein the nanoporous material has an electrically charged surface.

9. The method of claim 7, wherein the nanoporous material has a surface modified with functional groups.

10. The method of claim 1, wherein the substrate is a film, a wafer, a particle or a microchip.

11. The method of claim 1, wherein the substrate is fabricated by a top-down technique.

12. The method of claim 1, wherein the substrate is fabricated by a top-down technique selected from photolithography, electron beam lithography, X-ray lithography, deep UV lithography and nanoprint lithography.

13. The method of claim 1, further comprising the step of extracting the first component from the nanoporous material.

14. The method of claim 1, further comprising the step of washing the nanoporous material subsequent to the step of exposing the nanoporous material to the sample.

15. The method of claim 1, wherein the nanoporous material directly adsorbs the first component by means of silanol groups present on the silica-based nanoporous material.

16. The method of claim 1, further comprising the step of analyzing the first component.

17. The method of claim 16, wherein the first component is analyzed by mass spectrometry, gel electrophoresis, chromatography, bioassay or a combination thereof.

18. The method of claim 17, wherein the mass spectrometry is MALDI-TOF mass spectrometry, LC/MS mass spectrometry, ESI-MS mass spectrometry, tandem mass spectrometry or SELDI mass spectrometry.

19. The method of claim 1, wherein the first component consists of molecules having a molecular weight no higher than 15 kDa.

20. The method of claim 1, wherein the first component consists of molecules having a molecular weight no higher than 10 kDa.

21. The method of claim 1, wherein the first component consists of molecules having a molecular weight no higher than 5 kDa.

22. The method of claim 1, wherein the first component is present in the sample at a concentration no higher than 1000 ng/ml.

23. The method of claim 1, wherein the first component is present in the sample at a concentration no higher than 200 ng/ml.

24. The method of claim 1, wherein the first component is present in the sample at a concentration no higher than 100 ng/ml.

25. The method of claim 1, wherein the first component is present in the sample at a concentration no higher than 20 ng/ml.

26. The method of claim 1, wherein the first component is present in the sample at a concentration no higher than 10 ng/ml.

27. The method of claim 7, wherein the nanoporous material has a surface modified with metals.

28. The method of claim 1, wherein the substrate has a surface constructed with several nanoporous regions distributed over an inert, non-porous, non-adsorbent silicon chip surface.

29. The method of claim 28, wherein each nanoporous region has a different molecular-weight specificity.

30. The method of claim 1 wherein the nanoporous material has a pore size distribution centered at 2-20 nm.

31. The method of claim 1 wherein the nanoporous material has a pore size distribution centered at 2-10 nm.

\* \* \* \* \*